United States Patent
Shah et al.

(10) Patent No.: US 11,504,362 B2
(45) Date of Patent: Nov. 22, 2022

(54) LIQUID DOSAGE FORMS TO TREAT CANCER

(71) Applicant: Exelixis, Inc., Alameda, CA (US)

(72) Inventors: Khalid Shah, Half Moon Bay, CA (US); Gisela Schwab, Hayward, CA (US); Steven Lacy, San Mateo, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 16/620,379

(22) PCT Filed: Jun. 8, 2018

(86) PCT No.: PCT/US2018/036703
§ 371 (c)(1),
(2) Date: Dec. 6, 2019

(87) PCT Pub. No.: WO2018/227119
PCT Pub. Date: Dec. 13, 2018

(65) Prior Publication Data
US 2020/0268737 A1     Aug. 27, 2020

Related U.S. Application Data

(60) Provisional application No. 62/517,736, filed on Jun. 9, 2017, provisional application No. 62/520,768, filed on Jun. 16, 2017.

(51) Int. Cl.
*A61K 31/47* (2006.01)
*A61P 35/00* (2006.01)
*A61K 9/00* (2006.01)

(52) U.S. Cl.
CPC ............ *A61K 31/47* (2013.01); *A61K 9/0053* (2013.01); *A61P 35/00* (2018.01)

(58) Field of Classification Search
CPC .... A61K 31/47; A61K 9/0053; A61K 9/0095; A61K 47/10; A61K 47/22; A61P 35/00
USPC .......................................................... 514/312
See application file for complete search history.

(56) References Cited

U.S. PATENT DOCUMENTS

| | | | |
|---|---|---|---|
| 2012/0035212 A1* | 2/2012 | Brown | A61P 5/14 514/312 |
| 2012/0070368 A1* | 3/2012 | Bannen | A61K 31/517 424/1.11 |
| 2014/0235631 A1 | 8/2014 | Bunt et al. | |

FOREIGN PATENT DOCUMENTS

| | | |
|---|---|---|
| EA | 201500128 A1 | 5/2015 |
| JP | 2014-513129 | 5/2014 |
| WO | 2012-151326 | 11/2012 |
| WO | 2014009926 A1 | 1/2014 |

(Continued)

OTHER PUBLICATIONS

Neophytou et al, D-alpha-tocopheryl polyethylene glycol succinate (TPGS) induces cell cycle arrest and apoptosis selectively in Survivin-overexpressing breast cancer cells, Biochemical Pharmacology 89 (2014) 31-42. (Year: 2014).*

(Continued)

*Primary Examiner* — Taylor V Oh
(74) *Attorney, Agent, or Firm* — Honigman LLP; Heidi M. Berven

(57) ABSTRACT

This invention relates to a liquid pharmaceutical composition comprising cabozantinib to treat locally advanced or metastatic solid tumors, particularly advanced urothelial cancer or renal cell carcinoma in patients in need thereof.

13 Claims, 8 Drawing Sheets

(56) References Cited

FOREIGN PATENT DOCUMENTS

| WO | 2015123639 | | 8/2015 | |
|---|---|---|---|---|
| WO | WO-2015123639 A1 | * | 8/2015 | ........... C07D 215/22 |
| WO | 2015164869 | | 10/2015 | |
| WO | 2016019285 | | 2/2016 | |
| WO | 2018227119 | | 12/2018 | |

OTHER PUBLICATIONS

Bentzien, et al., "In Vitro and In Vivo Activity of Cabozantinib (XL184), an Inhibitor of RET, MET, and VEGFR2, in a Model of Medullary Thyroid Cancer", Thyroid, vol. 23, No. 12, pp. 1569-1577, Dec. 1, 2013.

International Search Report for PCT/US2018/036703, dated Dec. 13, 2018.

Kurzrock, R., et al., "Activity of XL184 (Cabozantinib), an oral tyrosine kinase inhibitor, in patients with medullary thyroid cancer", Journal of Clinical Oncology, vol. 29, No. 19, pp. 2660-2666, Jul. 1, 2011.

Lacy, et al., "Metabolism and Disposition of Cabozantinib in Healthy Male Volunteers and Pharmacologic Characterization of Its Major Metabolites", Drug Metabolism and Disposition, vol. 43, pp. 1190-1207, Aug. 2015.

Yakes, et al., "Cabozantinib (XL184), a novel MET and VEGFR2 inhibitor, simultaneously suppresses metastasis, angiogenesis and tumor growth", Mol Cancer Ther, No. 10, pp. 2298-2308, Sep. 16, 2011.

Yang, et al., "Cabozantinib Loaded DSPE-PEG2000 Micelles as Delivery System: Formulation, Characterization and Cytotoxicity Evaluation", BAOJ Pharmaceutical Science, pp. 1-20, Jan. 15, 2015.

Yu, S. S., et al., "Clinical use of cabozantinib in the treatment of advanced kidney cancer: efficacy, safety, and patient selection". OncoTargets and Therapy, Sep. 23, 2016, vol. 2016, No. 9, pp. 5825-5837.

Wiktionary, citation for Halo, (https://en.Wiktionary.org/wiki/halo-#:~:text=(chemistry)%20Forming%20names%20of%20chemical,one%20or%20more%20halogen%20atoms) printed Aug. 20, 2021, 3 pages.

FDA Label for Cabometyx, Apr. 2016.

Apolo, "Cabozantinib for Advanced Urothelial Cancer"—ClinicalTrials.gov, Sep. 20, 2012, retrieved from the Internet at https://clinicaltrials.gov/ct2/show/NCT01688999 on Mar. 21, 2022.

* cited by examiner

\* Co-eluted with Demethyl XL184 glucuronide B
\*\* Co-eluted with Half-dimer methyl ester \* Co-eluted with Demethyl XL184 glucuronide B
\*\* Co-eluted with Half-dimer methyl ester

* Co-eluted with Demethyl XL184 glucuronide B
** Co-eluted with Half-dimer methyl ester

* Co-eluted with Demethyl XL184 glucuronide B
** Co-eluted with Half-dimer methyl ester

LIQUID DOSAGE FORMS TO TREAT CANCER

CROSS-REFERENCE TO RELATED APPLICATIONS

This application is a United States National Phase filing of PCT/US2018/036703, filed Jun. 8, 2018, which claims the benefit of priority to U.S. Provisional Application No. 62/517,736, filed Jun. 9, 2017, and priority to 62/520,768, filed Jun. 16, 2017, the entire contents of which are incorporated herein by reference.

FIELD OF INVENTION

This invention relates to a liquid pharmaceutical formulation comprising an L-malate salt of N-(4-{[6,7-bis(methyloxy)quinolin-4-yl]oxy}phenyl)-N'-(4-fluorophenyl)cyclopropane-1,1-dicarboxamide.

BACKGROUND OF THE INVENTION

Multi-targeted tyrosine kinase inhibitors (TKIs) chemotherapeutics have been instrumental in the recent advancements of anticancer treatment over the past several years. Tyrosine kinase inhibitor therapies have demonstrated broad clinical effects leading to new approved treatment options across multiple tumor types including renal cell carcinoma (RCC), urothelial carcinoma (UC), melanoma, non-small-cell lung cancer (NSCLC), and others. The success of this therapy type as a single agent has naturally led to interest in evaluating novel formulations that provide enhanced pharmacokinetics (PK) and pharmacodynamics (PD) of TKIs when used in combination with checkpoint inhibitors in search of further, possibly synergistic, anticancer clinical effects.

Medicaments, such as chemotherapeutic drugs that are administered orally, are dispensed to the patient in several dosage forms, including liquid forms such as solutions, syrups, emulsions, and suspensions, and more commonly, in solid forms such as capsules, caplets, and tablets. Children, older persons, and many other persons (including disabled or incapacitated patients) often have trouble swallowing tablets or capsules. In these situations, it is desirable to provide the drug either in a chewable solid form or a liquid form. Pharmaceutically active agents administered in solid dosage form are usually intended to be swallowed whole. In some cases, the unpleasant taste of the medicament in solid form is generally not of concern when formulating oral solid dosage forms, because the pharmaceutical's taste can be easily masked with an exterior coating.

However, despite the convenience of formulating medicaments in oral solid forms, for pediatric and geriatric patients, a liquid oral dosage form is preferred over a chewable dosage form. A liquid dosage form is especially preferred for pediatric and geriatric patients because of the ease with which it may be swallowed. Additionally, patients may be more inclined to comply with their medication instruction if the dosages are easier to ingest, particularly for products administered in large doses, requiring several tablets at a time.

Some liquid pharmaceutical compositions formulated for use by pediatric or geriatric patients are prepared by grinding a tablet dosage form into a powder and mixing the powder with a diluent. Such a formulation may cause some of the drug to remain undissolved, thereby affecting the therapeutic dose of drug in the composition. In addition, the powder exposes the unpleasant tasting pharmaceutically active agent, which may result in a lack of compliance due to the unacceptable taste. It is readily understood that such compositions are impractical and may result in underdosing or poor compliance.

SUMMARY OF THE INVENTION

The problem underlying the present invention is to provide a liquid dosage form containing a compound of Formula I, or a pharmaceutically acceptable salt thereof, which does not show the above-described disadvantages of the known dosage forms. In particular, the pharmaceutical formulation should be stable over a long time period, as well as physiologically acceptable and pleasing for pediatric and geriatric patients. In some embodiments, the liquid formulations of the present invention find utility in the treatment of cancer, for example, for the treatment of a solid tumor in a patient in need thereof.

In some embodiments, the solid tumor is a locally advanced or a metastatic solid tumor.

In some embodiments, the present invention is directed to a liquid pharmaceutical composition comprising a compound of Formula I or a pharmaceutically acceptable salt thereof:

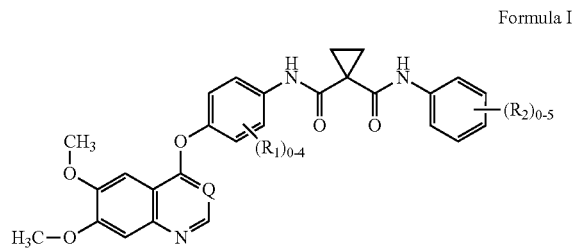

Formula I or a liquid pharmaceutical composition comprising the compound of formula I or a pharmaceutically acceptable salt thereof and a pharmaceutically acceptable carrier, wherein:
  $R^1$ is halo;
  $R^2$ is halo; and
  Q is CH or N.

In various embodiments, a single dose of the liquid pharmaceutical composition comprising a compound of formula I, or a pharmaceutically acceptable salt thereof, for example, compound 1, or a pharmaceutically acceptable salt thereof, provides an interpatient or intrapatient exposure variability of less than 30%, or less than 25%, or less than 20%, or less than 19%, or less than 18%, or less than 17%, or less than 16%, or less than 15%, or less than 14%, or less than 13%, or less than 12%, or less than 11%, or less than 10%. In various embodiments, the exposure is represented by a noncompartmental PK parameter selected from the group consisting of: $AUC_{0-t}$, $AUC_{0-24}$, $AUC_{0-72}$, $AUC_{0-inf}$, $C_{max}$, $t_{max}$, $k_{el}$, and $t_{1/2}$. In some embodiments, the liquid formulation of the present invention when dosed as a single dose provides an $AUC_{0-t}$, $AUC_{0-24}$, $AUC_{0-72}$, $AUC_{0-inf}$ or a $C_{max}$ interpatient or intrapatient variability of less than 30%, or less than 25%, or less than 20%, or less than 19%, or less than 18%, or less than 17%, or less than 16%, or less than 15%, or less than 14%, or less than 13%, or less than 12%, or less than 11%, or less than 10%. In some embodiments, the liquid formulation of the present invention when dosed as a single dose provides an $AUC_{0-t}$, $AUC_{0-24}$, $AUC_{0-72}$, $AUC_{0-inf}$ or $C_{max}$ interpatient or intrapatient variability of less than 30%, or less than 25%, or less than 20%, or less than 19%, or less than 18%, or less than 17%, or less than 16%, or less than 15%, or less than 14%, or less than 13%, or less than 12%, or less than 11%, or less than 10% relative to a tablet formulation containing a compound of formula I, or a pharmaceutically acceptable salt thereof, for example, compound 1, or a pharmaceutically acceptable salt thereof. In the above related embodiments, the single dose can include a single dose of about: 200 mg, 190 mg, 180 mg, 170 mg, 160 mg, 150 mg, 140 mg, 130 mg, 120 mg, 110 mg, 100 mg, 90 mg, 80 mg, 70 mg, 60 mg, 50 mg, 40 mg, 30 mg, 20 mg, or 10 mg of a compound of formula I, or compound 1 which can be the (L)-malate salt (also referred to herein as the S-malate salt; S-malate salt and (L)-malate salt are used interchangeably herein) or the (D)-malate salt (also referred to as the R-malate salt; R-malate salt and (D)-malate salt are used interchangeably herein). In various embodiments, the above referenced single doses comprises cabozantinib. Cabozantinib is also referred to as XL184, and XL184 and cabozantinib are used interchangeably herein.

Another aspect is directed to a method of treating a locally advanced or metastatic solid tumor, comprising administering to a patient in need of such treatment a liquid pharmaceutical composition comprising compound 1:

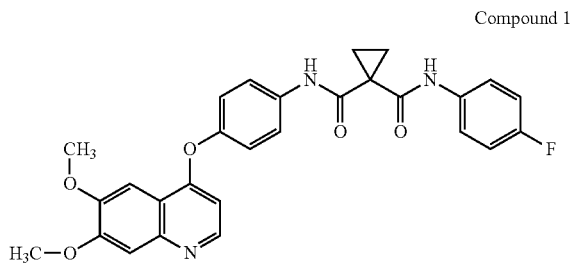 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof or a liquid pharmaceutical composition comprising compound 1 or a pharmaceutically acceptable salt thereof and a pharmaceutically acceptable carrier.

In some aspects, the locally advanced or a metastatic solid tumor may be advanced UC (urothelial carcinoma) or RCC (renal cell carcinoma).

In another aspect, the invention comprises a liquid pharmaceutical dosage form comprising a compound of formula I or compound 1, or a pharmaceutically acceptable salt thereof, such that each dose of the liquid pharmaceutical composition comprising compound 1, or a pharmaceutically acceptable salt thereof provides the patient an interpatient or intrapatient exposure (for example, $AUC_{0-t}$, $AUC_{0-24}$, $AUC_{0-inf}$, $C_{max}$, or $t_{max}$) variability of less than 30%, or less than 25%, or less than 20%, or less than 19%, or less than 18%, or less than 17%, or less than 16%, or less than 15%, or less than 14%, or less than 13%, or less than 12%, or less than 11%, or less than 10% relative to a tablet formulation containing the same amount of compound of formula I or compound 1, or a pharmaceutically acceptable salt thereof.

Figure 13:
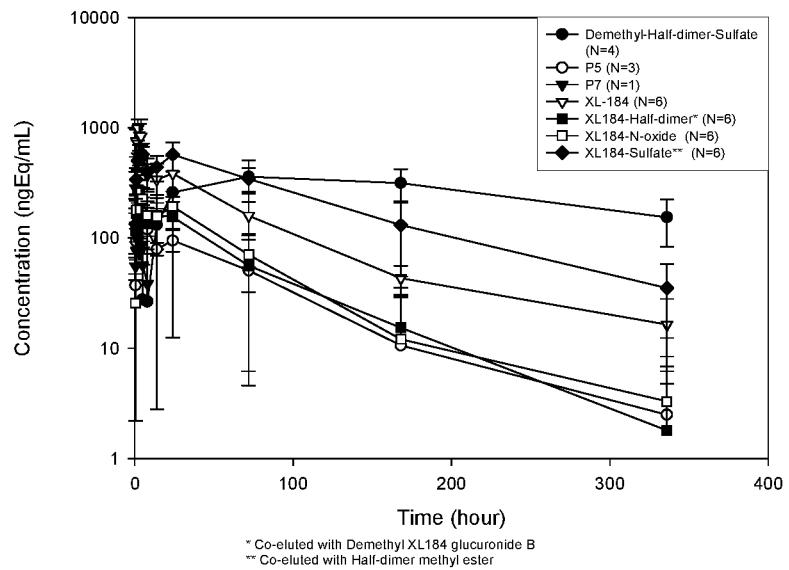

FIG. 13 depicts a line graph of the mean (±SD) plasma concentrations of demethyl half-dimer sulfate, P5, P7, XL-184, XL184-half-dimer, XL184-N-oxide, and XL184-sulfate measured by radio-quantitation method vs. time 0-336 hours following a single 175 mg oral administration of XL184 (L-malate salt) containing 100 µCi [$^{14}$C]-XL184 to healthy male subjects—semilogarithmic axes.

Figure 14:
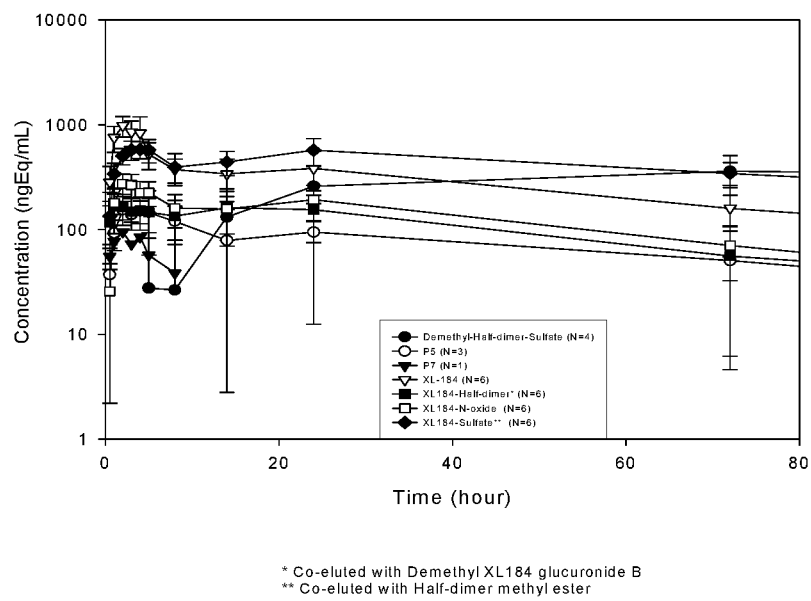

FIG. 14 depicts a line graph of the mean (±SD) plasma concentrations of demethyl half-dimer sulfate, P5, P7, XL-184, XL184-half-dimer, XL184-N-oxide, and XL184-sulfate measured by radio-quantitation method vs. time 0-80 hours following a single 175 mg oral administration of XL184 (L-malate salt) containing 100 µCi [$^{14}$C]-XL184 to healthy male subjects—semilogarithmic axes.

Figure 15:
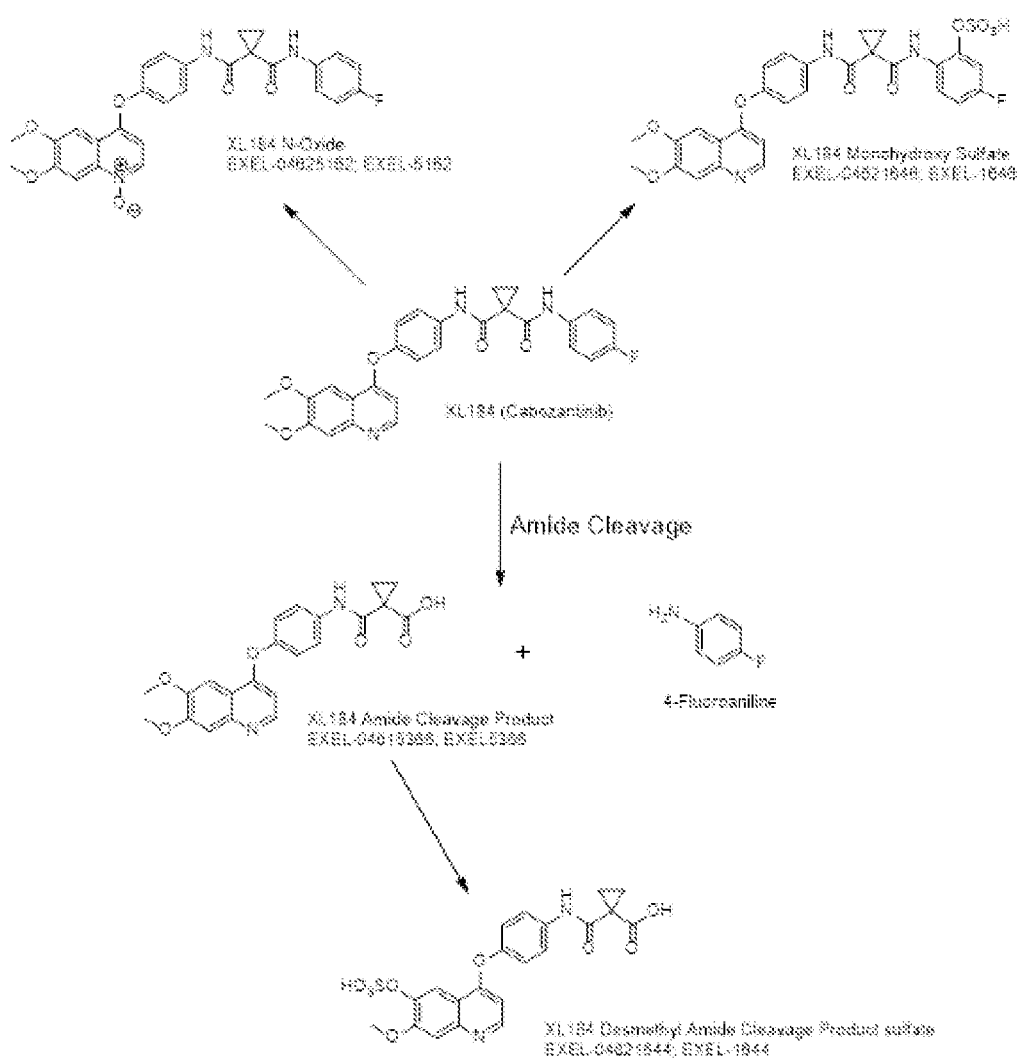

FIG. 15 depicts proposed major biotransformation products of XL184 (cabozantinib).

| Definitions | |
|---|---|
| ADME | Absorption, distribution, metabolism, and excretion |
| AE | Adverse event |
| ALT (SGPT) | Alanine aminotransferase (serum glutamic-pyruvate transaminase) |
| Anti-HAV | Hepatitis A total antibody |
| Anti-HBc | Hepatitis B core antigen antibody |
| Anti-HBs | Hepatitis B surface antigen antibody |
| AST (SGOT) | Aspartate aminotransferase (serum glutamic-oxaloacetic transaminase) |
| $AUC_{0-inf}$ | Area under the concentration-time curve from time zero to infinity |
| $AUC_{0-24}$ | Area under the concentration-time curve from time zero to time 24 hours |
| $AUC_{0-72}$ | Area under the concentration-time curve from time zero to time 72 hours |
| $AUC_{0-t}$ | Area under the concentration-time curve from time zero to time of the last measurable concentration |
| BMI | Body mass index |
| BUN | Blood urea nitrogen |
| ° C. | Degrees Celsius |
| Chem | Chemistry |
| $C_{max}$ | Maximum observed concentration |
| CTCAE | Common Terminology Criteria for Adverse Events |
| % CV | Percentage coefficient of variation |
| CYP | Cytochrome P450 |
| % Dose$_{(feces)}$ | Percentage of dose recovered in feces over the collection interval |
| % Dose$_{(urine)}$ | Percentage of dose recovered in urine over the collection interval |
| ECG | Electrocardiogram |
| eCRF | Electronic case report form |
| ETR | Percentage of $^{14}$C radioactivity associated with erythrocytes in whole blood |
| ° F. | Degrees Fahrenheit |
| g | Gram |
| GI | Gastrointestinal |
| GLP | Good laboratory practice |
| HBsAg | Hepatitis B surface antigen |
| HCV | Hepatitis C antibodies |
| Hem | Hematology |
| HIV | Human immunodeficiency virus |
| ICF | Informed consent form |
| ICH | International Conference on Harmonization |
| IGm | Immunoglobulin M |
| INN | International Nonproprietary Name |
| LLOQ | Lower limit of quantification |
| IRB | Institutional Review Board |
| $k_{el}$ | Apparent terminal elimination rate constant |
| kg | Kilogram |
| LC-MS/MS | Liquid chromatography-mass spectrometry/mass spectrometry |
| m | Meter |
| MBq | Megabecquerel |
| MedDRA ® | Medical Dictionary for Regulatory Activities |
| MET | Hepatocyte growth factor receptor protein |
| mg | Milligram |
| µCi | Microcurie |
| mL | Milliliter |
| mmHg | Micrometers of mercury |
| msec | millisecond |
| MTD | Maximum tolerated dose |
| NA | Not applicable |
| NCI | National Cancer Institute |
| NE | Not estimated |
| ng | Nanogram |
| ngEq | An equivalent amount of XL184 freebase required to produce a measured or calculated amount of total radioactivity |
| NR | Not reportable |
| p-FA | Para-fluoroaniline |
| PK | Pharmacokinetic |
| PO | Oral |
| QTc | Corrected QT interval |
| RBC | Red blood cell |
| RET | Rearranged during transfection |
| SAE | Serious adverse event |
| SAP | Statistical analysis plan |
| SD | Standard deviation |
| SOP | Standard operating procedure |
| TEAE | Treatment-emergent adverse event |
| $t_{max}$ | Time of maximum concentration |
| $t_{1/2}$ | Apparent terminal elimination half-life calculated as $\ln(2)/k_{el}$ |
| UPCr | Urine Protein/Creatinine ratio |
| US | United States of America |
| USAN | United States Adopted Name |
| VEGFR2 | Vascular endothelial growth factor receptor 2 |
| WBC | White blood cell |
| WHO | World Health Organization |
| XL184 | The product number used by Exelixis for development of the compound with the USAN/INN designation of cabozantinib |

DETAILED DESCRIPTION

As indicated above, the invention is directed to a method of treating a locally advanced or a metastatic solid tumor, comprising administering a liquid formulation of a compound of formula I or compound 1, or a pharmaceutically acceptable salt thereof.

Compound 1 is known by its chemical name N-(4-{[6,7-bis(methyloxy)quinolin-4-yl]oxy}phenyl)-N'-(4-fluorophenyl)cyclopropane-1,1-dicarboxamide and by the name cabozantinib (also referred to as XL184). COMETRIQ™ (Cabozantanib S-Malate oral capsules) has been approved by the Food and Drug Administration (FDA) in the United States on Nov. 29, 2012, for the treatment of patients with progressive, metastatic medullary thyroid cancer (MTC). CABOMETYX™ (Cabozantanib S-Malate oral tablets) has been approved by the Food and Drug Administration (FDA) in the United States on Apr. 25, 2016, for the treatment of advanced renal cell carcinoma (RCC) in patients who have received prior antiangiogenic therapy. Cabozantinib is formulated as the L-malate salt of N-(4-{[6,7-bis(methyloxy)quinolin-4-yl]oxy}phenyl)-N'-(4-fluorophenyl)cyclopropane-1,1-dicarboxamide. WO 2005/030140, the entire contents of which is incorporated herein by reference, discloses compound, describes how it is made (Example 48), and discloses the therapeutic activity of this compound to inhibit, regulate, and/or modulate the signal transduction of kinases (Assays, Table 4, entry 289). Example 48 begins at paragraph [0353] in WO 2005/030140. Information for compound 1 is available from the FDA at http://www.accessdata.fda.gov/scripts/cder/daf/index.cfm?event=overview.process&ApplNo=208692 (last visited Dec. 19, 2016) and is incorporated herein by reference in its entirety.

In various embodiments, the present invention provides a pharmaceutical composition formulated for oral administration in liquid form. When compared to solid forms, for example, a formulation in tablet, capsule, sachet, or powdered form, the liquid pharmaceutical compositions of the present invention comprising a compound of formula I or compound 1, which can be the (L)-malate salt or the (D)-malate salt, provides a significantly smaller interpatient or intrapatient variability in exposure. For example, as published in Nguyen, L. et al., "Pharmacokinetics of cabozantinib tablet and capsule formulations in healthy adults," (2016), *Anti-Cancer Drugs* 2016, 27:669-678, (the disclosure of which is incorporated herein by reference in its entirety), the values of $C_{max}$, $AUC_{0-t}$, and $AUC_{0-inf}$ plasma pharmacokinetic parameters were highly variable among study participants, ranging from (i.e. % CV about 48-72%, 42-56%, and 38-41% for the 20, 40, and 60 mg (free base equivalent, FBE) cabozantinib tablet strength treatments, respectively). Table 1 (reproduced from the Nguyen, L. et al., reference cited herein) summarizes the plasma PK parameters found when healthy patients were dosed with a single dose of 140 mg (free base equivalent, FBE) of cabozantinib or the malate salt of compound 1. The values of $C_{max}$, $AUC_{0-t}$, and $AUC_{0-inf}$ plasma pharmacokinetic parameters were highly variable among study participants (i.e. % CV about 54%, 44%, 46% and 43%, 37%, and 39% for the 140 mg (free base equivalent, FBE) cabozantinib tablet and capsule dose treatments, respectively).

TABLE 1

Summary of cabozantinib plasma pharmacokinetic parameters from healthy individuals administered a single oral dose of tablet or capsule formulations containing 140 mg of cabozantinib (free base equivalent, FBE).

| Pharmacokinetic parameter | Tablet treatment (mean ± CV %)[a] | Capsule treatment (mean ± CV %)[b] |
| --- | --- | --- |
| $C_{max}$ (ng/ml) | 702 ± 54 | 554 ± 43 |
| $t_{max}$ (h)[c] | 3.49 (1.99, 24.00) | 4.00 (2.00, 5.04) |
| $AUC_{0-t}$ (ng × h/ml) | 61 900 ± 44 | 54 900 ± 37 |
| $AUC_{0-inf}$ (ng × h/ml) | 65 800 ± 46 | 58 300 ± 39 |
| $t_{1/2}$ (h) | 115 ± 31 | 112 ± 26 |
| CL/F (l/h) | 2.61 ± 49 | 2.69 ± 32 |
| VZ/F (l) | 424 ± 58 | 426 ± 37 |

AUC, area under the plasma concentration-time curve; CL/F, oral clearance; CV, coefficient of variation.
[a]Treatment A (test): 140 mg dose (2 × 20 + 1 × 100 mg) of XL184 (cabozantinib) tablet formulation; (n = 72).
[b]Treatment B (reference): 140 mg dose (3 × 20 + 1 × 80 mg) of XL184 (cabozantinib) capsule formulation; (n = 72).
[c]Median (minimum, maximum) are presented.

In these and other embodiments, the compound of formula I or compound 1, or a pharmaceutically acceptable salt thereof, is administered as a liquid pharmaceutical composition, wherein the liquid pharmaceutical composition additionally comprises a pharmaceutically acceptable carrier, excipient, or diluent. In a specific embodiment, the compound of formula I is compound 1, or a pharmaceutically acceptable salt thereof.

The compound of formula I or compound 1, or a pharmaceutically acceptable salt thereof as described herein, includes both the recited compounds as well as individual isomers and mixtures of isomers. In each instance, the compound of formula I includes the pharmaceutically acceptable salts, hydrates, and/or solvates of the recited compounds and any individual isomers or mixture of isomers thereof.

In other embodiments, the compound of formula I or compound 1 can be the (L)-malate salt (also referred to herein as the S-malate salt), or the (D)-malate salt (also referred to as the R-malate salt). The malate salt of the compound of formula I and of compound 1 is disclosed in PCT/US2010/021194 and U.S. Patent Application Ser. No. 61/325,095, the entire contents of each of which are incorporated herein by reference.

In other embodiments, the compound of formula I can be malate salt.

In other embodiments, the compound of formula I can be the (D)-malate salt.

In other embodiments, the compound of formula I can be the (L)-malate salt.

In other embodiments, compound 1 can be the malate salt.

In other embodiments, compound 1 can be (D)-malate salt.

In other embodiments, compound 1 can be the (L)-malate salt.

In another embodiment, the malate salt is in the crystalline N-1 form of the (L) malate salt and/or the (D) malate salt of the compound 1 as disclosed in U.S. Patent Application Ser. No. 61/325,095. In another embodiment, the malate salt is the crystalline N-2 form of the (L) malate salt and/or the (D) malate salt of the compound 1 as disclosed in U.S. Patent Application Ser. No. 61/325,095. In yet another embodiment, the malate salt is a mixture of the N-1 and N-2 forms of the (L) malate salt and/or the (D) malate salt of the compound 1 as disclosed in U.S. Patent Application Ser. No. 61/325,095. See also WO 2008/083319 for the properties of crystalline enantiomers, including the N-2 crystalline forms of the (L)-malate salt (also referred to as the S-malate salt) or the (D)-malate salt (also referred to as the R-malate salt), and/or the N-1 crystalline forms of the (L)-malate salt (also referred to as the S-malate salt) or the (D)-malate salt (also referred to as the R-malate salt) of compound 1. Methods of making and characterizing such forms are fully described in PCT/US10/21194, which is incorporated herein by reference in its entirety.

In one embodiment, the compound of formula I or compound 1, or a pharmaceutically acceptable salt thereof, is administered once daily. In a further embodiment, a compound of formula I or compound 1, or a pharmaceutically acceptable salt thereof, is administered with fasting (i.e., without eating) for approximately two hours before and 1 hour after administration.

In another embodiment, the compound of formula I or compound 1, or a pharmaceutically acceptable salt thereof, is administered orally once daily as a liquid formulation.

In another embodiment, the compound of formula I or compound 1, or a pharmaceutically acceptable salt thereof, is administered orally as its free base or malate salt as a liquid formulation.

In various embodiments, a single dose of the liquid pharmaceutical composition comprising a compound of formula I, or a pharmaceutically acceptable salt thereof, for example, compound 1, or a pharmaceutically acceptable salt thereof, provides an interpatient or intrapatient exposure variability of less than 30%, or less than 25%, or less than 20%, or less than 19%, or less than 18%, or less than 17%, or less than 16%, or less than 15%, or less than 14%, or less than 13%, or less than 12%, or less than 11%, or less than 10%. In various embodiments, the exposure is represented by a noncompartmental PK parameter selected from the group consisting of: $AUC_{0-t}$, $AUC_{0-24}$, $AUC_{0-72}$, $AUC_{0-inf}$, $C_{max}$, $t_{max}$, $k_{el}$, and $t_{1/2}$. In some embodiments, the liquid formulation of the present invention when dosed as a single dose provides an $AUC_{0-t}$, $AUC_{0-24}$, $AUC_{0-72}$, $AUC_{0-inf}$, or a $C_{max}$ interpatient or intrapatient variability of less than 30%, or less than 25%, or less than 20%, or less than 19%, or less than 18%, or less than 17%, or less than 16%, or less than 15%, or less than 14%, or less than 13%, or less than 12%, or less than 11%, or less than 10%. In some embodiments, the liquid formulation of the present invention when dosed as a single dose provides an $AUC_{0-t}$, $AUC_{0-24}$, $AUC_{0-72}$, $AUC_{0-inf}$ or $C_{max}$ interpatient or intrapatient variability of less than 30%, or less than 25%, or less than 20%, or less than 19%, or less than 18%, or less than 17%, or less than 16%, or less than 15%, or less than 14%, or less than 13%, or less than 12%, or less than 11%, or less than 10% relative to a tablet formulation containing a compound of formula I, or a pharmaceutically acceptable salt thereof, for example, compound 1, or a pharmaceutically acceptable salt thereof.

In the above related embodiments, the single dose can include a single dose of about: 200 mg, 190 mg, 180 mg, 170 mg, 160 mg, 150 mg, 140 mg, 130 mg, 120 mg, 110 mg, 100 mg, 90 mg, 80 mg, 70 mg, 60 mg, 50 mg, 40 mg, 30 mg, 20 mg, or 10 mg of a compound of formula I or compound 1, which can be the (L)-malate salt (also referred to herein as the S-malate salt) or the (D)-malate salt (also referred to as the R-malate salt). In various embodiments, the above referenced single doses comprises cabozantinib.

The amounts of the compound of formula I or compound 1, or a pharmaceutically acceptable salt thereof, that are administered will vary. In one embodiment, the compound of formula I or compound 1, or a pharmaceutically acceptable salt thereof, is administered in an amount of from about 1 mg to about 200 mg, or from about 5 mg to about 175 mg, or from about 10 mg to about 100 mg, for example, 190 mg, 180 mg, 170 mg, 160 mg, 150 mg, 140, mg, 130 mg, 120 mg, 110 mg, 100 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, or 15 mg, within a fixed liquid dosage volume, for example, in a volume of about 1.0 mL to about 100 mL, or for example from about 10 mL to about 100 mL per unit dose. In another embodiment, the amount of the compound of formula I or compound 1, or a pharmaceutically acceptable salt thereof, is administered in an amount of 190 mg, 180 mg, 170 mg, 160 mg, 150 mg, 140, mg, 130 mg, 120 mg, 110 mg, 100 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, or 15 mg per unit volume (equivalent to a daily dose or a unit dose, or some fraction or part thereof) ranging from about 1 mL to about 100 mL, or from about 10 mL to about 100 mL per dose. In another embodiment, the amount of the compound of formula I or compound 1, or a pharmaceutically acceptable salt thereof, is administered in an amount of about 140 mg, about 80 mg, about 60 mg, about 40 mg, or about 20 mg per unit volume (equivalent to a daily dose or a unit dose, or some fraction or part thereof) ranging from about 1 mL to about 100 mL, or from about 10 mL to about 100 mL per unit dose. In another embodiment, the amount of the compound of formula I or compound 1, or a pharmaceutically acceptable salt thereof, is administered in a volume ranging from about 1 mL to about 100 mL, or from about 10 mL to about 100 mL per dose (equivalent to a daily dose, or a unit dose, or some fraction or part thereof), wherein each dose contains about 60 mg, or about 40 mg, or about 20 mg of the compound of formula I or compound 1, or a pharmaceutically acceptable salt thereof, for example, an (L)-malate salt (also referred to as the S-malate salt) or the (D)-malate salt (also referred to as the R-malate salt), and/or the N-1 crystalline forms of the (L)-malate salt (also referred to as the S-malate salt) or the (D)-malate salt (also referred to as the R-malate salt) of compound 1.

In these and other embodiments, the compound of formula I or compound 1, or a pharmaceutically acceptable salt thereof, is administered orally once daily as its free base or as the malate salt as a liquid dosage form, preferably in a daily dose, or a unit dose, or some fraction or part thereof. In a further embodiment, compound 1 is administered as the (L)-malate salt (also referred to as the S-malate salt) or the (D)-malate salt (also referred to as the R-malate salt). In a further embodiment:

up to and including 150 mg of compound 1 or a pharmaceutically acceptable salt thereof is administered;
up to and including 140 mg of compound 1 or a pharmaceutically acceptable salt thereof is administered;
up to and including 130 mg of compound 1 or a pharmaceutically acceptable salt thereof is administered;
up to and including 120 mg of compound 1 or a pharmaceutically acceptable salt thereof is administered;
up to and including 110 mg of compound 1 or a pharmaceutically acceptable salt thereof is administered;
up to and including 100 mg of compound 1 or a pharmaceutically acceptable salt thereof is administered;
up to and including 95 mg of compound 1 or a pharmaceutically acceptable salt thereof is administered;
up to and including 90 mg of compound 1 or a pharmaceutically acceptable salt thereof is administered;
up to and including 85 mg of compound 1 or a pharmaceutically acceptable salt thereof is administered;
up to and including 80 mg of compound 1 or a pharmaceutically acceptable salt thereof is administered;
up to and including 75 mg of compound 1 or a pharmaceutically acceptable salt thereof is administered;
up to and including 70 mg of compound 1 or a pharmaceutically acceptable salt thereof is administered;
up to and including 65 mg of compound 1 or a pharmaceutically acceptable salt thereof is administered;
up to and including 60 mg of compound 1 or a pharmaceutically acceptable salt thereof is administered;
up to and including 55 mg of compound 1 or a pharmaceutically acceptable salt thereof is administered;
up to and including 50 mg of compound 1 or a pharmaceutically acceptable salt thereof is administered;
up to and including 45 mg of compound 1 or a pharmaceutically acceptable salt thereof is administered;
up to and including 40 mg of compound 1 or a pharmaceutically acceptable salt thereof is administered;
up to and including 35 mg of compound 1 or a pharmaceutically acceptable salt thereof is administered;
up to and including 30 mg of compound 1 or a pharmaceutically acceptable salt thereof is administered;
up to and including 25 mg of compound 1 or a pharmaceutically acceptable salt thereof is administered;
up to and including 20 mg of compound 1 or a pharmaceutically acceptable salt thereof is administered;
up to and including 15 mg of compound 1 or a pharmaceutically acceptable salt thereof is administered;
up to and including 10 mg of compound 1 or a pharmaceutically acceptable salt thereof is administered; or
up to and including 5 mg of compound 1 or a pharmaceutically acceptable salt thereof is administered.

In each of the aforementioned examples, the amount of compound 1 or a pharmaceutically acceptable salt thereof is admixed with one or more carriers to prepare an oral formulation containing, for example, from about 50% to about 95% PEG-400 (w/w), and/or from about 1% to about 30% TPGS (w/w), and/or from about 0.5% to about 20% ethanol (w/w). In each of the aforementioned examples, the amount of compound 1 or a pharmaceutically acceptable salt thereof is admixed with one or more carriers to prepare an oral formulation containing, for example, from about 70% to about 90% PEG-400 (w/w), and/or from about 5% to about 20% TPGS (w/w), and/or from about 1% to about 15% ethanol (w/w).

In each of the aforementioned examples, the amount of compound 1 or a pharmaceutically acceptable salt thereof is admixed with one or more carriers to prepare an oral formulation containing, for example, from about 80% to about 90% PEG-400 (w/w), and/or from about 5% to about 15% TPGS (w/w), and/or from about 1% to about 10% ethanol (w/w).

In each of the aforementioned examples, the amount of compound 1 or a pharmaceutically acceptable salt thereof is admixed with one or more carriers to prepare an oral formulation containing, for example, about 85% PEG-400 (w/w), and/or about 10% TPGS (w/w), and/or about 5% ethanol (w/w).

In these and other embodiments, a liquid formulation comprising compound 1 which is administered orally once daily with fasting as its free base or as a malate salt (for example, the (L)-malate salt, which is also referred to as the S-malate salt, or the (D)-malate salt, which is also referred to as the R-malate salt) to a patient in need thereof. In a further embodiment:

up to and including 150 mg of compound 1 or a pharmaceutically acceptable salt thereof is administered;
up to and including 140 mg of compound 1 or a pharmaceutically acceptable salt thereof is administered;
up to and including 130 mg of compound 1 or a pharmaceutically acceptable salt thereof is administered;
up to and including 120 mg of compound 1 or a pharmaceutically acceptable salt thereof is administered;
up to and including 110 mg of compound 1 or a pharmaceutically acceptable salt thereof is administered;
up to and including 100 mg of compound 1 or a pharmaceutically acceptable salt thereof is administered;
up to and including 95 mg of compound 1 or a pharmaceutically acceptable salt thereof is administered;
up to and including 90 mg of compound 1 or a pharmaceutically acceptable salt thereof is administered;
up to and including 85 mg of compound 1 or a pharmaceutically acceptable salt thereof is administered;
up to and including 80 mg of compound 1 or a pharmaceutically acceptable salt thereof is administered;
up to and including 75 mg of compound 1 or a pharmaceutically acceptable salt thereof is administered;
up to and including 70 mg of compound 1 or a pharmaceutically acceptable salt thereof is administered;
up to and including 65 mg of compound 1 or a pharmaceutically acceptable salt thereof is administered;
up to and including 60 mg of compound 1 or a pharmaceutically acceptable salt thereof is administered;
up to and including 55 mg of compound 1 or a pharmaceutically acceptable salt thereof is administered;
up to and including 50 mg of compound 1 or a pharmaceutically acceptable salt thereof is administered;
up to and including 45 mg of compound 1 or a pharmaceutically acceptable salt thereof is administered;
up to and including 40 mg of compound 1 or a pharmaceutically acceptable salt thereof is administered;
up to and including 35 mg of compound 1 or a pharmaceutically acceptable salt thereof is administered;
up to and including 30 mg of compound 1 or a pharmaceutically acceptable salt thereof is administered;
up to and including 25 mg of compound 1 or a pharmaceutically acceptable salt thereof is administered;
up to and including 20 mg of compound 1 or a pharmaceutically acceptable salt thereof is administered;
up to and including 15 mg of compound 1 or a pharmaceutically acceptable salt thereof is administered;
up to and including 10 mg of compound 1 or a pharmaceutically acceptable salt thereof is administered; or
up to and including 5 mg of compound 1 or a pharmaceutically acceptable salt thereof is administered, In each of the aforementioned examples, the amount of compound 1 or a pharmaceutically acceptable salt thereof is admixed with one or more carriers to prepare an oral formulation containing, for example, from about 50% to about 95% PEG-400 (w/w), and/or from about 1% to about 30% TPGS (w/w), and/or from about 0.5% to about 20% ethanol (w/w).

In each of the aforementioned examples, the amount of compound 1 or a pharmaceutically acceptable salt thereof is admixed with one or more carriers to prepare an oral formulation containing, for example, from about 70% to about 90% PEG-400 (w/w), and/or from about 5% to about 20% TPGS (w/w), and/or from about 1% to about 15% ethanol (w/w).

In each of the aforementioned examples, the amount of compound 1 or a pharmaceutically acceptable salt thereof is admixed with one or more carriers to prepare an oral formulation containing, for example, from about 80% to about 90% PEG-400 (w/w), and/or from about 5% to about 15% TPGS (w/w), and/or from about 1% to about 10% ethanol (w/w).

In each of the aforementioned examples, the amount of compound 1 or a pharmaceutically acceptable salt thereof is admixed with one or more carriers to prepare an oral formulation containing, for example, about 85% PEG-400 (w/w), and/or about 10% TPGS (w/w), and/or about 5% ethanol (w/w).

In various embodiments, a patient with a solid tumor, for example, a locally advanced or metastatic solid tumor, may be treated with compound 1, or a pharmaceutically acceptable salt thereof, as a liquid formulation containing 140 mg, 80 mg, 60 mg, 40 mg, or 20 mg of compound 1, which is administered orally once daily with fasting as its free base or as a malate salt (for example, the (L)-malate salt, which is also referred to as the S-malate salt, or the (D)-malate salt, which is also referred to as the R-malate salt).

In various embodiments, a patient with a solid tumor, for example, a locally advanced or metastatic solid tumor, may be treated with cabozantinib (S)-malate, which is administered orally once daily with fasting as a liquid dosage form comprising cabozantinib (S)-malate.

In a further embodiment, the cabozantinib (S)-malate is administered in a liquid pharmaceutical composition formulation containing 140 mg, 80 mg, 60 mg, 40 mg, or 20 mg of cabozantinib orally once daily with fasting. In a further embodiment, as shown in Table 1, the cabozantinib (S)-malate is administered in a liquid pharmaceutical composition which comprises one or more excipients, carriers, or diluents. Depending on the type of pharmaceutical composition, the pharmaceutically acceptable carrier may be chosen from any one or a combination of carriers known in the art. The choice of the pharmaceutically acceptable carrier depends partly upon the desired method of administration to be used. For a pharmaceutical composition of this disclosure, that is, one of the active compound(s) or a crystalline form of one of the active compound(s) of formula I or compound 1, a carrier should be chosen so as to substantially maintain the particular form of the active compound(s), whether it is crystalline or not. In other words, the carrier should not substantially alter the form of the active compound(s), nor should the carrier be otherwise incompatible with the form of the active compound(s), such as by producing any undesirable biological effect or otherwise interacting in a deleterious manner with any other component(s) of the pharmaceutical composition. Various carriers used in formulating pharmaceutically acceptable compositions and known techniques for their bulk preparation and subsequent production into unit dosage forms are employed to make the pharmaceutical compositions disclosed herein and are described in Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York. The amount of carriers and excipients used in a composition can be varied proportionally according to the amount of active ingredient used (that is, a compound of formula I or compound I, or a pharmaceutically acceptable salt thereof). For example, in each of the aforementioned examples, the amount of compound 1 or a pharmaceutically acceptable salt thereof is admixed with one or more carriers to prepare an oral formulation containing, for example, from about 50% to about 95% PEG-400 (w/w), and/or from about 1% to about 30% TPGS (w/w), and/or from about 0.5% to about 20% ethanol (w/w).

In each of the aforementioned examples, the amount of compound 1 or a pharmaceutically acceptable salt thereof is admixed with one or more carriers to prepare an oral formulation containing, for example, from about 70% to about 90% PEG-400 (w/w), and/or from about 5% to about 20% TPGS (w/w), and/or from about 1% to about 15% ethanol (w/w).

In each of the aforementioned examples, the amount of compound 1 or a pharmaceutically acceptable salt thereof is admixed with one or more carriers to prepare an oral formulation containing, for example, from about 80% to about 90% PEG-400 (w/w), and/or from about 5% to about 15% TPGS (w/w), and/or from about 1% to about 10% ethanol (w/w).

In each of the aforementioned examples, the amount of compound 1 or a pharmaceutically acceptable salt thereof is admixed with one or more carriers to prepare an oral formulation containing, for example, about 85% PEG-400 (w/w), and/or about 10% TPGS (w/w), and/or about 5% ethanol (w/w).

Suitable carriers include, but are not limited to, water, saline, aqueous dextrose, glycerol, ethanol, and the like; solubilizing agents and emulsifiers, such as ethyl alcohol, isopropyl alcohol, ethyl carbonate, ethyl acetate, benzyl alcohol, benzyl benzoate, propyleneglycol, 1,3-butyleneglycol, and dimethylformamide; oils, such as cottonseed oil, groundnut oil, corn germ oil, olive oil, castor oil, and sesame oil, glycerol, tetrahydrofurfuryl alcohol, polyethyleneglycols, and fatty acid esters of sorbitan; or mixtures of these substances, and the like, to thereby form a solution or suspension.

The liquid pharmaceutical compositions of this disclosure may be prepared by methods know in the pharmaceutical formulation art, for example, see Remington's Pharmaceutical Sciences, 18th Ed., (Mack Publishing Company, Easton, Pa., 1990).

Pharmaceutically acceptable adjuvants known in the pharmaceutical formulation art may also be used in the pharmaceutical compositions of this disclosure. These include, but are not limited to, preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. If desired, a pharmaceutical composition of this disclosure may also contain minor amounts of auxiliary substances, such as wetting or emulsifying agents, pH buffering agents, and antioxidants, such as, for example, citric acid, sorbitan monolaurate, triethanolamine oleate, and butylated hydroxytoluene. The pharmaceutical compositions generally contain about 0.5% to about 99.5% by weight of the active compound(s), or a crystalline form of the active compound(s), and 99.5% to 0.5% by weight of a suitable pharmaceutical excipient. In one example, the composition will be between about 1% and about 75% by weight of active compound, with the rest being suitable pharmaceutical excipients or other adjuvants, as discussed herein.

Liquid dosage forms for oral administration include pharmaceutically acceptable emulsions, solutions, suspensions, syrups, and elixirs. Such dosage forms are prepared, for example, by dissolving, dispersing, etc., one or more compound(s) of this disclosure, or a pharmaceutically acceptable salt thereof, and optional pharmaceutical adjuvants in a carrier, such as, for example, water, saline, aqueous dextrose, glycerol, polyethylene glycol (PEG), ethanol, and the like; and further comprising solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan; or mixtures of these substances, and the like, to thereby form a solution or suspension.

Suspensions, in addition to the active compounds, can contain suspending agents, as for example, ethoxylated isostearyl alcohols, polyoxyethylene sorbitol, and sorbitan esters, microcrystalline cellulose, aluminum metahydroxide, bentonite, agar-agar, and tragacanth, or mixtures of these substances, and the like.

TABLE 2

An example of a liquid formulation containing cabozantinib (S)-malate.

| Ingredient | Theoretical Quantity (mg/unit dose) | | |
| --- | --- | --- | --- |
| | 20-mg Dose | 40-mg Dose | 60-mg Dose |
| Cabozantinib (S)-malate | 25.34 | 50.68 | 76.02 |
| Polyethylene glycol 400 (PEG 400) | 2,934.88 | 5,869.77 | 8,804.65 |
| d-α-tocopheryl polyethylene glycol succinate (TPGS) | 345.28 | 690.56 | 1,035.84 |
| Ethanol | 172.64 | 345.28 | 517.92 |
| Flavorings | 3.45 | 6.91 | 10.36 |
| Total | 3,481.60 | 6,963.19 | 10,444.79 |

In a further embodiment, the cabozantinib (S)-malate is administered orally once daily.

In a further embodiment, the amount of cabozantinib (S)-malate that is administered orally once daily is 140 mg.

In a further embodiment, the amount of cabozantinib (S)-malate that is administered orally once daily is 120 mg.

In a further embodiment, the amount of cabozantinib (S)-malate that is administered orally once daily is 80 mg.

In a further embodiment, the amount of cabozantinib (S)-malate that is administered orally once daily is 60 mg.

In a further embodiment, the amount of cabozantinib (S)-malate that is administered orally once daily is 40 mg.

In a further embodiment, the amount of cabozantinib (S)-malate that is administered orally once daily is 20 mg.

In a further embodiment, the cabozantinib (R)-malate is administered orally once daily.

In a further embodiment, the amount of cabozantinib (R)-malate that is administered orally once daily is 140 mg.

In a further embodiment, the amount of cabozantinib (R)-malate that is administered orally once daily is 120 mg.

In a further embodiment, the amount of cabozantinib (R)-malate that is administered orally once daily is 80 mg.

In a further embodiment, the amount of cabozantinib (R)-malate that is administered orally once daily is 60 mg.

In a further embodiment, the amount of cabozantinib (R)-malate that is administered orally once daily is 40 mg.

In a further embodiment, the amount of cabozantinib (R)-malate that is administered orally once daily is 20 mg.

In another embodiment, compound 1 is administered orally as its free base or a malate salt (for example, the (L)-malate salt, which is also referred to as the S-malate salt, or the (D)-malate salt, which is also referred to as the R-malate salt) once daily in a liquid pharmaceutical composition as provided in the following Table 3.

TABLE 3

An example of a liquid formulation containing cabozantinib (S)-malate.

| Ingredient | (% w/w) |
| --- | --- |
| Compound 1 | 0.73 |
| Polyethylene glycol 400 (PEG 400) | 84.30 |
| d-α-tocopheryl polyethylene glycol succinate (TPGS) | 9.92 |
| Ethanol | 4.96 |
| Flavorings | 0.10 |
| Total | 100 |

In another embodiment, compound 1 is administered orally as its free base or a malate salt ((L)-malate salt (also referred to as the S-malate salt), or the (D)-malate salt (also referred to as the R-malate salt)) once daily in a liquid pharmaceutical composition as provided in the following table 4.

TABLE 4

An example of a liquid formulation containing cabozantinib (S)-malate.

| Ingredient | Theoretical Quantity (mg/unit dose) |
| --- | --- |
| Compound 1 | 175.00 |
| Polyethylene glycol 400 (PEG 400) | 20,268.53 |
| d-α-tocopheryl polyethylene glycol succinate (TPGS) | 2,384.53 |

TABLE 4-continued

An example of a liquid formulation containing cabozantinib (S)-malate.

| Ingredient | Theoretical Quantity (mg/unit dose) |
| --- | --- |
| Ethanol | 1,192.27 |
| Flavorings | 23.85 |
| Total | 24,044.18 |

In another embodiment, compound 1 is administered orally as its free base or a malate salt ((L)-malate salt (also referred to as the S-malate salt), or the (D)-malate salt (also referred to as the R-malate salt)) once daily as a liquid dose as provided in the following table 5.

TABLE 5

An example of a liquid formulation containing cabozantinib (S)-malate.

| Ingredient | Function | % w/w |
| --- | --- | --- |
| Cabozantinib (S)-malate | Active Ingredient | 0.73 |
| Polyethylene glycol 400 (PEG 400) | Solubility Enhancer | 84.30 |
| d-α-tocopheryl polyethylene glycol succinate (TPGS) | Solubility Enchancer and Stabilizer | 9.92 |
| Ethanol | Solvent | 4.96 |
| Cinnamon Flavoring | Taste masking agent | 0.10 |
| Total | | 100 |

Any of the liquid dosage formulations provided above can be adjusted according to the dose of compound 1 or a pharmaceutically acceptable salt thereof desired. Thus, the amount of each of the formulation ingredients can be proportionally adjusted to provide a liquid formulation containing various amounts of compound 1 or a pharmaceutically acceptable salt thereof as provided in the previous paragraphs. In another embodiment, the formulations can contain 20, 40, 60, or 80 mg of compound 1 or a pharmaceutically acceptable salt thereof.

Exemplary Administration of the Liquid Pharmaceutical Composition and Treatment of Solid Tumors Through potent inhibition of RTKs including MET, VEGFR, and AXL, cabozantinib has demonstrated clinical activity as a single agent in both advanced UC and RCC.

Objectives: The primary objectives of the study were: (1) to determine the time course for excretion of $^{14}C$ radioactivity in urine and feces following a single 175 mg oral dose of XL184 (L-malate salt) containing 100 μCi [14C]-XL184; (2) to determine the recovery of $^{14}C$ radioactivity as a percentage of the administered dose; (3) to determine the percentage of $^{14}C$ radioactivity present as XL184 in plasma and urine at selected time points following administration of the study drug; and (4) to assess the safety of a single dose of 175 mg of XL184 (L-malate salt) containing 100 μCi [$^{14}C$]-XL184 in healthy male subjects. The secondary objectives of the study were: (1) to determine the plasma pharmacokinetics of $^{14}C$ radioactivity and XL184 in healthy male subjects following a single oral dose of study drug; (2) to determine the percentage of $^{14}C$ radioactivity associated with erythrocytes in whole blood over time; and (3) to estimate the amount and probable structure of any significant metabolites or degradation products of XL184 in plasma and urine.

The following PK objectives listed above will not be addressed in this example:

Primary objective (3): to determine the percentage of $^{14}C$ radioactivity present as XL184 in plasma and urine at selected time points following administration of the study drug;

Secondary objective (3): to estimate the amount and probable structure of any significant metabolites or degradation products of XL184 in plasma and urine.

The study was completed as planned.

Methodology: This was an open-label, single-dose, single-center, mass balance, Phase 1 study in healthy male volunteers. There were two study periods: a Screening Period, during which subjects underwent assessments to determine their eligibility for the study, and an On-study Period, which started on Day-1 ('check-in' day) when the subject was admitted to the Celerion clinic. Subjects received a single calculated oral dose intended to contain a total of 175 mg of XL184 (L-malate salt) and 100 μCi of $^{14}C$ at Hour 0 on Day 1; initially they were to remain in the clinic through to the completion of all scheduled post-dose procedures on the morning of Day 28. Alternatively, if scintillation counts were available, subjects, on an individual basis, could be discharged prior to Day 28 if either of the following conditions were met: (1) ≥90% of the administered radioactivity was recovered in the urine and feces (accounting for radioactivity in vomitus if applicable); or (2) the daily total excreted radioactivity was 1% or less of the administered dose on 2 consecutive days and ≥85% of the administered radioactivity had been recovered. However, subjects who were discharged from the clinic before Day 28 were required to return to the clinic for all remaining scheduled pharmacokinetic blood sampling and the Day 28 safety assessments. Subjects not meeting radioactivity release criteria by Day 28 could be asked to remain confined in the clinic or continue collection of urine and feces at home (returning samples to the clinic daily) for up to an additional 7 days (through to Day 35). Due to the fact that by Day 35 subjects had still not met release criteria, subjects were given the option of withdrawing from the study or completing the additional 14-day collection period (either in the clinic or as a daily visitor) with urine and feces collections and daily adverse event (AE) inquiries. All urine and fecal collections for all subjects stopped following the conclusion of the Day 49 scheduled events regardless of percentage of total radioactive dose recovered.

Number of subjects (planned and analyzed): 8 planned and 8 analyzed

Diagnosis and main criteria for eligibility: Healthy male adults, aged 19 to 55 years of age, with screening and check in amylase or lipase levels below the upper limit of normal, a minimum of one bowel movement a day, and no evidence of urinary obstruction or difficulty in voiding urine at screening.

Test product, dose and mode of administration, and batch numbers: XL184 (L-malate salt) containing [$^{14}C$]-XL184 (100 μCi dose) was prepared as a dosing solution. Each dosing solution was analyzed for radioactivity content (scintillation counting), radiochemical purity, and XL184 concentration. A single dose oral solution was administered at Hour 0 on Day 1 by the clinic staff. The dose was given via the scintillation vial. Following dosing, the scintillation vial was rinsed 3 times with room temperature distilled water, and the rinsate was administered to the subject. Residual radioactivity was determined for each dosing vial. The total volume of liquid administered including radiolabelled study drug, rinses, and water given for dosing (in addition to the rinses) was the same for each subject.

Duration of treatment: Each subject was dosed with a single 175 mg oral solution dose of XL184 (L-malate salt) containing [$^{14}C$]-XL184 (100 μCi).

Reference therapy, dose and mode of administration, and batch numbers: Not applicable.

Criteria for Evaluation:

Efficacy: Not applicable (efficacy was not measured in this study)

Pharmacokinetics: Serial blood, urine, and feces were collected at specified times following dosing. As data allowed, standard noncompartmental pharmacokinetic parameters, including area under the concentration-time curve calculated using linear trapezoidal summation from time zero to time t, where t is the time of the last measurable concentration (AUC0-t), area under the concentration-time curve calculated using linear trapezoidal summation from time zero to time 24 hours ($AUC_{0-24}$), area under the concentration-time curve calculated using linear trapezoidal summation from time zero to time 72 hours ($AUC_{0-72}$), area under the concentration-time curve from time zero to infinity, $AUC_{0-inf}=AUC_{0-t}+Ct/kel$, where kel is the terminal elimination rate constant and $C_t$ is the last measurable concentration ($AUC_{0-inf}$), maximum observed concentration ($C_{max}$), time of maximum concentration ($t_{max}$), apparent terminal elimination rate constant calculated by linear regression of the terminal linear portion of the log concentration vs. time curve ($k_{el}$), and apparent terminal elimination half-life calculated as $\ln(2)/k_{el}(t_{1/2})$ were calculated from radioactivity data in plasma and whole blood, and standard noncompartmental pharmacokinetic parameters, including $AUC_{0-t}$, $AUC_{0-24}$, $AUC_{0-inf}$, $C_{max}$, $t_{max}$, $k_{el}$, and $t_{1/2}$, were calculated from XL184 and/or metabolite concentrations in plasma.

As data allowed, pharmacokinetic parameters, including urine concentration (Curine), amount excreted during each collection interval, calculated as $C_{urine} \times$ urine volume, renal clearance, cumulative amount of dose excreted in urine, percentage recovered in urine over the collection interval, and cumulative percent of dose recovered in urine, were calculated from XL184 and metabolites concentrations in urine. Fecal concentration ($C_{feces}$), amount excreted during each collection interval, calculated as $C_{feces} \times$ fecal weight, cumulative amount of dose excreted in feces, percentage of dose recovered in feces over the collection interval, and cumulative percent of dose recovered in feces, were also calculated from XL184 and metabolites concentrations in feces.

Mass balance was calculated as the percent of total administered radioactivity recovered in urine and feces. For the purpose of calculating mass balance, the amount of administered radioactivity was defined as the total radioactivity in the dosing solution minus any radioactivity lost due to emesis (if any occurred), adsorption to the dosing vial, etc.

To determine the percentage of radioactivity associated with erythrocytes in whole blood over time (ETR; calculated only for time points that whole blood is collected), the following was calculated:

The amount of $^{14}C$ radioactivity in plasma versus whole blood, adjusted for the hematocrit, at the specific time points of comparison (ETR=Xe/Xb=1−[Cp*(1−Hct)/Cb], where Xe and Xb stands for amount of radioactivity in erythrocyte or whole blood, respectively. Hematocrit values for Days-1, 2, and 4 were averaged for use in this calculation.

Safety: Safety evaluations included assessments of AEs, vital signs, electrocardiogram (ECG), laboratory tests, and concomitant medications. Adverse event seriousness, severity grade, and relationship to study treatment were assessed by the investigator. Severity grade was defined by the National Cancer Institute Common Terminology Criteria for Adverse Events (CTCAE) version 4.0.

Adverse event terms were standardized using the Medical Dictionary for Regulatory Activities and tabulated by system organ class and preferred term.

Metabolic Profiling: Details regarding metabolic profiling were prepared under separate cover by QPS, LLC. The results will be reported separately.

Statistical Methods:

Efficacy: Not applicable (efficacy was not measured in this study).

Pharmacokinetics: The pharmacokinetic parameters identified above were summarized using descriptive statistics (e.g., mean, median, standard deviation [SD], coefficient of variation (CV), standard error of the mean, geometric mean, minimum, maximum, and sample size). No inferential statistics were calculated. The radiocarbon concentration over each collection period was determined for plasma, whole blood, urine, and feces. To determine the percentage of radioactivity associated with erythrocytes in whole blood over time (calculated only for time points that whole blood is collected) the following was calculated: the amount of radioactivity in plasma versus whole blood, adjusted for the hematocrit, at the specific time points of comparison (ETR=Xe/Xb=1−[Cp*(1−Hct)/Cb], where Xe and Xb stands for amount of radioactivity in erythrocyte or whole blood, respectively. Hematocrit values for Days-1, 2, and 4 were averaged for use in this calculation.

Safety: AEs and other safety data were summarized and listed as appropriate. Laboratory values were presented to allow evaluation of changes after baseline. No safety data were formally analyzed.

taining [$^{14}$C]XL184 (100 µCi) to the healthy male subjects is presented in the following table.

Summary (mean±SD and % CV) of cumulative recovery of total radioactivity (as percent of dose) in urine and feces following a single 175 mg oral administration of XL184 (L-malate salt) containing [$^{14}$C]XL184 (100 µCi) to healthy male subjects as shown below in Table 6.

TABLE 6

Cumulative recovery of total radioactivity.
Cumulative Recovery of Total Radioactivity
(as Percent of Dose) (n = 8)

| Urine | Feces | Total |
|---|---|---|
| 27.29 ± 4.65 (17%) | 53.79 ± 4.52 (8%) | 81.09 ± 1.56 (2%) |

The mean recovery of radioactivity of 81.09% was achieved within 48 days, and the radioactivity was mainly eliminated in feces (53.79%) and the remainder in urine (27.29%). Less than 1% total mean radioactivity was recovered in feces and urine after Day 28 post dose.

Radioactivity in Plasma and Whole Blood

A summary of plasma and whole blood pharmacokinetic parameters for total radioactivity following a single 175 mg oral administration of XL184 (L-malate salt) containing [$^{14}$C]XL184 (100 µCi)) to healthy male subjects is presented in the following table.

Summary (mean±SD and % CV) of plasma and whole blood pharmacokinetic parameters for total radioactivity following a single 175 mg oral administration of XL184 (L-malate salt) containing [$^{14}$C]XL184 (100 µCi) to healthy male subjects as shown below in Table 7.

TABLE 7

Plasma and whole blood pharmacokinetic parameters for total radioactivity following a single 175 mg oral administration of XL184

| Parameters | Plasma | Whole Blood | % Ratio of Plasma to Whole Blood |
|---|---|---|---|
| $C_{max}$, ngEq/mL | 2000 ± 429 (21) | 1200 ± 243 (20) | 167 ± 12.4 (7) |
| $t_{max}$, h$^a$ | 2.00 (1.00, 4.00) | 2.00 (1.98, 2.00) | NA |
| $AUC_{0-t}$, h · ngEq/mL | 259000 ± 42700 (16) | 54100 ± 10300 (19) | 487 ± 73.3 (15) |
| $AUC_{0-24}$, h · ngEq/mL | 31400 ± 6380 (20) | 19600 ± 3780 (19) | 160 ± 6.65 (4) |
| $AUC_{0-72}$, h · ngEq/mL | 89700 ± 19000 (21) | 54100 ± 10300 (19) | 165 ± 11.1 (7) |
| $AUC_{0-inf}$, h · ngEq/mL | 306000 ± 59500 (19) | NR | NA |
| $k_{el}$, l/h | 0.00308 ± 0.00182 (59) | NR | NA |
| $t_{1/2}$, h | 269 ± 93.2 (35) | NR | NA |

$^a$median (range); NR: Not Reportable (since $AUC_{0-t}/AUC_{0-inf}$ ratio < 0.80); NA: Not Applicable $C_{max}$, maximum observed concentration; $T_{max}$, time of the maximum concentration; $AUC_{0-t}$, area under the concentration-time curve from time zero to the time of the last measurable concentration; $AUC_{0-24}$, area under the concentration-time curve from time zero to 24 hours post XL184 dose; $AUC_{0-72}$, area under the concentration-time curve from time zero to 72 hours post XL184 dose; $AUC_{0-inf}$, area under the concentration-time curve from time zero to infinity; ngEq, an equivalent amount of XL184 freebase required to produce a measured or calculated amount of total radioactivity; $k_{el}$, apparent terminal elimination rate constant; $t_{1/2}$, apparent terminal elimination half-life.

No interim analyses were performed.

Summary of Results:

Disposition of Subjects:

Eight subjects were dosed; one subject was followed for 37 days then withdrew consent while seven subjects were followed for 49 days for urine and feces collection, and one of the seven opted for home collection for the final 14 day extension.

Pharmacokinetic Results:

Radioactivity Recovery

A summary of cumulative recovery of total radioactivity (as percent of dose) in the urine and feces following a single 175 mg oral administration of XL184 (L-malate salt) con- Following a single oral dose, the peak radioactivity in plasma and whole blood was achieved at approximately 2 hours (median) with a mean $C_{max}$ of 2000 and 1200 ngEq/mL, respectively. The mean elimination half-life value for the total radioactivity in plasma was 269 hours. The mean values of systemic exposures ($AUC_{0-24}$ and $AUC_{0-72}$) in plasma were around 1.6 times higher than those in whole blood.

Radioactivity present in erythrocytes and whole blood

The percent total mean radioactivity concentration present in erythrocytes relative to whole blood ranged from 0.174±4.51 to 12.3±3.71 within 72 hours after single dosing, indicating that radioactivity was present primarily in plasma and not markedly associated with red blood cells.

Pharmacokinetic parameters of XL184 and its metabolites in plasma

XL184 and metabolites XL184 half-dimer, XL184-N-oxide, XL184-sulfate, and para fluoroaniline (p-FA) were measured in plasma samples from healthy male subjects following a single 175 mg oral administration of XL184 containing [$^{14}$C]XL184 (100 µCi) by a validated LC/MS/MS method. The p-FA concentrations were below the lower limit of quantification at all time points for all subjects. A summary of plasma pharmacokinetic parameters for XL184 and metabolites XL184 half-dimer, XL184-N-oxide, and XL184 sulfate is presented in the following table.

Summary (mean±SD, and % CV) of plasma pharmacokinetic parameters for XL184 and selected metabolites following a single 175 mg oral administration of XL184 (L malate salt) containing [$^{14}$C] XL184 (100 µCi) to healthy male subjects determined by a validated LC/MS/MS method as shown below in Table 8.

were mild in severity (CTCAE grade 1). The exception was one event of treatment related dizziness, which was moderate (CTCAE grade 2) in severity. Most TEAEs (31/36, 86%) resolved within 1 to 3 days.

Apart from the preferred terms 'headache' and 'flatulence,' which were both reported in three (37.5%) subjects, all other preferred terms were reported in only one subject each. Five subjects (62.5%) reported TEAEs that were assessed as related to the study treatment.

There were no clinically significant changes from baseline in any laboratory values. No remarkable on study results were noted for vital signs or ECG evaluations.

Conclusion: Every attempt was made to keep the subjects in the clinic to obtain 90% recovery of the administered radioactivity.

Following oral administration of a single 175 mg dose of XL184 (L-malate salt) containing 100 µCi [$^{14}$C]-XL184, a mean recovery of total radioactivity of 81.09% was achieved within 48 days. Less than 1% total mean radioactivity was recovered in feces and urine after Day 28 post-dose. The

TABLE 8

Plasma pharmacokinetic parameters for XL184 and selected metabolites following a single 175 mg oral administration of XL184

| Parameters | XL184 | XL184-Half-Dimer | XL184-N-Oxide | XL184-Sulfate |
|---|---|---|---|---|
| $C_{max}$, ng/mL | 1250 ± 238 (19) | 52.9 ± 17.3 (33) | 118 ± 33.7 (28) | 236 ± 66.7 (28) |
| $T_{max}$, h$^a$ | 1.49 (1.00, 3.00) | 18.99 (5.00, 24.10) | 13.50 (2.00, 24.30) | 24.00 (3.00, 48.00) |
| $AUC_{0-24}$, h · ng/mL | 14300 ± 2600 (18) | 1080 ± 341 (32) | 2030 ± 682 (34) | 3970 ± 1350 (34) |
| $AUC_{0-72}$, h · ng/mL | 35000 ± 6770 (19) | 3120 ± 976 (31) | 5610 ± 1940 (35) | 12600 ± 4180 (33) |
| $AUC_{0-t}$, h · ng/mL | 67200 ± 6880 (10) | 6540 ± 1680 (26) | 10100 ± 3210 (32) | 28900 ± 10700 (37) |
| Ratio $^b$, % | NA | 9.93 ± 3.20 (32) | 15.0 ± 3.80 (25) | 42.9 ± 14.4 (33) |
| Ratio $^c$, % | 60.2 ± 7.05 (12) | 5.97 ± 1.91 (32) | 8.82 ± 1.48 (17) | 25.0 ± 6.60 (26) |
| $AUC_{0-inf}$, h · ng/mL | 68000 ± 6910 (10) | 6770 ± 1700 (25) | 10300 ± 3170 (31) | 29500 ± 10600 (36) |
| $k_{el}$, l/h | 0.00712 ± 0.00176 (25) | 0.00807 ± 0.00218 (27) | 0.00846 ± 0.00256 (30) | 0.00859 ± 0.0022 (26) |
| $t_{1/2}$, h | 102 ± 23.3 (23) | 91.8 ± 25.4 (28) | 89.2 ± 29.2 (33) | 86.0 ± 24.3 (28) |

$^a$median (range);
$^b$ratio of $AUC_{0-t}$ (metabolite)/$AUC_{0-t}$ (parent);
$^c$ratio of $AUC_{0-t}$ (each analyte)/$AUC_{0-t}$ (parent + 3 measured metabolites); NA: Not Applicable;

$C_{max}$, maximum observed concentration; $T_{max}$, time of the maximum concentration; $AUC_{0-t}$, area under the concentration-time curve from time zero to the time of the last measurable concentration; $AUC_{0-24}$, area under the concentration-time curve from time zero to 24 hours post XL184 dose; $AUC_{0-72}$, area under the concentration-time curve from time zero to 72 hours post XL184 dose; $AUC_{0-inf}$, area under the concentration-time curve from time zero to infinity; $k_{el}$, apparent terminal elimination rate constant; $t_{1/2}$, apparent terminal elimination half-life.

The main circulating compound in plasma was XL184, which was rapidly absorbed after oral administration and eliminated relatively slowly. Following a single oral dose, the mean peak concentrations of XL184, XL184-half-dimer, XL184-N-oxide, and XL184-sulfate in plasma were achieved at approximately 1.49, 18.99, 13.50, and 24.00 hours (median) with a mean $C_{max}$ of 1250, 52.9, 118 and 236 ng/mL, respectively. The mean estimated elimination half-lives of XL184, XL184-half-dimer, XL184-N-oxide, and XL184-sulfate were 102, 91.8, 89.2, and 86.0 hours, respectively.

For metabolites XL184-half-dimer, XL184-N-oxide, and XL184-sulfate, the mean metabolite exposure ratios relative to parent XL184 (AUC0-t (metabolite)/AUC0-t (parent)) were 9.93%, 15.0%, and 42.9%, respectively. Mean exposure ratios for parent and metabolites XL184 half dimer, XL184-N-oxide and XL184-sulfate relative to total exposure (AUC0-t (each analyte)/AUC0-t (parent+3 measured metabolites)) were 60.2% 5.97%, 8.82%, and 25.0%, respectively.

Safety Results:

There were no deaths, other SAEs, discontinuations due to AEs, or other significant AEs reported during the study. No subject vomited within 4 hours of dosing. Six subjects (75%) reported a total of 36 TEAEs, the majority of which radioactivity was mainly eliminated in feces: (53.79%) and the remainder in urine (27.29%). The peak radioactivity in plasma and whole blood was achieved at approximately 2 hours (median) with a mean $C_{max}$ of 2000 and 1200 ngEq/mL, respectively. The elimination half life of the total radioactivity in plasma was determined with a mean value of 269 hours. The mean values of systemic exposures ($AUC_{0-24}$ and $AUC_{0-72}$) in plasma were around 1.6 times higher than those in whole blood. The mean percent total radioactivity concentrations associated with erythrocytes relative to whole blood indicated that radioactivity was present primarily in plasma and not markedly associated with red blood cells.

The main circulating compound in plasma was XL184, which was rapidly absorbed after oral administration and eliminated relatively slowly. Following a single oral dose, the mean peak concentrations of XL184 and metabolites XL184-half-dimer, XL184-N-oxide, and XL184 sulfate in plasma were achieved at approximately 1.49, 18.99, 13.50, and 24.00 hours (median) with a mean $C_{max}$ of 1250, 52.9, 118, and 236 ng/mL, respectively; the mean estimated elimination half-lives were 102, 91.8, 89.2, and 86.0 hours, respectively.

For metabolites XL184-half-dimer, XL184-N-oxide, and XL184-sulfate, the mean metabolite exposure ratios relative to parent XL184 (AUC0-t (metabolite)/AUC0-t (parent)) were 9.93%, 15.0%, and 42.9%, respectively. Mean exposure ratios for parent and metabolites XL184 half dimer, XL184-N-oxide, and XL184-sulfate relative to total exposure (AUC0-t (each analyte)/AUC0-t (parent+3 measured metabolites)) were 60.2%, 5.97%, 8.82%, and 25.0%, respectively.

The treatment was well tolerated. There were no deaths, other SAEs, discontinuations due to AEs, or other significant AEs. Six subjects (75%) reported a total of 36 TEAEs, the majority of which were mild in severity (CTCAE grade 1); none were severe. Apart from the preferred terms 'headache' and 'flatulence,' which were both reported in three (37.5%) subjects, all other preferred terms were reported in only one subject each. Most TEAEs were transient and resolved within 1 to 3 days. There were no notable clinical laboratory findings, or other safety concerns.

Embodiments

The invention is further defined by the following non-limiting embodiments.

Embodiment 1. A liquid pharmaceutical formulation comprising a compound of formula I:

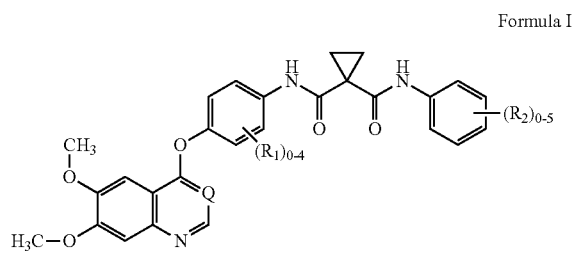

Formula I or a pharmaceutically acceptable salt thereof, and a pharmaceutically acceptable excipient, wherein:
$R^1$ is halo;
$R^2$ is halo; and
Q is CH or N.

Embodiment 2. The liquid pharmaceutical composition according to embodiment 1, wherein the compound of formula I is compound 1, or a pharmaceutically acceptable salt thereof.

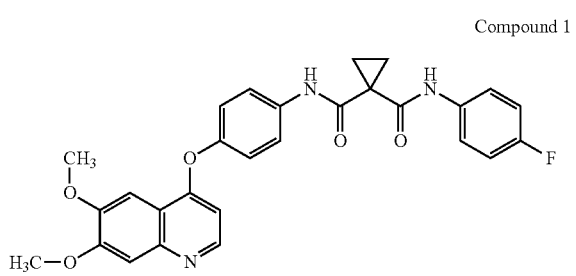 [SMILES: COc1cc2nccc(Oc3ccc(NC(=O)C4(C(=O)Nc5ccc(F)cc5)CC4)cc3)c2cc1OC]

Compound 1

Embodiment 3. The liquid pharmaceutical composition according to embodiment 2, wherein compound 1 is the L-malate salt (or S-malate salt).

Embodiment 4. The liquid pharmaceutical composition according to embodiment 2, wherein compound 1 is the D-malate salt (or R-malate salt).

Embodiment 5. The liquid formulation composition according to any one of embodiments 1-4, wherein the amount of the compound of Formula I or compound 1, or a pharmaceutically acceptable salt thereof present in the liquid formulation, ranges from about 1 mg to about 200 mg.

Embodiment 6. The liquid pharmaceutical composition according to embodiment 5, wherein the amount of the compound of Formula I or compound 1, or a pharmaceutically acceptable salt thereof present in the liquid formulation is about 60 mg, or about 40 mg, or about 20 mg of the compound of formula I or compound 1, or a pharmaceutically acceptable salt thereof.

Embodiment 7. The liquid pharmaceutical composition according to embodiment 1, wherein the liquid formulation provides a smaller inter-subject variability in exposure (% CV of about 10% for $AUC_{0-t}$ and $AUC_{0-inf}$; reference: Lacy et al, 2015 DMD 43:1190-1207) relative to the tablet formulation ((% CV of about 44% for $AUC_{0-t}$ and about 46% for $AUC_{0-inf}$; reference: Nguyen et al, 2016 Anticancer Drugs 27:669-78) upon administration of a single dose of the liquid pharmaceutical composition.

Embodiment 8. A method of treating locally advanced or metastatic solid tumors, comprising administering a patient in need of such treatment, a liquid pharmaceutical composition comprising a compound of formula I:

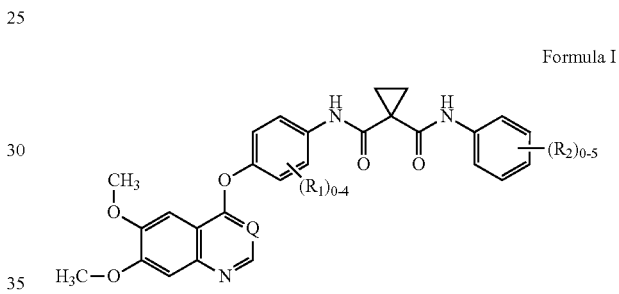

Formula I or a pharmaceutically acceptable salt thereof or a liquid pharmaceutical composition comprising the compound of formula I or the pharmaceutically acceptable salt thereof, and a pharmaceutically acceptable carrier, wherein:
$R^1$ is halo;
$R^2$ is halo; and
Q is CH or N,
and wherein administration of a single dose of the liquid pharmaceutical composition to the patient, provides a smaller inter-subject variability in exposure (% CV of about 10% for $AUC_{0-t}$ and $AUC_{0-inf}$s; reference: Lacy et al, 2015 DMD 43:1190-1207) relative to the tablet formulation ((% CV of about 44% for $AUC_{0-t}$ and about 46% for $AUC_{0-inf}$; reference: Nguyen et al, 2016 Anticancer Drugs 27:669-78).

Embodiment 9. The method according to embodiment 8, wherein the compound of formula I is compound 1, or a pharmaceutically acceptable salt thereof.

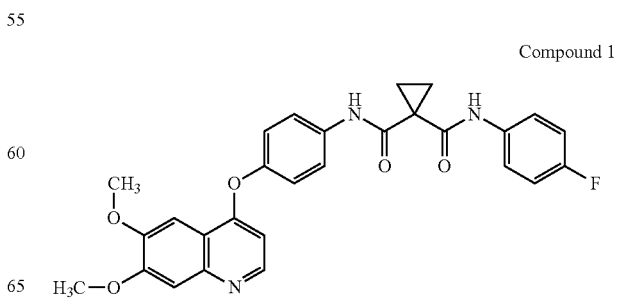

Compound 1

Embodiment 10. The method according to embodiment 9, wherein compound 1 is administered as the L-malate salt (or S-malate salt).

Embodiment 11. The method according to embodiment 9, wherein compound 1 is administered as the D-malate salt (or R-malate salt).

Embodiment 12. The method according to any one of embodiments 8-11, wherein the locally advanced or metastatic solid tumors is advanced UC or RCC.

Embodiment 13. The method according to embodiment 9, wherein compound 1, or a pharmaceutically acceptable salt thereof is administered to the patient in a liquid pharmaceutical composition once daily with fasting in an amount of 100 mg, 95 mg, 90 mg, 85 mg, 80 mg, 75 mg, 70 mg, 65 mg, 60 mg, 55 mg, 50 mg, 45 mg, 40 mg, 35 mg, 30 mg, 25 mg, 20 mg, 15 mg, 10 mg, or 5 mg.

Embodiment 14. The method according to embodiment 13, wherein compound 1, or a pharmaceutically acceptable salt thereof is administered to the patient in a liquid pharmaceutical composition once daily with fasting in an amount of 60 mg, 40 mg, or 20 mg.

Embodiment 15. The method according to any one of embodiments 9-14, wherein a complete serological response is observed in patients being treated with the liquid pharmaceutical composition comprising compound 1, or a pharmaceutically acceptable salt thereof.

Embodiment 16. The method according to any one of embodiments 9-14, wherein a serological partial response is observed in patients being treated with compound 1, or a pharmaceutically acceptable salt thereof.

Embodiment 17. The method according to any one of embodiments 9-14, wherein stable disease is observed in patients being treated with compound 1, or a pharmaceutically acceptable salt thereof.

Preparation of Compound 1

Preparation of 1-(4-Fluorophenylcarbamoyl)cyclopropanecarboxylic acid (Compound A-1)

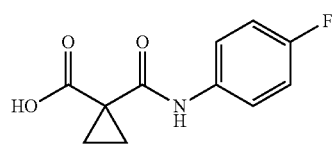 [SMILES: O=C(O)C1(C(=O)Nc2ccc(F)cc2)CC1]

The starting 1,1-cyclopropanedicarboxylic acid was treated with thionyl chloride (1.05 equivalents) in approximately 8 volumes of isopropyl acetate at 25° C. for 5 hours. The resulting mixture was then treated with a solution of 4-fluoroaniline (1.1 equivalents) and triethylamine (1.1 equivalents) in isopropyl acetate (2 volumes) over 1 hour. The product slurry was quenched with 5N NaOH solution (5 volumes), and the aqueous phase was discarded. The organic phase was extracted with 0.5N NaOH solution (10 volumes), and the basic extract was washed with heptane (5 volumes) and subsequently acidified with 30% HCl solution to give a slurry. Compound A-1 was isolated by filtration.

Compound A-1 was prepared on a 1.00 kg scale using 1,1-cyclopropanedicarboxylic acid as the limiting reagent to furnish 1.32 kg of Compound A-1 (77% isolated yield; 84% mass balance) with 99.92% purity (HPLC) and 100.3% assay.

Preparation of N-(4-{[6,7-bis(methyloxy)quinolin-4-yl]oxy}phenyl)-N'-(4-fluorophenyl)cyclopropane-1,1-dicarboxamide (Compound 1) and the (L)-Malate Salt Thereof A synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 1.

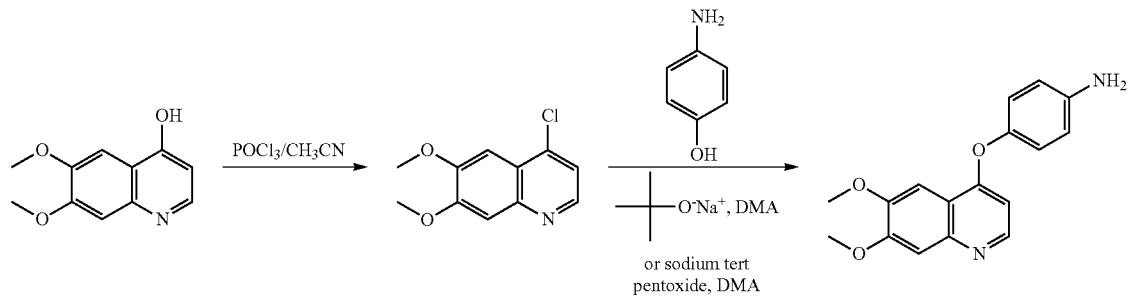

Scheme 1

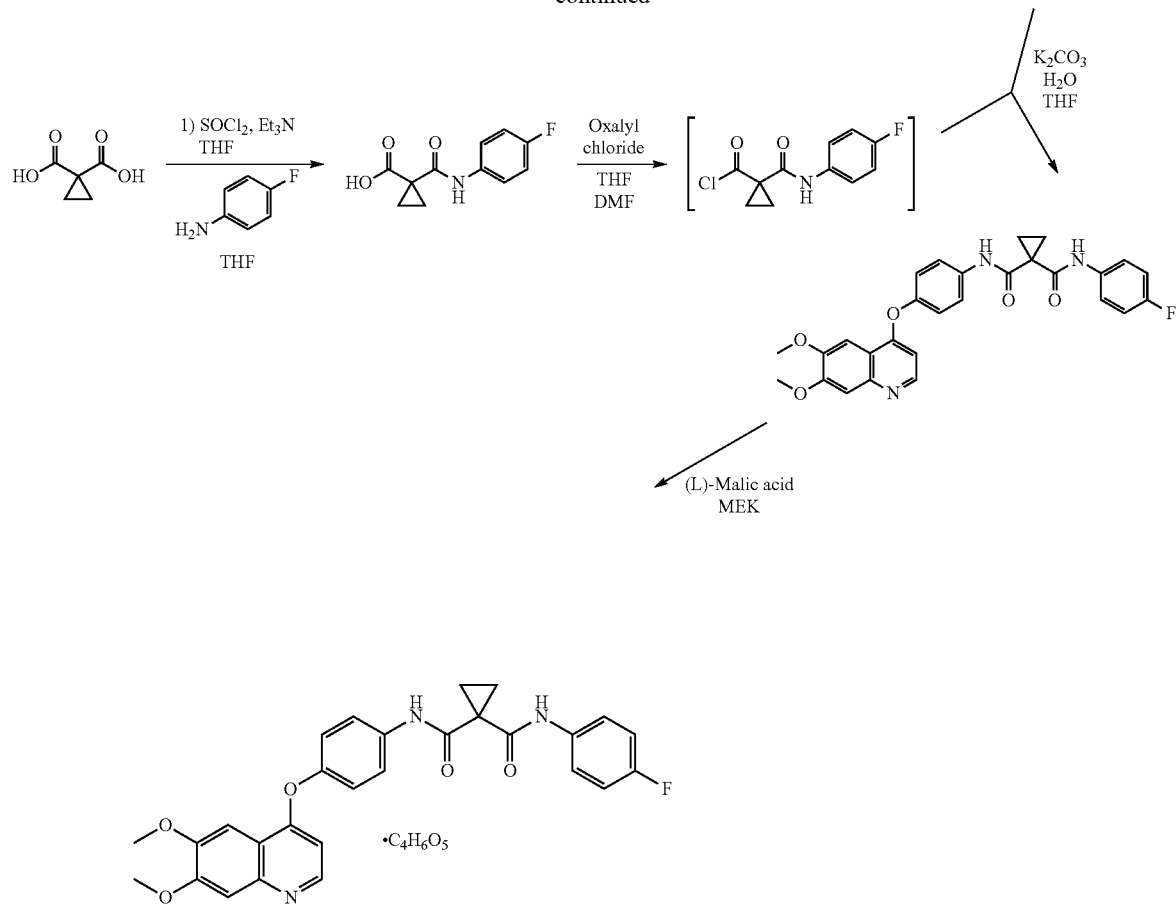
Another synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 2.
Scheme 2
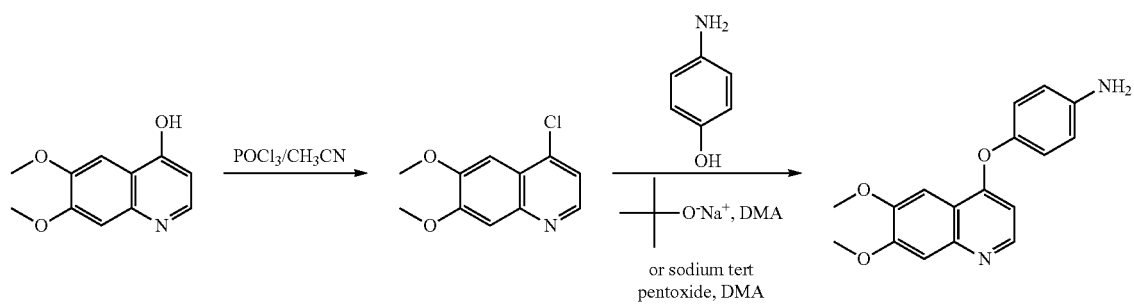

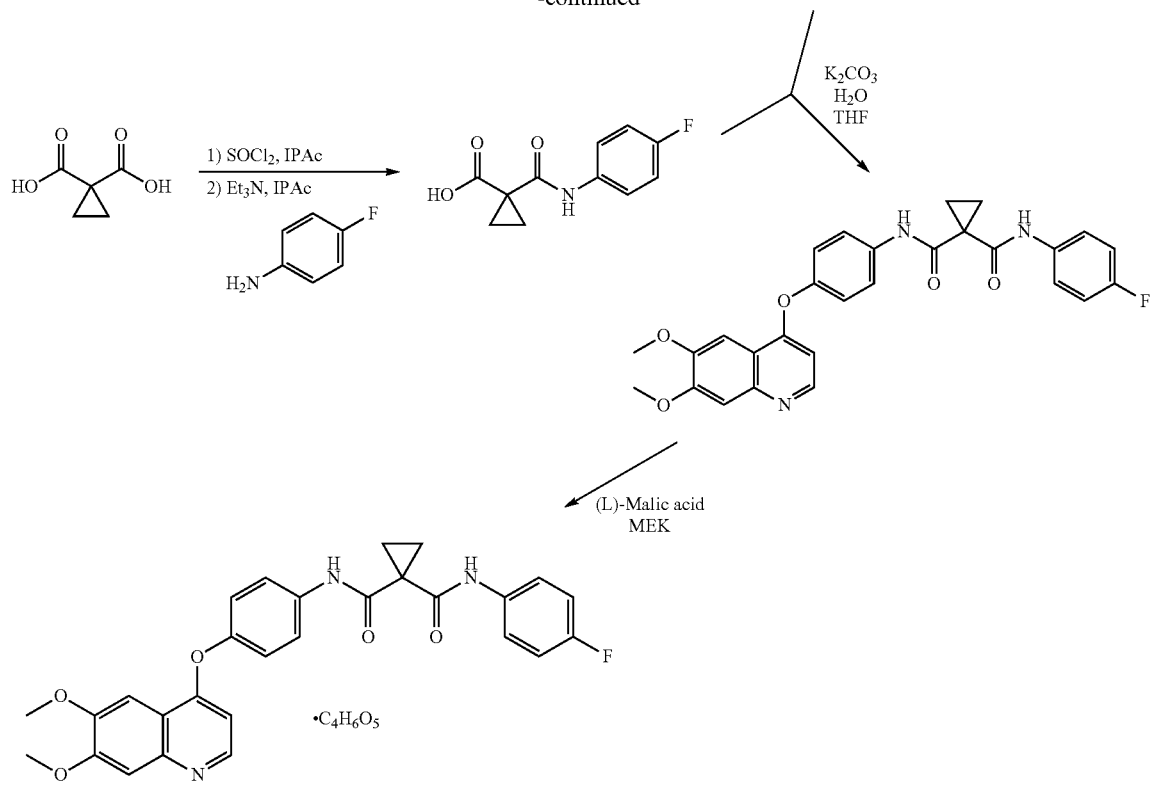

Preparation of 4-Chloro-6,7-dimethoxy-quinolone

A reactor was charged sequentially with 6,7-dimethoxy-quinoline-4-ol (47.0 kg) and acetonitrile (318.8 kg). The resulting mixture was heated to approximately 60° C., and phosphorus oxychloride (POCl$_3$, 130.6 kg) was added. After the addition of POCl$_3$, the temperature of the reaction mixture was raised to approximately 77° C. The reaction was deemed complete (approximately 13 hours) when less than 3% of the starting material remained, as measured by in-process high-performance liquid chromatography [HPLC] analysis. The reaction mixture was cooled to approximately 2 to 7° C. and then quenched into a chilled solution of dichloromethane (DCM, 482.8 kg), 26% NH$_4$OH (251.3 kg), and water (900 L). The resulting mixture was warmed to approximately 20 to 25° C., and phases were separated. The organic phase was filtered through a bed of AW hyflo super-cel NF (Celite; 5.4 kg), and the filter bed was washed with DCM (118.9 kg). The combined organic phase was washed with brine (282.9 kg) and mixed with water (120 L). The phases were separated, and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged, and the temperature of the mixture was adjusted to −20 to −25° C. and held for 2.5 hours resulting in solid precipitate, which was then filtered, washed with n-heptane (92.0 kg), and dried on a filter at approximately 25° C. under nitrogen to afford the title compound (35.6 kg).

Preparation of 4-(6,7-Dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg), and DMA (167.2 kg) at 20-25° C. This mixture was then heated to 100-105° C. for approximately 13 hours. After the reaction was deemed complete as determined using in-process HPLC analysis (less than 2% starting material remaining), the reactor contents were cooled at 15 to 20° C., and water (pre-cooled, 2 to 7° C., 587 L) was charged at a rate to maintain 15 to 30° C. temperature. The resulting solid precipitate was filtered, washed with a mixture of water (47 L) and DMA (89.1 kg), and finally washed with water (214 L). The filter cake was then dried at approximately 25° C. on filter to yield crude 4-(6,7-dimethoxy-quinoline-4-yloxy)-phenylamine (59.4 kg wet, 41.6 kg dry calculated based on LOD). Crude 4-(6,7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour, then cooled to 0 to 5° C., and aged for approximately 1 hour, after which time the solid was filtered, washed with THF (147.6 kg), and dried on a filter under vacuum at approximately 25° C. to yield 4-(6,7-dimethoxy-quinoline-4-yloxy)-phenylamine (34.0 kg).

Alternative Preparation of 4-(6,7-Dimethoxy-quinoline-4-yloxy)-phenylamine 4-chloro-6,7-dimethoxyquinoline (34.8 kg), 4-Aminophenol (30.8 kg), and sodium tert pentoxide (1.8 equivalents) 88.7 kg, 35 weight percent in THF) were charged to a reactor, followed by N,N-dimethylacetamide (DMA, 293.3 kg). This mixture was then heated to 105 to 115° C. for approximately 9 hours. After the reaction was deemed complete as determined using in-process HPLC analysis (less than 2% starting material remaining), the reactor contents were cooled at 15 to 25° C., and water (315 kg) was added over a two hour period while maintaining the temperature between 20 and 30° C. The reaction mixture was then agitated for an additional hour at 20 to 25° C. The crude product was collected by filtration and washed with a mixture of 88 kg water and 82.1 kg DMA, followed by 175 kg water. The product was dried on a filter drier for 53 hours. The LOD showed less than 1% w/w.

In an alternative procedure, 1.6 equivalents of sodium tert-pentoxide were used, and the reaction temperature was increased from 110 to 120° C. In addition, the cool down temperature was increased to 35 to 40° C., and the starting temperature of the water addition was adjusted to 35 to 40° C., with an allowed exotherm to 45° C.

Preparation of
1-(4-Fluoro-phenylcarbamoyl)-cyclopropanecarbonyl
chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N, N-dimethylformamide (DMF; 0.23 kg) at a rate such that the batch temperature did not exceed 25° C. This solution was used in the next step without further processing.

Alternative Preparation of
1-(4-Fluoro-phenylcarbamoyl)-cyclopropanecarbonyl
chloride A reactor was charged with 1-(4-fluoro-phenylcarbamoyl)-cyclopropanecarboxylic acid (35 kg), DMF (344 g), and THF (175 kg). The reaction mixture was adjusted to 12 to 17° C., and then to the reaction mixture was charged 19.9 kg of oxalyl chloride over a period of 1 hour. The reaction mixture was left stirring at 12 to 17° C. for 3 to 8 hours. This solution was used in the next step without further processing.

Preparation of cyclopropane-1,1-dicarboxylic acid
[4-(6,7-dimethoxy-quinoline-4-yloxy)-phenyl]-
amide (4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20 to 25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45° C. under vacuum to afford the title compound (41.0 kg, 38.1 kg, calculated based on LOD).

Alternative Preparation of cyclopropane-1,1-dicar-
boxylic acid [4-(6,7-dimethoxy-quinoline-4-yloxy)-
phenyl]amide (4-fluoro-phenyl)-amide A reactor was charged with 4-(6,7-dimethoxy-quinoline-4-yloxy)-phenylamine (35.7 kg, 1 equivalent), followed by THF (412.9 kg). To the reaction mixture was charged a solution of $K_2CO_3$ (48.3 kg) in water (169 kg). The acid chloride solution of described in the Alternative Preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20 to 30° C. over a minimum of two hours. The reaction mixture was stirred at 20 to 25° C. for a minimum of three hours. The reaction temperature was then adjusted to 30 to 25° C., and the mixture was agitated. The agitation was stopped, and the phases of the mixture were allowed to separate. The lower aqueous phase was removed and discarded. To the remaining upper organic phase was added water (804 kg). The reaction was left stirring at 15 to 25° C. for a minimum of 16 hours.

The product precipitated. The product was filtered and washed with a mixture of water (179 kg) and THF (157.9 kg) in two portions. The crude product was dried under a vacuum for at least two hours. The dried product was then taken up in THF (285.1 kg). The resulting suspension was transferred to reaction vessel and agitated until the suspension became a clear (dissolved) solution, which required heating to 30 to 35° C. for approximately 30 minutes. Water (456 kg) was then added to the solution, as well as SDAG-1 ethanol (20 kg, ethanol denatured with methanol over two hours). The mixture was agitated at 15 to 25° C. for at least 16 hours. The product was filtered and washed with a mixture of water (143 kg and 126.7 kg THF (143 kg) in two portions. The product was dried at a maximum temperature set point of 40° C.

In an alternative procedure, the reaction temperature during acid chloride formation was adjusted to 10 to 15° C. The recrystallization temperature was changed from 15 to 25° C. to 45 to 50° C. for 1 hour and then cooled to 15 to 25° C. over 2 hours.

Preparation of cyclopropane-1,1-dicarboxylic acid
[4-(6,7-dimethoxy-quinoline-4-yloxy)-phenyl]-
amide (4-fluoro-phenyl)-amide, cabozantinib (L)
malate salt Cyclopropane-1,1-dicarboxylic acid [4-(6,7-dimethoxy-quinoline-4-yloxy)-phenyl]-amide (4-fluoro-phenyl)-amide (13.3 kg), L-malic acid (4.96 kg), methyl ethyl ketone (MEK; 188.6 kg) and water (37.3 kg) were charged to a reactor, and the mixture was heated to reflux (approximately 74° C.) for approximately 2 hours. The reactor temperature was reduced to 50 to 55° C., and the reactor contents were filtered. These sequential steps described above were repeated two more times starting with similar amounts of cyclopropane-1,1-dicarboxylic acid [4-(6,7-dimethoxy-qui-noline-4-yloxy)-phenyl]-amide (4-fluoro-phenyl)-amide (13.3 kg), L-Malic acid (4.96 kg), MEK (198.6 kg), and water (37.2 kg). The combined filtrate was azeotropically dried at atmospheric pressure using MEK (1133.2 kg) (approximate residual volume 711 L; KF <0.5% w/w) at approximately 74° C. The temperature of the reactor contents was reduced to 20 to 25° C. and held for approximately 4 hours, resulting in solid precipitate which was filtered, washed with MEK (448 kg), and dried under vacuum at 50° C. to afford the title compound (45.5 kg).

Alternative Preparation of cyclopropane-1,1-dicar-
boxylic acid [4-(6,7-dimethoxy-quinoline-4-yloxy)-
phenyl]amide (4-fluoro-phenyl)-amide, (L) malate
salt Cyclopropane-1,1-dicarboxylic acid [4-(6,7-dimethoxy-quinoline-4-yloxy)-phenyl]-amide (4-fluoro-phenyl)-amide (47.9 kg), L-malic acid (17.2 kg), methyl ethyl ketone (658.2 kg), and water (129.1 kg) were charged to a reactor, and the mixture was heated 50 to 55° C. for approximately 1 to 3 hours and then at 55 to 60° C. for an additional 4 to 5 hours. The mixture was clarified by filtration through a 1 µm cartridge. The reactor temperature was adjusted to 20 to 25° C. and vacuum distilled with a vacuum at 150 to 200 mm Hg with a maximum jacket temperature of 55° C. to the volume range of 558 to 731 L.

The vacuum distillation was performed two more times with the charge of 380 kg and 380.2 kg methyl ethyl ketone, respectively. After the third distillation, the volume of the batch was adjusted to 18 v/w of Cyclopropane-1,1-dicarboxylic acid [4-(6,7-dimethoxy-quinoline-4-yloxy)-phenyl]-amide (4-fluoro-phenyl)-amide by charging methyl ethyl ketone (159.9 kg) to give a total volume of 880 L. An additional vacuum distillation was carried out by adjusting methyl ethyl ketone (245.7 kg). The reaction mixture was left with moderate agitation at 20 to 25° C. for at least 24 hours. The product was filtered and washed with methyl ethyl ketone (415.1 kg) in three portions. The product was dried under a vacuum with the jacket temperature set point at 45° C.

In an alternative procedure, the order of addition was changes so that a solution of L-malic acid (17.7 kg) dissolved in water (129.9 kg) was added to Cyclopropane-1, 1-dicarboxylic acid [4-(6,7-dimethoxy-quinoline-4-yloxy)-phenyl]-amide (4-fluoro-phenyl)-amide (48.7 kg) in methyl ethyl ketone (673.3 kg).

EXAMPLE 1

Phase I Study of Mass Balance Study of Cabozantinib (L-Malate Salt) Following a Single 175 mg Oral Administration of [$^{14}$C]-Cabozantinib (100 µCi) in Healthy Male Subjects 1. Background and Rationale
1.1 Background Multi-targeted tyrosine kinase inhibitors (TKIs) and checkpoint inhibiting immunotherapies represent two systemic modalities that have been instrumental in the recent advancements of anticancer treatment over the past several years. Both classes of therapies have demonstrated broad clinical effects leading to new approved treatment options across multiple tumor types including renal cell carcinoma (RCC), urothelial carcinoma (UC), melanoma, non-small-cell lung cancer (NSCLC), and others. The success of these therapy types as single agents with distinct mechanisms of action has naturally led to interest in evaluating combinations of TKIs with checkpoint inhibitors in search of further, possibly synergistic, anticancer clinical effects.

XL184 is a new chemical entity that inhibits multiple receptor tyrosine kinases implicated in tumor growth and neoangiogenesis. The primary targets of XL184 are hepatocyte growth factor receptor protein (MET), vascular endothelial growth factor receptor 2 (VEGFR2), and rearranged during transfection (RET) proto-oncogene.

XL184 is orally bioavailable as demonstrated by pharmacokinetic (PK) studies in rodent and non-rodent models. In in vivo target modulation studies, administration of XL184 to mice resulted in dose-dependent inhibition of MET, VEGFR2, and RET (Yakes, et al. 2011). Immunohistochemistry studies demonstrate rapid effects on the endothelium, vascular breakdown, and tumor cell death within 24 hours after administration of XL184. This effect translates into significant tumor growth inhibition after XL184 treatment in multiple tumor models. Additionally, in the models tested (human medullary thyroid cancer, human breast cancer, and rat glioma), marked tumor regression was observed.

Clinical activity with the use of XL184 in a variety of tumor settings has been reported and the drug is currently being developed for use in oncology.

1. Introduction

The pharmacokinetic (PK) and statistical analyses of plasma, whole blood, urine and feces concentration, and total radioactivity data were performed and reported in the Clinical Pharmacokinetic Report for the Study XL184-012.

2. Study Objectives

The objectives of the study were:

(1) To determine the time-course for excretion of $^{14}$C radioactivity in urine in healthy male subjects following a single oral dose of the study drug.

(2) To determine the time-course for excretion of $^{14}$C radioactivity in feces in healthy male subjects following a single oral dose of the study drug.

(3) To determine the recovery of $^{14}$C radioactivity as a percentage of administered dose.

(4) To determine the plasma pharmacokinetics (PK) of $^{14}$C radioactivity in healthy male subjects following a single oral dose of the study drug.

(5) To determine the whole blood pharmacokinetics (PK) of $^{14}$C radioactivity in healthy male subjects following a single oral dose of the study drug.

(6) To determine the percentage of $^{14}$C radioactivity associated with erythrocytes in whole blood over time.

(7) To determine the plasma pharmacokinetics (PK) of XL184 and its metabolites by LC/MS/MS in healthy male subjects following a single oral dose of the study drug.

(8) To determine the urine pharmacokinetics (PK) of XL184 and its metabolites in healthy male subjects using a radio-quantitative method following a single oral dose of the study drug.

(9) To determine the feces pharmacokinetics (PK) of XL184 and its metabolites in healthy male subjects using a radio-quantitative method following a single oral dose of the study drug.

(10) To determine the plasma pharmacokinetics (PK) of XL184 and its metabolites in healthy male subjects using a radio-quantitative method following a single oral dose of the study drug.

3. Investigation Plan
3.1 Summary of Study Design

The clinical phase of the study was conducted from 15 Mar. 2011, through 7 Jun. 2011. This study was designed as an open-label, single-dose, mass balance study conducted in 8 healthy male subjects at one study center in the US. Additional subjects would be enrolled only to replace any dosed subjects who drop out of the study prior to recovery of at least 85% of the radioactive dose in the subject's vomitus, urine, and feces. The primary endpoints of the study were time course for excretion of $^{14}$C radioactivity in urine and feces; the recovered percentage of the total dose of $^{14}$C radioactivity; and the percentage of $^{14}$C radioactivity present as XL184 in plasma and whole blood at selected time points.

Subjects received a single calculated oral dose intended to contain a total of 175 mg of XL184 (L-Malate Salt) containing 100 µCi of $^{14}$C.

3.1.1 Identity of Investigational Product(s)
Name: XL184
Active Compound: XL184
Activity: Cancers
Route of Administration: Oral Dose/Solution: 175 mg XL184 (L-Malate Salt) Containing $^{14}$C XL184 (100 µCi)

3.2 Pharmacokinetic Evaluations and Metabolic Profiling Samples 3.2.1 Blood Sample Collections Plasma Blood samples for plasma for analysis of total radioactivity (10 mL each) and for PK analysis of XL184 and/or metabolite concentrations (3 mL each) were collected pre-dose (within the 15 minutes prior to dose) and at 0.5, 1, 2, 3, 4, 5, 8, 14, 24, 48, 72, 120, 144, 168, 240, 336, 408, 504, and 648 hours post-dose. Blood samples for plasma for possible metabolic profiling (10 mL each) were collected pre-dose (within the 15 minutes prior to dose) and at 0.5, 1, 2, 3, 4, 5, 8, 14, 24, 72, 168, 336, 504, and 648 hours post-dose. Prior to study initiation, the Celerion Scintillation Laboratory and the laboratory performing the XL184/metabolite analysis and metabolic profiling (QPS, LLC) supplied to the Celerion clinic complete written instructions for collection, aliquot volume required for analysis, handling, processing, and shipping (if applicable) of samples. All samples collected for radioactivity analysis were analyzed for total radioactivity.

If radioactivity was present in the plasma samples, individual samples at selected time points were analyzed for XL184 and/or metabolites content and metabolic profiling as determined by the sponsor.

Whole Blood

Blood samples (4 mL) for whole blood analysis of total radioactivity were collected within 15 minutes pre-dose and at 1, 2, 4, 8, 14, 24, and 72 hours post-dose. Prior to study initiation, the Celerion Scintillation Laboratory supplied to the Celerion clinic complete written instructions for collection, handling, and processing of samples. Samples collected were used to determine the percentage of radioactivity associated with erythrocytes in whole blood over time (calculated only for time points that whole blood was collected).

3.2.2 Urine

Urine samples were collected for the analysis of total radioactivity and for possible analysis for XL184 and/or metabolites and possible metabolic profiling. Subjects were asked to empty their bladders within approximately 60 minutes prior to dosing for the pre-dose sample. Samples were collected during the 0 to 8 hours and 8 to 24 hours post-dose intervals, and then continuing in 24-hour intervals through Day 49. For subjects who met early release criteria, sampling could cease upon discharge from the clinic. Six subjects were contained in the clinic through 1152 hours (Day 49). One subject was released from the clinic following the 816 hour interval (Day 35) collection and was allowed to home-collect excreta through 1152 hours. One subject was released from the clinic following the 864 hour interval (Day 37) collection and no longer provided excreta samples.

Urine was refrigerated during the collection intervals. Subjects were instructed to urinate at the end of each collection period, if possible. The total volume collected for each interval was recorded. At the end of each collection interval, the urine was mixed to suspend any sediment and the appropriate aliquots were removed. After preparing the necessary aliquots, the remaining samples were destroyed.

Prior to study initiation, the Celerion Scintillation Laboratory and the laboratory performing the XL184/metabolite analysis and metabolic profiling (QPS, LLC) supplied to the Celerion clinic complete written instructions for collection, aliquot volume required for analysis, handling, processing, and shipping (if applicable) of samples. All samples collected for radioactivity were analyzed. If radioactivity was present in the urine samples, individual samples at selected time points might be analyzed for XL184 and/or metabolites content and metabolic profiling as determined by the sponsor.

3.2.3 Feces

Subjects were asked to bring a pre-dose stool sample with them at check-in (produced within 24 hours of check-in). Stools produced between subject check-in and dosing were collected for the pre-dose sample as well, and the sample produced nearest to dosing was used as the pre-dose sample. Post-dose stools were collected in 24-hour intervals through the morning of Day 49. For subjects who met early release criteria, sampling could cease upon discharge from the clinic. Six subjects were contained in the clinic through 1152 hours (Day 49). One subject was released from the clinic following the 816 hour interval (Day 35) collection and was allowed to home-collect excreta through 1152 hours. One subject was released from the clinic following the 864 hour interval (Day 37) collection and no longer provided excreta samples.

For each subject, multiple fecal specimens from each 24-hour interval were combined into a pre-weighed wide mouth polypropylene/polyethylene container and appropriately labeled. For each interval, the fecal sample was weighed to determine the final fecal weight. Each sample was homogenized into a slurry (approximately 20% suspension in water) from which the necessary aliquots were taken.

Prior to study initiation, the Celerion Scintillation Laboratory and the laboratory performing the XL184/metabolite analysis and metabolic profiling (QPS, LLC) supplied to the Celerion clinic complete written instructions for collection, aliquot volume required for analysis, handling, processing, and shipping (if applicable) of samples. All samples collected for radioactivity were analyzed. If radioactivity was present in the fecal samples, individual samples at selected time points might have been analyzed for XL184 and/or metabolites content and metabolic profiling as determined by the sponsor.

3.2.4 Emesis

If emesis occurred within 4 hours following dosing, it was collected (if possible) and stored for potential scintillation counting. The vomitus should have been weighed (the weight recorded in the CRF); labeled with subject number, time, and date; and placed in a freezer set at −20° C.±10° C. until it could be analyzed for radioactivity.

If emesis occurred within 4 hours of dose administration, the subject was replaced and no re-dosing of the same subject was permitted. If radioactivity recovered in vomitus in such subject was ≥85% of total administered radioactivity, the subject would have been discharged. However, if radioactivity recovered in vomitus was <85% of total administered radioactivity, the radioactivity in urine and feces produced by this subject might have been measured and monitored throughout the study upon discretion of the sponsor. A new subject might have been enrolled in the study to replace such a subject.

3.3 Drug Concentration Measurements 3.3.1 Scintillation Counting

The Celerion Scintillation Laboratory, 621 Rose Street, Lincoln, Nebr., performed sample analysis for radioactivity. All analyses were conducted in accordance with GLP.

Individual dosing containers (including the dosage form) were analyzed pre-dose and post-dose for radioactivity, with the (post-dose−pre-dose) difference being the administered dose. Whole blood, plasma, urine, feces, and emesis (if applicable) were analyzed for radioactivity content by liquid scintillation counting procedures. Whole blood and fecal samples were dried and oxidized prior to counting. Detailed reports of scintillation counting method and results for total radioactivity accompany the clinical study report.

3.3.2 Liquid Chromatography-Mass Spectrometry/Mass Spectrometry (LC-MS/MS) and Radio-Quantitative Method for XL184 and/or Metabolite Content Plasma concentrations of XL184 and metabolites XL184-Half-Dimer, XL184-N-Oxide, and XL184-Sulfate were measured using a validated LC/MS/MS method by QPS, LLC, 3 Innovation Way, Suite 240, Newark, Del. 19711, USA. Detailed reports of the bioanalytical methodologies and results accompany the clinical study report. Analyses of XL184 and metabolites XL184-Half-Dimer, XL184-N-Oxide, and XL184-Sulfate were conducted in accordance with GLP. However, the newly identified metabolite, 6-Demethyl Half-Dimer Sulfate, was measured using a non-validated method by QPS, LLC and was not conducted in accordance with GLP.

The other minor metabolite in plasma, p-Fluoroaniline, was analyzed by Exelixis using a validated LC/MS/MS method. The values of p-Fluoroaniline concentrations for all the plasma samples were below the lower limit of quantitation (2.0 ng/mL). Therefore, no data will be listed for p-Fluoroaniline concentrations in this study report.

The newly identified metabolite, 6-Demethyl Half-Dimer Sulfate, was measured using non-validated method by QPS, LLC.

In addition, the plasma concentration of XL184 and metabolites XL184-Half-Dimer, XL184-N-Oxide, XL184-Sulfate, 6-Demethyl Half-Dimer Sulfate, P5, P2, and P7 were determined using a non-GLP radio-quantitative method by QPS, LLC, 3 Innovation Way, Suite 240, Newark, Del. 19711, USA. Detailed reports of the radio-quantitative method and results can be found in the DMPK report.

3.4 Pharmacokinetic Parameters Estimation 3.4.1 Mass Balance and Blood-to-Plasma Distribution Mass balance was calculated as the percent of total administered radioactivity recovered in urine and feces. For the purpose of calculating mass balance, the amount of administered radioactivity was defined as the total radioactivity in the dosing solution minus any radioactivity lost due to emesis (if any occurred), adsorption to the dosing cup, etc.

To determine the percentage of radioactivity associated with erythrocytes in whole blood over time (calculated only for time points where whole blood was collected), the following was calculated: the amount of radioactivity in plasma versus whole blood, adjusted for the hematocrit, at the specific time points of comparison (ETR=Xe/Xb=1−[Cp*(1-Hct)/Cb], where Cp stands for amount of radioactivity in plasma and Cb stands for the amount of radioactivity in blood and Hct stands for hematocrit value. Hematocrit values for Days-1, 2, and 4 were averaged for use in this calculation.

3.4.2 Plasma and Whole Blood

As appropriate, the PK parameters were calculated as data allowed for XL184 and/or metabolite concentrations in plasma and for radioactivity in plasma and whole blood (i.e., nanogram equivalents from radioactivity) using noncompartmental approaches. PK variables were computed using WinNonlin Professional, version 5.2. The definition for each PK variable is listed in the following table. Actual elapsed sampling times relative to [$^{14}$C]-XL184 (100 µCi) oral administration were used for the estimation of PK metrics.

TABLE 9

PK Variable Definitions.

| | |
|---|---|
| $C_{max}$ | Maximum observed concentration |
| $t_{max}$ | Time of the maximum concentration |
| $AUC_{0-t}$ | Area under the concentration-time curve calculated using linear trapezoidal summation from time zero to time t, where t was the time of the last measurable concentration ($C_t$) |
| $AUC_{0-24}$ | Area under the concentration-time curve calculated using linear trapezoidal summation from time zero to time 24 hours |
| $AUC_{0-72}$ | Area under the concentration-time curve calculated using linear trapezoidal summation from time zero to time 72 hours |
| $AUC_{0-inf}$ | Area under the concentration-time curve from time zero to infinity, $AUC_{0-inf} = AUC_{0-t} + C_t/k_{el}$, where $k_{el}$ was the terminal elimination rate constant |
| $k_{el}$ | Apparent terminal elimination rate constant calculated by linear regression of the terminal linear portion of the log concentration vs. time curve |
| $t_{1/2}$ | Apparent terminal elimination half-life calculated as $\ln(2)/k_{el}$ |
| % Ratio of $AUC_{met}/AUC_{XL184}$ | % Ratio of $AUC_{met}/AUC_{XL184}$ = % ($AUC_{0-t}$ of metabolite)/($AUC_{0-t}$ of XL184) |
| % Ratio of $AUC_{analyte}/AUC_{XL184+Metabolites}$ | % Ratio of $AUC_{analyte}/AUC_{XL184+Metabolites}$ = % ($AUC_{0-t}$ of XL184 or metabolite)/($AUC_{0-t}$ of XL184 and metabolites) |

The $C_{max}$ and time to peak concentration ($t_{max}$) were directly determined from the observed blood/plasma concentrations data. $AUC_{0-24}$, $AUC_{0-72}$, and $AUC_{0-t}$, the area under the concentration-time curve from time zero to 24 hours post dose, to 72 hours postdose, and to the time of the last measurable concentration ($C_t$), were calculated using the linear trapezoidal method.

The area under the blood/plasma concentration time curve from time zero to 24 hours postdose, to 72 hours postdose, or up to the last quantifiable concentration ($AUC_{0-t}$) was estimated by numerical integration using the linear trapezoidal rule (Equation 1):

$$AUC_{0-t} = \sum_{i=2}^{n} 0.5 \cdot (C_i + C_{i-1}) \cdot (t_i - t_{i-1}) \qquad \text{Eq. 1}$$

where $C_i$ was the blood/plasma concentration at the corresponding sampling time point of 24, 72 hours or $t_i$, and n was the number of time points up to and including the last quantifiable concentration.

Estimates of half-life ($t_{1/2}$) were calculated using the following (Equation 2):

$$t_{1/2} = \frac{0.693}{k_{el}} \qquad \text{Eq. 2}$$

where the value of the terminal-phase disposition rate constant ($k_{el}$) of the apparent phase were determined by a non-compartmental analysis using WinNonlin. A regression analysis was performed on the terminal linear phase of the semi-logarithmic plots of individual blood/plasma concentration time data. During the analysis, WinNonlin repeated regressions using the last three points with non-zero concentrations, then the last four points, and the last five, etc. Points prior to $C_{max}$ were not used. Points with a value of zero for the dependent variable were excluded. For each regression, an adjusted $R^2$ was computed:

$$\text{Adjusted } R^2 = 1 - (1-R^2)*(n-1)/(n-2) \quad \text{Eq. 3}$$

where n was the number of data points in the regression, and $R^2$ was the square of the correlation coefficient. WinNonlin estimates $k_{el}$ using the regression with the largest adjusted $R^2$, and, if the adjusted $R^2$ did not improve but was within 0.0001 of the largest adjusted $R^2$ value, the regression with the larger number of points was used. $k_{el}$ had to be positive and calculated from at least three data points.

If the terminal phase for any individual subject failed to meet the stated criteria, the $t_{1/2}$ were considered to be not reportable.

The area under the plasma concentration time curve up to time infinity ($AUC_{0-inf}$) was computed using the following (Equation 4):

$$AUC_{0-inf} = AUC_{0-t} + \frac{C_t}{k_{el}} \quad \text{Eq. 4}$$

where $C_t$ was the last measurable concentration.

3.5 Some Data Handling Procedures

If a PK profile did not contain more than five consecutive data points with a quantifiable concentration value, this PK profile was considered not evaluable by the pharmacokineticist.

Only subjects included in the pharmacokinetic analysis were included in the summary statistics.

Below the Quantification Limit (BQL):

Plasma, blood, urine, and feces concentrations below quantifiable limits (BQL) were imputed with a value of zero for the calculation of PK metrics.

The area under the concentration time curve up to time infinity ($AUC_{0-inf}$)

$AUC_{0-inf}$ was considered reportable if the following criteria were met:

$t_{1/2}$ was estimable according to Section [00241].

$AUC_{0-t}/AUC_{0-inf}$ ratio 0.80.

If $AUC_{0-inf}$ for an individual subject fails any of the above criteria, the value was reported as NE or NR, where NE: could not be estimated.

NR: $AUC_{0-t}/AUC_{0-inf}$ ratio <0.80; therefore, $AUC_{0-inf}$ and $t_{1/2}$ were not reportable.

Data Format (Significant Figures and Decimal Points):

Pharmacokinetic parameters were reported to 3 significant figures for individual parameters and summary statistics, with the exception of $t_{max}$ (2 decimal places) and CV % and N, which were whole numbers (0 decimal places).

3.6 Statistical Evaluations of PK Parameters

Descriptive statistics [sample size, mean, standard deviation (SD), standard error of the mean (SEM), minimum, median, maximum, coefficient of variation, and geometric mean] were calculated for those PK parameters identified in the section describing Pharmacokinetic Parameters Estimation. No inferential statistics were calculated.

4. Pharmacokinetics Results 4.1 Data Set Analyzed

Eight subjects were enrolled and completed the study. No subject was withdrawn from the study and experienced the emesis. The statistical analysis population, therefore, consists of 8 subjects.

4.2 Pharmacokinetic Results 4.2.1 Mass Balance Results

The actual total amounts of the dose of XL184 with [$^{14}$C]-radioactivity for individual subjects are listed in Table 10. The individual cumulative percent excretion of [$^{14}$C]-radioactivity in the urine and feces based on total radioactivity after a single oral dose administration of XL184 (L-Malate Salt) containing [$^{14}$C]-XL184 solution in eight healthy male subjects are presented in Table 16 and 17, respectively. The total cumulative percent recoveries of [$^{14}$C]-radioactivity in the urine and feces based on total radioactivity after a single 175 mg oral dose administration of XL184 (L-Malate Salt) containing 100 µCi [$^{14}$C]-XL184 formulated as a solution in eight healthy male subjects is listed in Table 19.

Individual subject urine and feces cumulative excretion of total radioactivity versus time plots following a single 175 mg oral administration of XL184 (L-Malate Salt) containing 100 µCi [$^{14}$C] XL184 was tracked.

Figure 1:
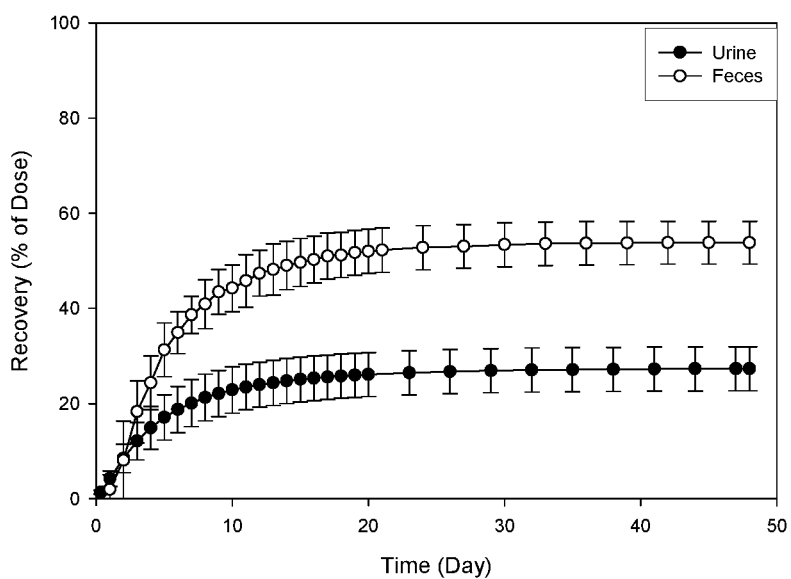
FIG. 1 depicts a line graph of the mean (±SD) cumulative excretion of urine and feces total radioactivity following a single 175 mg oral administration of XL184 (L-malate salt) containing 100 μCi [$^{14}$C] XL184 to healthy male subjects (N=8).

Mean (±SD) cumulative excretion versus time plots of total radioactivity in urine and feces following a single 175 mg oral administration of XL184 (L-Malate Salt) containing 100 µCi [$^{14}$C] XL184 to healthy male subjects are shown in FIG. 1.

TABLE 10

| Dosing Record. | | |
|---|---|---|
| Subject | XL184 (mg) | Total Radioactivity (µCi) |
| 1444-1010 | 192.01 | 104.74 |
| 1444-1023 | 189.97 | 103.63 |
| 1444-1040 | 191.81 | 104.63 |
| 1444-1042 | 189.59 | 103.42 |
| 1444-1051 | 188.35 | 102.74 |
| 1444-1052 | 187.93 | 102.51 |
| 1444-1057 | 188.41 | 102.77 |
| 1444-1058 | 189.57 | 103.41 |

A summary of cumulative recovery of total radioactivity (as percent of dose) in the urine and feces following a single 175 mg oral administration of XL184 (L-Malate Salt) containing 100 µCi [$^{14}$C] XL184 to the healthy male subjects is presented in Table 11.

TABLE 11

Summary (Mean ± SD and % CV) of Cumulative Recovery of Total Radioactivity (as Percent of Dose) in Urine and Feces Following a Single 175 mg Oral Administration of XL184 (L-Malate Salt) containing 100 µCi [$^{14}$C]-XL184 to Healthy Male Subjects.
Cumulative Recovery of Total Radioactivity
(as Percent of Dose) (n = 8)

| Urine | Feces | Total |
|---|---|---|
| 27.29 ± 4.65 (17%) | 53.79 ± 4.52 (8%) | 81.09 ± 1.56 (2%) |

An average 27.29% (ranged from 19.78% to 34.88% based on Table 19) and 53.79% (ranged from 46.54% to 61.89% based on Table 19) of the dose was excreted in the urine and feces following the oral administration of the 175 mg XL184 containing 100 µCi [$^{14}$C]-XL184 to eight male healthy volunteers, respectively. An average of 81.09% (ranged from 78.14% to 83.38% based on Table 19) of the dose was excreted in total in the urine and feces through 48 days post dose. Approximately 1% total mean radioactivity was recovered in feces and urine after Day 28 post-dose. In human radiolabel studies, total cumulative recovery of radioactivity in excreta above 80% may be considered acceptable for mass balance evaluation and sufficient recovery of radioactivity. The total recovery was considered satisfactory (81.09%), with a predominant fecal excretion of 53.79% and urine excretion of 27.29%.

4.2.2 Pharmacokinetic Results 4.2.2.1 Pharmacokinetic Parameters for Total Radioactivity in Plasma and Whole Blood The individual and mean plasma and whole blood concentration data for [$^{14}$C]-radioactivity after single dose administration of 175 mg of XL184 (L-Malate Salt) containing 100 µCi [$^{14}$C]-XL184 formulated as a solution in healthy male subjects are presented in Tables 22 and 23, respectively. The individual and mean hematocrit values are listed in Table 22. The individual and descriptive statistics of the percentage of $^{14}$C radioactivity associated with erythrocytes in whole blood (ETR) over time are included in Table 26. The individual actual blood sampling times of total radioactivity for plasma and whole blood are listed in Table 27.

The individual subject $^{14}$C total radioactivity in plasma and whole blood and plasma XL184 concentration (by LC/MS/MS method) versus time plots following a single 175 mg oral administration of 175 mg of XL184 (L-Malate Salt) containing 100 µCi [$^{14}$C]-XL184 are presented in the figures herein (linear axes) and (semi-logarithmic axes). The individual percentage of $^{14}$C radioactivity associated with erythrocytes in whole blood (ETR) over time graphs following a single oral administration of 175 mg of XL184 (L-Malate Salt) containing 100 µCi [$^{14}$C]-XL184 to healthy male subjects are shown in the figures and tables herein.

The individual subject and descriptive statistics for pharmacokinetic parameters of [$^{14}$C]-radioactivity in plasma and whole blood are included in Table 26 and Table 27, respectively.

WinNonlin outputs of pharmacokinetic analyses of total radioactivity in plasma and whole blood data are included in the Figures and Tables herein.

Figure 2:
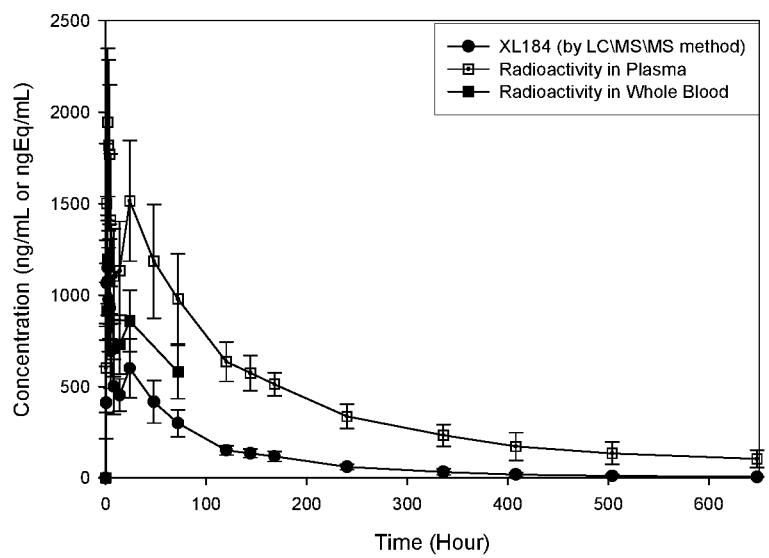
FIG. 2 depicts a line graph of the mean (±SD) plasma total radioactivity in plasma and whole blood and XL184 concentration (by LC/MS/MS method) vs. time 0-648 hours following a single 175 mg oral administration of XL184 (L-malate salt) containing 100 μCi [$^{14}$C] XL184 to healthy male subjects—linear axes (N=8)
Figure 3:
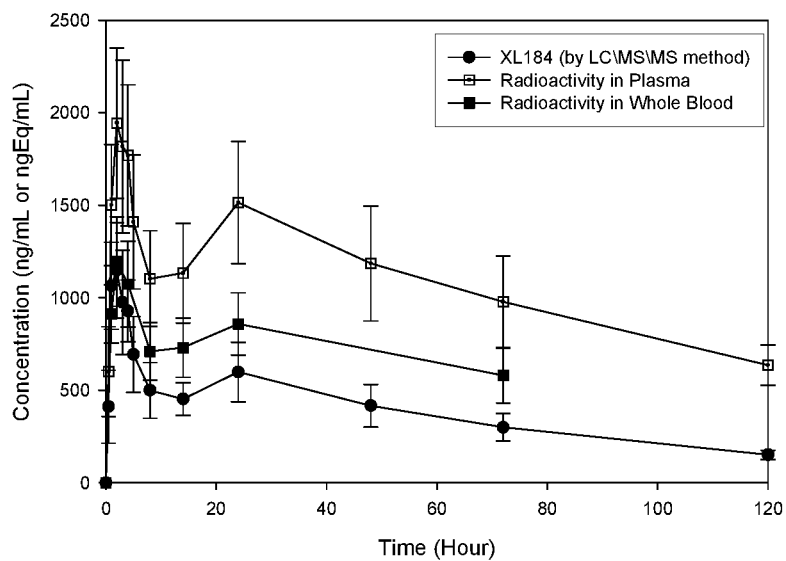
FIG. 3 depicts a line graph of the mean (±SD) plasma total radioactivity in plasma and whole blood and XL184 concentration (by LC/MS/MS method) vs. time 0-120 hours following a single 175 mg oral administration of XL184 (L-malate salt) containing 100 μCi [$^{14}$C] XL184 to healthy male subjects—linear axes (N=8)
Figure 4:
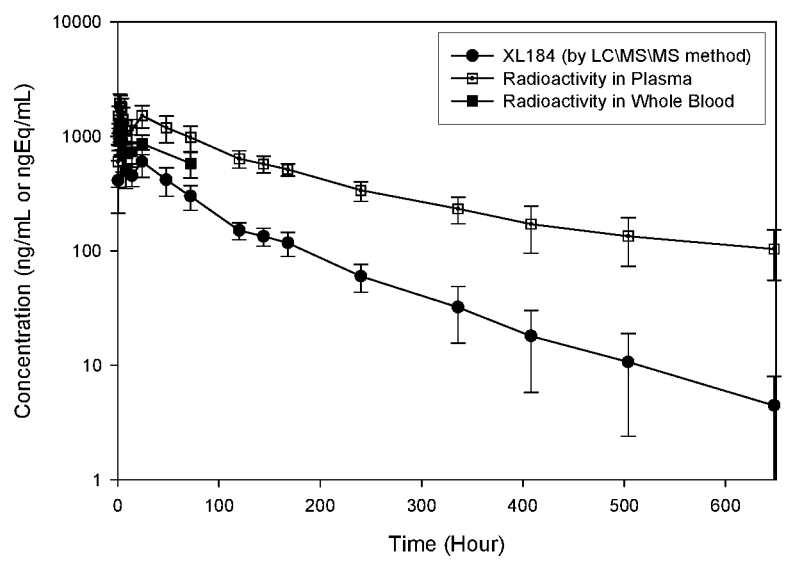
FIG. 4 depicts a line graph of the mean (±SD) plasma total radioactivity in plasma and whole blood and XL184 concentration (by LC/MS/MS method) vs. time 0-648 hours following a single 175 mg oral administration of XL184 (L-malate salt) containing 100 μCi [$^{14}$C] XL184 to healthy male subjects—semilogarithmic axes (N=8).
Figure 5:
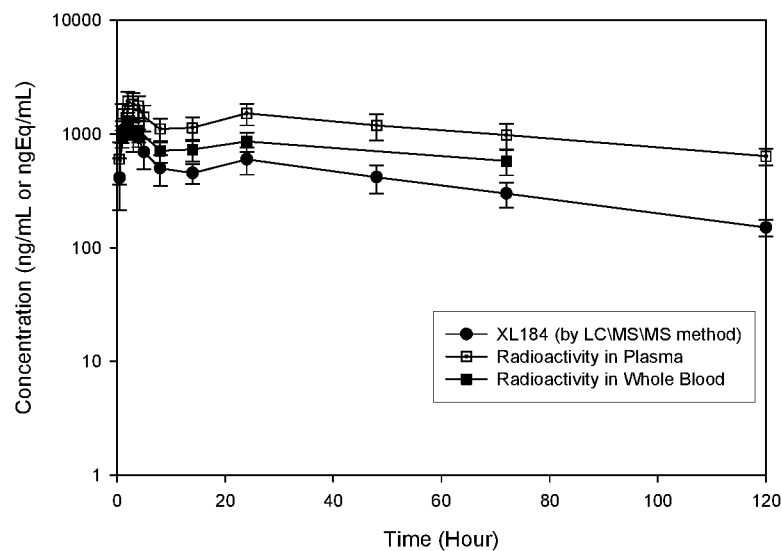
FIG. 5 depicts a line graph of the mean (±SD) plasma total radioactivity in plasma and whole blood and XL184 concentration (by LC/MS/MS method) vs. time 0-120 hours following a single 175 mg oral administration of XL184 (L-malate salt) containing 100 μCi [$^{14}$C] XL184 to healthy male subjects—semilogarithmic axes (N=8).
Figure 6:
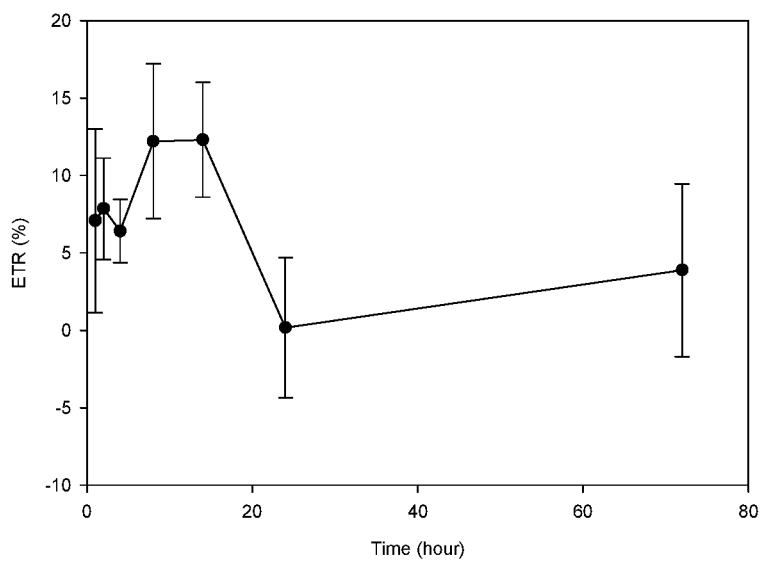
FIG. 6 depicts a line graph of the mean (±SD) percentage of 14C radioactivity associated with erythrocytes in whole blood over time graph following a single 175 mg oral administration of XL184 (L-malate salt) containing 100 μCi [$^{14}$C] XL184 to healthy male subjects (N=8).

FIGS. 2 and 3 (linear axes) and FIGS. 4 and 5 (semi-logarithmic axes) illustrate the mean (±SD) $^{14}$C total radioactivity in plasma and whole blood and plasma XL184 concentration (by LC/MS/MS method) versus time plots after administration of single 175 mg dose of XL184 (L-Malate Salt) containing 100 µCi [$^{14}$C]-XL184 formulated as an oral solution, respectively. FIG. 6 demonstrates the mean (±SD) plots of percentage of $^{14}$C radioactivity associated with erythrocytes in whole blood over time following a single 175 mg oral administration of XL184 (L-Malate Salt) containing 100 µCi [$^{14}$C]-XL184 to healthy male subjects.

A summary of plasma and whole blood pharmacokinetic parameters for total radioactivity following a single 175 mg oral administration of XL184 (L-Malate Salt) containing 100 µCi [$^{14}$C]-XL184 to healthy male subjects is presented in Table 12.

A summary (mean±SD) of the percentage of $^{14}$C radioactivity associated with erythrocytes in whole blood (ETR) over time following a single 175 mg oral administration of XL184 (L-Malate Salt) containing 100 µCi [$^{14}$C]-XL184 to healthy male subjects is presented in Table 13.

Following a single oral dose, the peak radioactivity in plasma and whole blood were achieved at approximately 2 hours (median) with a mean maximum value ($C_{max}$) of 2000 and 1200 ngEq/mL, respectively. The elimination half-life ($t_{1/2}$) of the total radioactivity in plasma was determined with a mean value of 269 hours. However, the $t_{1/2}$, $AUC_{0-inf}$, and $AUC_{0-72}$ of the total radioactivity in whole blood were not reportable since $AUC_{0-t}/AUC_{0-inf}$ ratio were less than 0.80 for those eight subjects. The mean values of systemic exposures ($AUC_{0-24}$ and $AUC_{0-72}$) in plasma were around 1.6 times higher than those in whole blood (Table 12).

TABLE 12

Summary (Mean ± SD and % CV) of Plasma and Whole Blood Pharmacokinetic Parameters for Total Radioactivity following a Single 175 mg Oral Administration of XL184 (L-Malate Salt) containing 100 µCi [$^{14}$C]-XL184 to Healthy Male Subjects.

| Parameters | Plasma | Whole Blood | % Ratio of Plasma to Whole blood |
|---|---|---|---|
| $C_{max}$, ngEq/mL | 2000 ± 429 (21) | 1200 ± 243 (20) | 167 ± 12.4 (7) |
| $t_{max}$, h$^a$ | 2.00 (1.00, 4.00) | 2.00 (1.98, 2.00) | NA |
| $AUC_{0-t}$, h · ngEq/mL | 259000 ± 42700 (16) | 54100 ± 10300 (19) | 487 ± 73.3 (15) |
| $AUC_{0-24}$, h · ngEq/mL | 31400 ± 6380 (20) | 19600 ± 3780 (19) | 160 ± 6.65 (4) |
| $AUC_{0-72}$, h · ngEq/mL | 89700 ± 19000 (21) | 54100 ± 10300 (19) | 165 ± 11.1 (7) |
| $AUC_{0-inf}$, h · ngEq/mL | 306000 ± 59500 (19) | NR | NA |
| $k_{el}$, 1/h | 0.00308 ± 0.00182 (59) | NR | NA |
| $t_{1/2}$, h | 269 ± 93.2 (35) | NR | NA |

$^a$median (range); NR: Not Reportable, since $AUC_{0-t}/AUC_{0-inf}$ ratio < 0.80; NA: Not Applicable;

$C_{max}$, maximum observed concentration; $T_{max}$, time of the maximum concentration; $AUC_{0-t}$, area under the concentration-time curve from time zero to the time of the last measurable concentration; $AUC_{0-24}$, area under the concentration-time curve from time zero to 24 hours post XL184 dose; $AUC_{0-72}$, area under the concentration-time curve from time zero to 72 hours post XL184 dose; $AUC_{0-inf}$, area under the concentration-time curve from time zero to infinity; $k_{el}$, apparent terminal elimination rate constant; $t_{1/2}$, apparent terminal elimination half-life; CL/F, apparent total body clearance; V/F, apparent total volume of distribution; ngEq, an equivalent amount of XL184 freebase required to produce a measured or calculated amount of total radioactivity.

The total radioactivity in whole blood and plasma was detectable in all subjects following single dosing. One of the purposes of this measurement was to characterize the partitioning of [$^{14}$C]-XL184 in erythrocytes and whole blood. Erythrocyte to whole blood concentration ratios were examined after single dosing. The details of calculation used to determine the erythrocyte-to-whole blood total radioactivity concentration ratios are described in Section 3.4.1.

The mean percent of total radioactivity concentrations associated with erythrocytes based on the concentration of total radioactive concentrations in plasma and whole blood ranged from 0.174±4.51 to 12.3±3.71 within 72 hours after single dosing, indicating that radioactivity was present primarily in plasma and not markedly associated with red blood cells (Table 13).

TABLE 13

Summary (Mean ± SD and % CV) of Percentage of $^{14}C$ Radioactivity Associated with Erythrocytes in Whole Blood (ETR) over Time following a Single 175 mg Oral Administration of XL184 (L-Malate Salt) containing 100 µCi [$^{14}C$]-XL184 to Healthy Male Subjects.

| Time (hr) | Percentage (%) |
|---|---|
| 1 | 7.08 ± 5.93 (84) |
| 2 | 7.85 ± 3.27 (42) |
| 4 | 6.40 ± 2.05 (32) |
| 8 | 12.2 ± 5.00 (41) |
| 14 | 12.3 ± 3.71 (30) |
| 24 | 0.174 ± 4.51 (2595) |
| 72 | 3.89 ± 5.58 (143) |

4.2.2.2 Plasma Pharmacokinetic Parameters for XL184 and its Metabolites by LC/MS/MS Method The individual and mean plasma concentration data for XL184 and metabolites XL184-Half-Dimer, XL184-N-Oxide, XL184-Sulfate, and 6-Demethyl Half-Dimer Sulfate by LC/MS/MS method after single dose administration of 175 mg of XL184 (L-Malate Salt) containing 100 µCi [$^{14}C$]-XL184 formulated as an oral solution in healthy male subjects are presented in Tables 28 to 32A. Para-fluoroaniline (pFA) metabolite concentrations were below the LLOQ for all subjects. The individual actual plasma sampling times are listed in Table 23. The individual subject and descriptive statistics plasma pharmacokinetic parameters of XL184 and metabolites XL184-Half-Dimer, XL184-N-Oxide, XL184-Sulfate, and 6-Demethyl Half-Dimer Sulfate by LC/MS/MS method are included in Tables 33 to 36.

Figure 7:
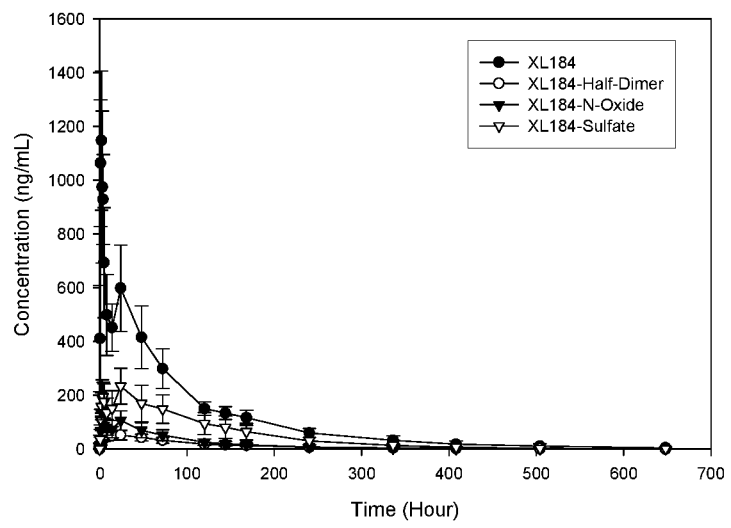
FIG. 7 depicts a line graph of the mean (±SD) plasma concentrations of XL184 and metabolites XL184-half-dimer, XL184-N-oxide, and XL184-sulfate measured by LC/MS/MS method vs. time 0-648 hours following a single 175 mg oral administration of XL184 (L-malate salt) containing 100 μCi [$^{14}$C] XL184 to healthy male subjects—linear axes (N=$^8$).
Figure 8:
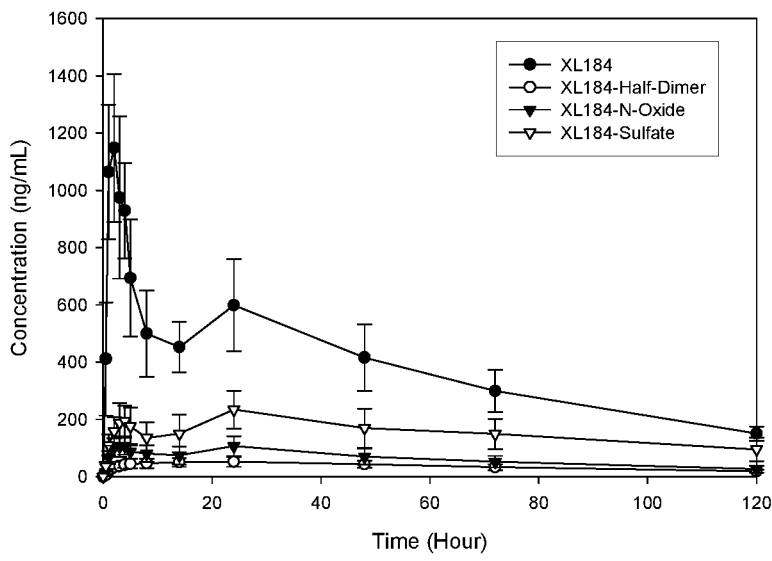
FIG. 8 depicts a line graph of the mean (±SD) plasma concentrations of XL184 and metabolites XL184-half-dimer, XL184-N-oxide, and XL184-sulfate measured by LC/MS/MS method vs. time 0-120 hours following a single 175 mg oral administration of XL184 (L-malate salt) containing 100 μCi [$^{14}$C] XL184 to healthy male subjects—linear axes (N=$^8$).
Figure 9:
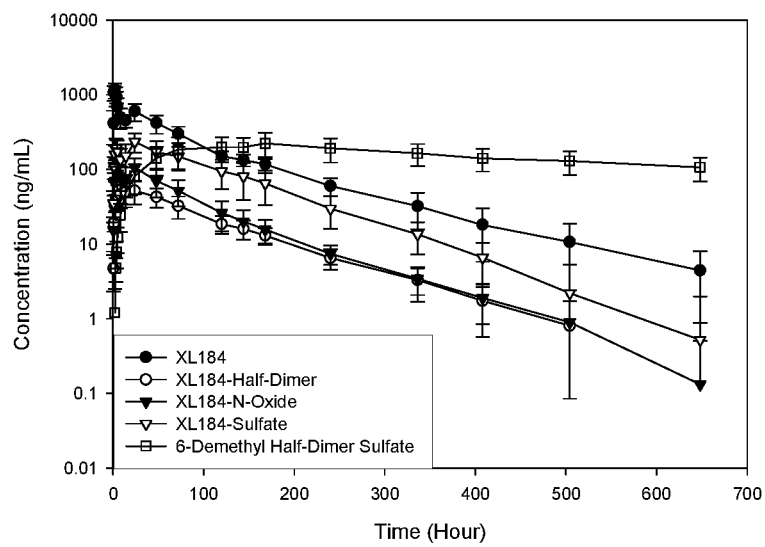
FIG. 9 depicts a line graph of the mean (±SD) plasma concentrations of XL184 and metabolites, XL184-half-dimer, XL184-N-oxide, and XL184-sulfate measured by LC/MS/MS method vs. time 0-648 hours following a single 175 mg oral administration of XL184 (L-malate salt) containing 100 μCi [$^{14}$C] XL184 to healthy male subjects—semilogarithmic axes (N=8).
Figure 10:
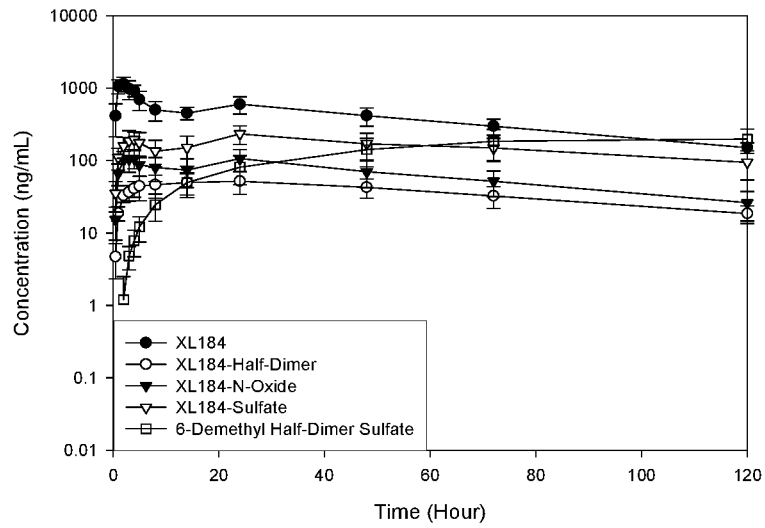
FIG. 10 depicts a line graph of the mean (±SD) plasma concentrations of XL184 and metabolites, XL184-half-dimer, XL184-N-oxide, and XL184-sulfate measured by LC/MS/MS method vs. time 0-120 hours following a single 175 mg oral administration of XL184 (L-malate salt) containing 100 μCi [$^{14}$C] XL184 to healthy male subjects—semilogarithmic axes (N=8).

FIGS. 7 and 8 (linear axes) and FIGS. 9 and 10 (semi-logarithmic axes) illustrate the mean (±SD) plasma concentrations versus time plots of XL184 and metabolites XL184-Half-Dimer, XL184-N-Oxide, XL184-Sulfate, and 6-Demethyl Half-Dimer Sulfate, respectively, measured by LC/MS/MS method after administration of single 175 mg dose of XL184 (L-Malate Salt) containing 100 µCi [$^{14}C$]-XL184 as an oral solution.

A summary of plasma pharmacokinetic parameters of XL184 and metabolites XL184-Half-Dimer, XL184-N-Oxide, XL184-Sulfate, and 6-Demethyl Half-Dimer Sulfate measured by LC/MS/MS method following a single 175 mg oral administration of XL184 (L-Malate Salt) containing 100 µCi [$^{14}C$]-XL184 to healthy male subjects is presented in Table 14.

The parent compound, XL184, was rapidly absorbed after oral administration and eliminated relatively slowly. The main circulating metabolite in plasma was 6-Demethyl Half-Dimer Sulfate. Following a single oral dose, the mean peak concentrations of XL184, XL184-Half-Dimer, XL184-N-Oxide, XL184-Sulfate, and 6-Demethyl Half-Dimer Sulfate in plasma were achieved at approximately 1.49, 18.99, 13.50, 24.00, and 168.00 hours (median) with a mean maximum concentration value ($C_{max}$) of 1250, 52.9, 118, 236 and 230 ng/mL, respectively. The mean estimated elimination half-lives of XL184, XL184-Half-Dimer, XL184-N-Oxide, and XL184-Sulfate were 102, 91.8, 89.2, and 86.0 hours, respectively (FIGS. 7, 8, 9, and 10 and Table 14). However, the elimination half-lives of 6-Demethyl Half-Dimer Sulfate for all the subjects could not be determined.

For metabolites XL184-Half-Dimer, XL184-N-Oxide, XL184-Sulfate, and 6-Demethyl Half-Dimer Sulfate, the mean metabolite exposure ratios relative to parent XL184 ($AUC_{0-t}$ (metabolite)/$AUC_{0-t}$ (parent)) were 9.93%, 15.0%, 42.9%, and 150%, respectively. Mean exposure ratios for parent and metabolites XL184-Half-Dimer, XL184-N-Oxide, XL184-Sulfate, and 6-Demethyl Half-Dimer Sulfate relative to total exposure, ($AUC_{0-t}$ (each analyte)/$AUC_{0-t}$ (parent+4 measured metabolites)) were 32.4%, 3.09%, 4.90%, 13.8%, and 45.9%, respectively.

TABLE 14

Summary (Mean ± SD and % CV) of Plasma Pharmacokinetic Parameters for XL184 and Selected Metabolites by LC/MS/MS Method Following a Single 175 mg Oral Administration of XL184 (L-Malate Salt) Containing [$^{14}C$]-XL184 (100 µCi) to Healthy Male Subjects.

| Parameters | XL184 | XL184-Half-Dimer | XL184-N-Oxide | XL184-Sulfate | 6-Demethyl Half-Dimer Sulfate* |
|---|---|---|---|---|---|
| $C_{max}$, ng/mL | 1250 ± 238 (19)[e] | 52.9 ± 17.3 (33) | 118 ± 33.7 (28) | 236 ± 66.7 (28) | 230 ± 91.2 (40) |
| $T_{max}$, h[a] | 1.49 (1.00, 3.00) | 18.99 (5.00, 24.10) | 13.50 (2.00, 24.30) | 24.00 (3.00, 48.00) | 168.00 (71.97, 240.00) |
| $AUC_{0-24}$, h · ng/mL | 14300 ± 2600 (18) | 1080 ± 341 (32) | 2030 ± 682 (34) | 3970 ± 1350 (34) | 951 ± 377 (40) |
| $AUC_{0-72}$, h · ng/mL | 35000 ± 6770 (19) | 3120 ± 976 (31) | 5610 ± 1940 (35) | 12600 ± 4180 (33) | 7530 ± 3200 (42) |
| $AUC_{0-t}$, h · ng/mL | 67200 ± 6880 (10) | 6540 ± 1680 (26) | 10100 ± 3210 (32) | 28900 ± 10700 (37) | 99500 ± 34500 (35) |
| Ratio [b], % | NA | 9.93 ± 3.20 (32) | 15.0 ± 3.80 (25) | 42.9 ± 14.4 (33) | 150 ± 51.5 (34) |
| Ratio [c], % | 32.4 ± 6.07 (19) | 3.09 ± 0.689 (22) | 4.90 ± 2.01 (41) | 13.8 ± 5.63 (41) | 45.9 ± 11.2 (24) |
| $AUC_{0-inf}$, h · ng/mL | 68000 ± 6910 (10) | 6770 ± 1700 (25) | 10300 ± 3170 (31) | 29500 ± 10600 (36) | NA |
| $k_{el}$, l/h | 0.00712 ± 0.00176 (25) | 0.00807 ± 0.00218 (27) | 0.00846 ± 0.00256 (30) | 0.00859 ± 0.0022 (26) | NA |
| $t_{1/2}$, h | 102 ± 23.3 (23) | 91.8 ± 25.4 (28) | 89.2 ± 29.2 (33) | 86.0 ± 24.3 (28) | NA |

[a] median (range);
[b] ratio of $AUC_{0-t}$ (metabolite)/$AUC_{0-t}$ (parent);
[c] ratio of $AUC_{0-t}$ (each analyte)/$AUC_{0-t}$ (parent + 4 measured metabolites); NA: Not Applicable; $C_{max}$, maximum observed concentration; $T_{max}$, time of the maximum concentration; $AUC_{0-t}$, area under the concentration-time curve from time zero to the time of the last measurable concentration; $AUC_{0-24}$, area under the concentration-time curve from time zero to 24 hours post XL184 dose;
$AUC_{0-72}$, area under the concentration-time curve from time zero to 72 hours post XL184 dose; $AUC_{0-inf}$, area under the concentration-time curve from time zero to infinity; $k_{el}$, apparent terminal elimination rate constant; $t_{1/2}$, apparent terminal elimination half-life;
*The LC/MS/MS analytical method for 6-demethy half-dimer sulfate is not validated.

4.2.2.3 Plasma Pharmacokinetic Parameters for XL184 and its Metabolites using a Radio-Quantitation Method Samples for 2 subjects were used for the investigation study. Therefore, only 6 subjects' PK profiles were determined using a radio-quantitation method. Due to the low radioactivity after 336 hours, the samples for 504 hours and 648 hours were not analyzed. The individual and mean plasma concentration data for XL184 and metabolites XL184-Half-Dimer, XL184-N-Oxide, XL184-Sulfate, 6-Demethyl Half-Dimer Sulfate, P5, P2, and P7 using a radio-quantitative method after single dose administration of 175 mg of XL184 (L-Malate Salt) containing 100 µCi [$^{14}$C]-XL184 formulated as an oral solution in healthy male subjects are presented in Table 15.

Figure 11:
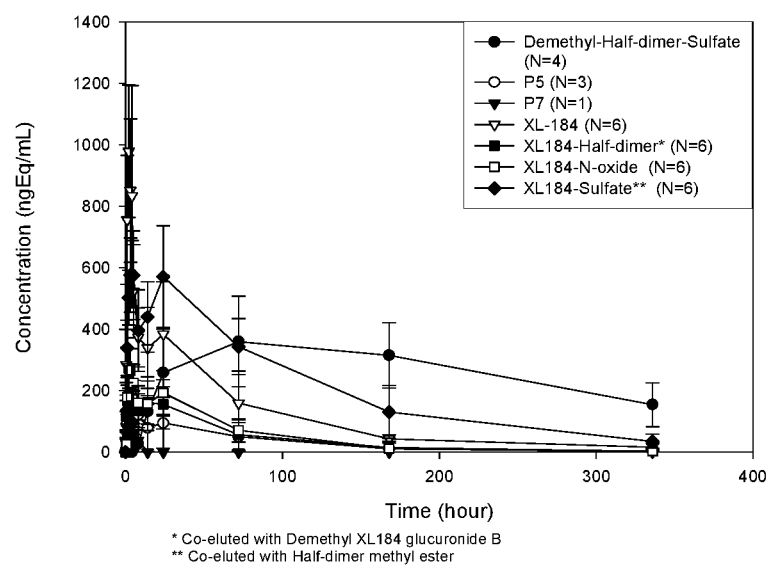
FIG. 11 depicts a line graph of the mean (±SD) plasma concentrations of demethyl half-dimer sulfate, P5, P7, XL-184, XL184-half-dimer, XL184-N-oxide, and XL184-sulfate measured by radio-quantitation method vs. time 0-336 hours following a single 175 mg oral administration of XL184 (L-malate salt) containing 100 μCi [$^{14}$C]-XL184 to healthy male subjects—linear axes.
Figure 12:
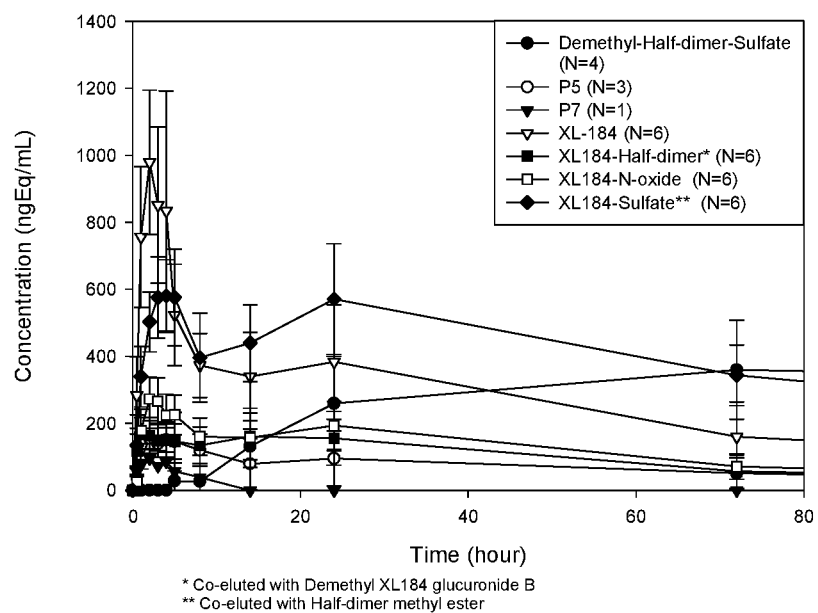
FIG. 12 depicts a line graph of the mean (±SD) plasma concentrations of demethyl half-dimer sulfate, P5, P7, XL-184, XL184-half-dimer, XL184-N-oxide, and XL184- sulfate measured by radio-quantitation method vs. time 0-80 hours following a single 175 mg oral administration of XL184 (L-malate salt) containing 100 µCi [$^{14}$C]-XL184 to healthy male subjects—linear axes.

The individual actual plasma sampling times are listed in Table 23. The individual subject and descriptive statistics plasma pharmacokinetic parameters of XL184 and metabolites XL184-Half-Dimer, XL184-N-Oxide, XL184-Sulfate, 6-Demethyl Half-Dimer Sulfate, P5, P2, and P7 using a radio-quantitative method are included in Table 45. app FIGS. 11 and 12 (linear axes) and FIGS. 13 and 14 (semi-logarithmic axes) illustrate the mean (±SD) plasma concentrations versus time plots of XL184 and metabolites XL184-Half-Dimer, XL184-N-Oxide, XL184-Sulfate, 6-Demethyl Half-Dimer Sulfate, P5, and P7, respectively, measured by a radio-quantitative method after administration of single 175 mg dose of XL184 (L-Malate Salt) containing 100 µCi [$^{14}$C]-XL184 as an oral solution.

A summary of plasma pharmacokinetic parameters of XL184 and metabolites XL184-Half-Dimer, XL184-N-Oxide, XL184-Sulfate, 6-Demethyl Half-Dimer Sulfate, P5, and P7, measured by a radio-quantitative method following a single 175 mg oral administration of XL184 (L-Malate Salt) containing 100 µCi [$^{14}$C]-XL184 to healthy male subjects is presented in Table 15. Since no subjects had more than five consecutive data points with a quantifiable P2 concentration value, there is no pharmacokinetic parameter information included in Table 15. The proposed major biotransformation products of XL184 are displayed in Scheme 3.

Scheme 3.

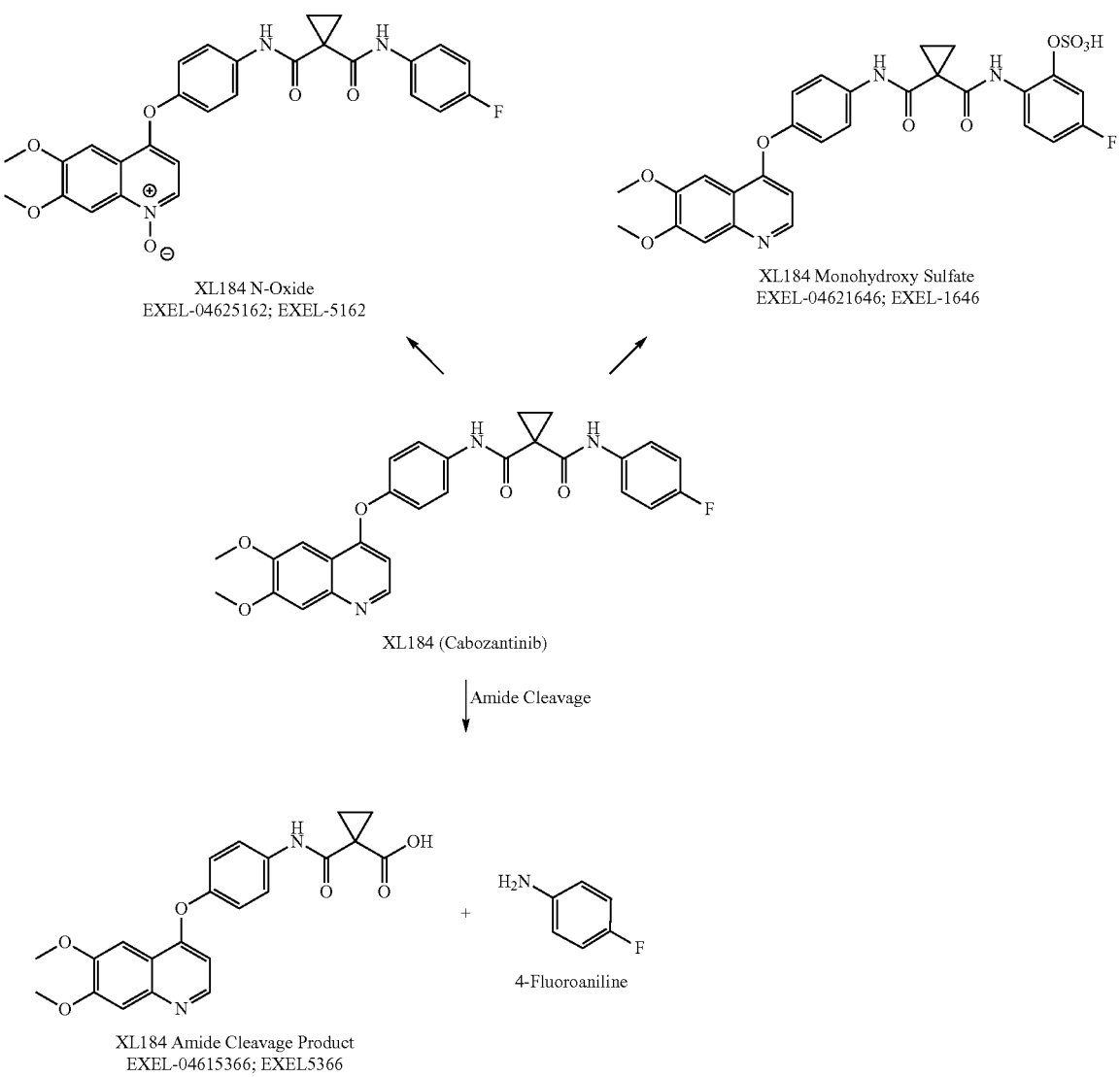

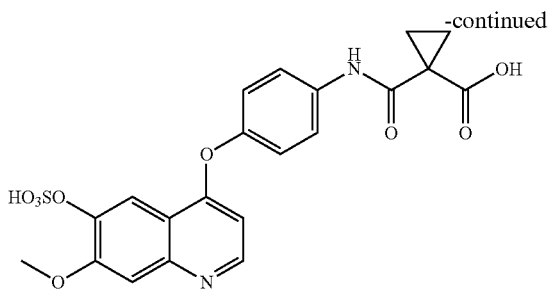

XL184 Desmethyl Amide Cleavage Product sulfate
EXEL-04621644; EXEL-1644

The parent compound, XL184, was rapidly absorbed after oral administration and was eliminated relatively slowly. Following a single oral dose, the median peak concentrations of XL184, XL184-Half-Dimer, XL184-N-Oxide, XL184-Sulfate, 6-Demethyl Half-Dimer Sulfate, P5, and P7 in plasma were achieved at approximately 1.99, 1.49, 3.00, 4.50, 71.99, 2.00, and 2.00 hours with a mean maximum concentration value ($C_{max}$) of 1080, 210, 299, 649, 379, 194, and 95.3 ngEq/mL, respectively. The mean estimated elimination half-lives of XL184, XL184-Half-Dimer, XL184-N-Oxide, XL184-Sulfate, and P5 were 70.5, 57.9, 73.1, 79.2, and 73.4 hours, respectively (FIGS. 11, 12, 13, and 14 and Table 15). However, the elimination half-lives of 6-Demethyl Half-Dimer Sulfate and P7 for all the subjects were not reportable.

For metabolites XL184-Half-Dimer, XL184-N-Oxide, XL184-Sulfate, 6-Demethyl Half-Dimer Sulfate, P5, and P7, the mean metabolite exposure ratios relative to parent XL184 ($AUC_{0-t}$ (metabolite)/$AUC_{0-t}$ (parent)) were 34.4%, 34.1%, 188%, 283%, 24.5%, and 1.54%, respectively. Mean exposure ratios for parent and metabolites XL184-Half-Dimer, XL184-N-Oxide, XL184-Sulfate, 6-Demethyl Half-Dimer Sulfate, P5, and P7 relative to total exposure ($AUC_{0-t}$ (each analyte)/$AUC_{0-t}$ (parent+measured metabolites) were 20.0%, 6.25%, 7.16%, 37.6%, 40.3%, 4.10%, and 0.386%, respectively.

The results of the mean metabolite exposure ratios relative to parent XL184 ($AUC_{0-t}$ (metabolite)/$AUC_{0-t}$ (parent)) and the mean exposure ratios for parent and metabolites relative to total exposure ($AUC_{0-t}$ (each analyte)/$AUC_{0-t}$ (parent+measured metabolites) between LC/MS/MS and the radio-quantitative method are different since they are two different methods. LC/MS/MS was a validated method (except for 6-Demethyl Half-Dimer Sulfate) and was run under the GLP environment in this study. On the contrary, the radio-quantitative method was not a validated method and was run under the non-GLP environment in this study.

TABLE 15

Summary (Mean ± SD and % CV) of Plasma Pharmacokinetic Parameters for XL184 and Selected Metabolites Using a Radio-Quantitative Method* Following a Single 175 mg Oral Administration of XL184 (L-Malate Salt) Containing [$^{14}$C]-XL184 (100 µCi) to Healthy Male Subjects (N = 6).

| Parameters | XL184 | XL184-Half-Dimer | XL184-N-Oxide | XL184-Sulfate | 6-Demethyl Half-Dimer Sulfate | P5 | P7 |
|---|---|---|---|---|---|---|---|
| $C_{max}$, ngEq/mL | 1080 ± 234 (22) | 210 ± 73 (35) | 299 ± 56 (19) | 649 ± 132 (20) | 379 ± 151 (40)[g] | 194 ± 51.1 (26)[h] | 95.3[i] |
| $T_{max}$, h[a] | 1.99 (1.00, 4.00) | 1.49 (1.00, 24.08) | 3.00 (2.00, 4.00) | 4.50 (1.98, 24.08) | 71.99 (24.00, 168.00)[g] | 2.00 (1.98, 5.00)[h] | 2.00[i] |
| $AUC_{0-24}$, h · ngEq/mL | 10700 ± 3170 (30) | 3610 ± 1350 (37) | 4300 ± 1460 (34) | 11300 ± 2360 (21) | 2520 ± 1370 (54)[g] | 2470 ± 1290 (52)[h] | 625[i] |
| $AUC_{0-72}$, h · ngEq/mL | 23800 ± 9340 (39) | 8680 ± 3980 (46) | 10600 ± 3490 (33) | 33200 ± 7940 (24) | 17400 ± 7000 (40)[g] | 5950 ± 2870 (48)[h] | 625[i] |
| $AUC_{0-t}$, h · ngEq/mL | 38100 ± 12800 (34) | 11100 ± 5890 (53) | 13300 ± 8360 (63) | 69900 ± 22000 (31) | 89000 ± 32000 (36)[g] | 7660 ± 442 (6)[h] | 510[i] |
| Ratio[b], % | NA | 34.4 ± 24.7 (72) | 34.1 ± 15.4 (45) | 188 ± 29.1 (15) | 283 ± 200 (71) | 24.5 ± 11.4 (47) | 1.54[i] |
| Ratio[c], % | 20.0 ± 6.24 (31) | 6.25 ± 3.76 (60) | 7.16 ± 4.20 (59) | 37.6 ± 13.9 (37) | 40.3 ± 15.9 (40) | 4.10 ± 1.19 (29) | 0.386[i] |
| $AUC_{0-inf}$, h · ngEq/mL | 40300 ± 12300 (30) | 16400 ± 1770 (11)[d] | 20800 ± 7640 (37)[e] | 74500 ± 22900 (31) | NA | 87201[i] | NA |

TABLE 15-continued

Summary (Mean ± SD and % CV) of Plasma Pharmacokinetic Parameters for XL184 and
Selected Metabolites Using a Radio-Quantitative Method* Following a Single 175 mg Oral Administration
of XL184 (L-Malate Salt) Containing [$^{14}$C]-XL184 (100 µCi) to Healthy Male Subjects (N = 6).

| Parameters | XL184 | XL184-Half-Dimer | XL184-N-Oxide | XL184-Sulfate | 6-Demethyl Half-Dimer Sulfate | P5 | P7 |
|---|---|---|---|---|---|---|---|
| $k_{el}$, 1/h | 0.0112 ± 0.0053 (47) | 0.0136 ± 0.00672 (49)[d] | 0.00976 ± 0.00212 (22)[e] | 0.00923 ± 0.00221 (24) | NA | 0.00945[i] | NA |
| $t_{1/2}$, h | 70.5 ± 23.2 (33) | 57.9 ± 28.4 (49)[d] | 73.1 ± 14.0 (19)[e] | 79.2 ± 21.4 (27) | NA | 73.4[i] | NA |

[a] median (range);
[b] ratio of $AUC_{0-t}$ (metabolite)/$AUC_{0-t}$ (parent);
[c] ratio of $AUC_{0-t}$ (each analyte)/$AUC_{0-t}$ (parent + 6 measured metabolites);
NA: Not Applicable;
[d] N = 2;
[e] N = 3;
NR: Not reportable.
[g] N = 4;
[h] N = 3;
[i] N = 1;
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life.
*The radio-quantitative method was not performed according to GLP regulations.

5. Conclusions

Following oral administration of the 175 mg dose of XL184 (L-Malate Salt) containing 100 µCi [$^{14}$C]-XL184 to eight male healthy volunteers, a mean recovery of total radioactivity of 81.09% was achieved within 48 days. Approximately 1% total mean radioactivity was recovered in feces and urine after Day 28 post-dose. The radioactivity was mainly eliminated in feces (53.79%) and the remainder in urine (27.29%).

Following a single oral dose, the peak radioactivity in plasma and whole blood was achieved at approximately 2 hours (median) with a mean maximum value ($C_{max}$) of 2000 and 1200 ngEq/mL, respectively. The elimination half-life of the total radioactivity in plasma was determined with a mean value of 269 hours. The mean values of systemic exposures ($AUC_{0-24}$ and $AUC_{0-72}$) in plasma were around 1.6 times higher than those in whole blood.

The mean percent total radioactivity concentrations associated with erythrocytes relative to whole blood ranged from 0.174±4.51 to 12.3±3.71 within 72 hours after single dosing, indicating that radioactivity was present primarily in plasma and not markedly associated with red blood cells.

XL184 was rapidly absorbed after oral administration and eliminated relatively slowly. The main circulating metabolite in plasma was 6-Demethyl Half-Dimer Sulfate. Following a single oral dose, the mean peak concentrations of XL184 and metabolites XL184-Half-Dimer, XL184-N-Oxide, XL184-Sulfate, and 6-Demethyl Half-Dimer Sulfate in plasma by LC/MS/MS method were achieved at approximately 1.49, 18.99, 13.50, 24.00, and 168.00 hours (median) with a mean maximum concentration value ($C_{max}$) of 1250, 52.9, 118, 236, and 230 ng/mL, respectively. The mean estimated elimination half-lives of XL184, XL184-Half-Dimer, XL184-N-Oxide, and XL184-Sulfate were 102, 91.8, 89.2, and 86.0 hours, respectively. However, the elimination half-lives of 6-Demethyl Half-Dimer Sulfate for all the subjects could not be determined. Para-fluoroaniline (pFA) metabolite concentrations were below the LLOQ for all subjects.

For metabolites XL184-Half-Dimer, XL184-N-Oxide, XL184-Sulfate, and 6-Demethyl Half-Dimer Sulfate, the mean metabolite exposure ratios relative to parent XL184 ($AUC_{0-t}$ (metabolite)/$AUC_{0-t}$ (parent)) by LC/MS/MS method were 9.93%, 15.0%, 42.9%, and 150%, respectively. Mean exposure ratios for parent and metabolites XL184-Half-Dimer, XL184-N-Oxide, XL184-Sulfate, and 6-Demethyl Half-Dimer Sulfate relative to total exposure ($AUC_{0-t}$ (each analyte)/$AUC_{0-t}$ (parent+4 measured metabolites)) were 32.4%, 3.09%, 4.90%, 13.8%, and 45.9%, respectively.

Following a single oral dose, the median peak concentrations of XL184, XL184-Half-Dimer, XL184-N-Oxide, XL184-Sulfate, 6-Demethyl Half-Dimer Sulfate, P5, and P7 in plasma using a radio-quantitative method were achieved at approximately 1.99, 1.49, 2.00, 4.50, 71.99, 2.00, and 2.00 hours with a mean maximum concentration value ($C_{max}$) of 1080, 210, 299, 649, 379, 194, and 95.3 ngEq/mL, respectively. The mean estimated elimination half-lives of XL184, XL184-Half-Dimer, XL184-N-Oxide, XL184-Sulfate, and P5 were 70.5, 57.9, 73.1, 79.2, and 73.4 hours, respectively For metabolites XL184-Half-Dimer, XL184-N-Oxide, XL184-Sulfate, 6-Demethyl Half-Dimer Sulfate, P5, and P7, the mean metabolite exposure ratios relative to parent XL184 ($AUC_{0-t}$ (metabolite)/$AUC_{0-t}$ (parent)) were 34.4%, 34.1%, 188%, 283%, 24.5%, and 1.54%, respectively. Mean exposure ratios for parent and metabolites XL184-Half-Dimer, XL184-N-Oxide, XL184-Sulfate, 6-Demethyl Half-Dimer Sulfate, P5, and P7 relative to total exposure ($AUC_{0-t}$ (each analyte)/$AUC_{0-t}$ (parent+measured metabolites) were 20.0%, 6.25%, 7.16%, 37.6%, 40.3%, 4.10%, and 0.386%, respectively.

The results of the mean metabolite exposure ratios relative to parent XL184 ($AUC_{0-t}$ (metabolite)/$AUC_{0-t}$ (parent)) and the mean exposure ratios for parent and metabolites relative to total exposure ($AUC_{0-t}$ (each analyte)/$AUC_{0-t}$ (parent+measured metabolites)) between LC/MS/MS and the radio-quantitative method are different since they are two different methods. LC/MS/MS was a validated method (except for 6-Demethyl Half-Dimer Sulfate) and was run under the GLP environment in this study. On the contrary, the radio-quantitative method was not a validated method and was run under the non-GLP environment in this study.

TABLE 16

Individual Urine Cumulative Excretion of $^{14}C$ Total Radioactivity
Following Administration of a Single 175 mg Oral Administration of XL184
(L-Malate Salt) Containing [$^{14}C$]-XL184 (100 μCi) to Healthy Male Subjects

| Time Post-dose (Day) | Time Interval (hrs) | Subject 1444-1010 | 1444-1023 | 1444-1040 | 1444-1042 | 1444-1051 | 1444-1052 | 1444-1057 | 1444-1058 | Summary Statistics Mean | SD | CV % |
|---|---|---|---|---|---|---|---|---|---|---|---|---|
| 0.33 | 8 | 0.75 | 1.29 | 1.08 | 2.31 | 1.56 | 1.08 | 1.38 | 1.24 | 1.34 | 0.46 | 34 |
| 1 | 24 | 2.32 | 4.30 | 3.22 | 7.81 | 3.81 | 3.89 | 4.78 | 3.38 | 4.19 | 1.64 | 39 |
| 2 | 48 | 4.70 | 8.75 | 6.39 | 14.86 | 7.68 | 8.34 | 9.68 | 7.07 | 8.43 | 3.01 | 36 |
| 3 | 72 | 7.26 | 13.09 | 9.22 | 20.34 | 11.00 | 12.23 | 13.67 | 9.75 | 12.07 | 3.96 | 33 |
| 4 | 96 | 9.65 | 16.19 | 11.53 | 24.39 | 13.47 | 15.11 | 16.57 | 12.11 | 14.88 | 4.52 | 30 |
| 5 | 120 | 11.74 | 18.60 | 13.44 | 27.04 | 15.59 | 17.46 | 18.91 | 13.86 | 17.08 | 4.77 | 28 |
| 6 | 144 | 13.48 | 20.51 | 14.81 | 28.88 | 16.94 | 19.11 | 20.68 | 15.33 | 18.72 | 4.90 | 26 |
| 7 | 168 | 15.03 | 22.11 | 15.82 | 30.27 | 18.00 | 20.49 | 22.01 | 16.62 | 20.04 | 4.95 | 25 |
| 8 | 192 | 16.27 | 23.34 | 16.60 | 31.32 | 19.36 | 21.56 | 23.11 | 18.17 | 21.22 | 4.91 | 23 |
| 9 | 216 | 17.35 | 24.24 | 17.22 | 32.02 | 20.33 | 22.44 | 23.99 | 19.02 | 22.08 | 4.86 | 22 |
| 10 | 240 | 18.26 | 25.17 | 17.67 | 32.59 | 21.12 | 23.24 | 24.71 | 19.68 | 22.81 | 4.85 | 21 |
| 11 | 264 | 19.07 | 25.95 | 18.05 | 32.99 | 21.78 | 24.03 | 25.27 | 20.23 | 23.42 | 4.82 | 21 |
| 12 | 288 | 19.85 | 26.61 | 18.34 | 33.28 | 22.27 | 24.73 | 25.73 | 20.71 | 23.94 | 4.77 | 20 |
| 13 | 312 | 20.51 | 27.11 | 18.55 | 33.54 | 22.61 | 25.24 | 26.07 | 21.05 | 24.34 | 4.75 | 20 |
| 14 | 336 | 21.13 | 27.58 | 18.73 | 33.74 | 23.12 | 25.70 | 26.34 | 21.33 | 24.71 | 4.72 | 19 |
| 15 | 360 | 21.69 | 27.98 | 18.88 | 33.91 | 23.45 | 26.14 | 26.60 | 21.59 | 25.03 | 4.70 | 19 |
| 16 | 384 | 22.15 | 28.33 | 18.98 | 34.05 | 23.85 | 26.49 | 26.82 | 21.79 | 25.31 | 4.69 | 19 |
| 17 | 408 | 22.54 | 28.64 | 19.08 | 34.16 | 24.21 | 26.80 | 26.99 | 21.96 | 25.55 | 4.67 | 18 |
| 18 | 432 | 22.89 | 28.85 | 19.16 | 34.24 | 24.52 | 27.05 | 27.13 | 22.12 | 25.75 | 4.65 | 18 |
| 19 | 456 | 23.22 | 29.10 | 19.23 | 34.32 | 24.81 | 27.28 | 27.25 | 22.24 | 25.93 | 4.65 | 18 |
| 20 | 480 | 23.48 | 29.30 | 19.29 | 34.38 | 25.04 | 27.46 | 27.34 | 22.34 | 26.08 | 4.64 | 18 |
| 23 | 504-552 | 24.15 | 29.80 | 19.40 | 34.51 | 25.59 | 27.94 | 27.56 | 22.57 | 26.44 | 4.64 | 18 |
| 26 | 576-624 | 24.69 | 30.14 | 19.49 | 34.62 | 25.98 | 28.27 | 27.71 | 22.74 | 26.71 | 4.63 | 17 |
| 29 | 648-696 | 25.11 | 30.38 | 19.55 | 34.68 | 26.26 | 28.49 | 27.81 | 22.85 | 26.89 | 4.63 | 17 |
| 32 | 720-768 | 25.36 | 30.54 | 19.59 | 34.73 | 26.46 | 28.64 | 27.88 | 22.93 | 27.02 | 4.63 | 17 |
| 35 | 792-840 | 25.52 | 30.67 | 19.61 | 34.77 | 26.61 | 28.77 | 27.94 | 22.99 | 27.11 | 4.64 | 17 |
| 38 | 864-912 | 25.56 | 30.76 | 19.63 | 34.81 | 26.72 | 28.86 | 27.98 | 23.04 | 27.17 | 4.65 | 17 |
| 41 | 936-984 | 25.56 | 30.84 | 19.65 | 34.83 | 26.80 | 28.92 | 28.02 | 23.07 | 27.21 | 4.66 | 17 |
| 44 | 1008-1056 | 25.56 | 30.90 | 19.78 | 34.85 | 26.86 | 28.98 | 28.04 | 23.11 | 27.26 | 4.64 | 17 |
| 47 | 1080-1128 | 25.56 | 30.95 | 19.78 | 34.88 | 26.91 | 29.02 | 28.07 | 23.13 | 27.29 | 4.65 | 17 |
| 48 | 1152 | 25.56 | 30.97 | 19.78 | 34.88 | 26.92 | 29.03 | 28.07 | 23.14 | 27.29 | 4.65 | 17 |

TABLE 17

Individual Feces Cumulative Excretion of $^{14}C$ Total Radioactivity
Following Administration of a Single 175 mg Oral Administration
of [$^{14}C$]-XL184 (100 μCi) to Healthy Male Subjects

| Time Post-dose (Day) | Time Interval (hrs) | Subject 1444-1010 | 1444-1023 | 1444-1040 | 1444-1042 | 1444-1051 | 1444-1052 | 1444-1057 | 1444-1058 | Summary Statistics Mean | SD | CV % |
|---|---|---|---|---|---|---|---|---|---|---|---|---|
| 1 | 24.00 | 0.00 | 1.51 | 0.00 | 0.00 | 7.27 | 0.00 | 0.00 | 6.55 | 1.92 | 3.13 | 163 |
| 2 | 48.00 | 2.41 | 4.69 | 6.21 | 13.42 | 13.75 | 0.00 | 0.00 | 23.82 | 8.04 | 8.33 | 104 |
| 3 | 72.00 | 17.54 | 11.89 | 19.42 | 23.50 | 19.09 | 6.71 | 20.02 | 27.89 | 18.26 | 6.54 | 36 |
| 4 | 96.00 | 29.54 | 15.75 | 26.66 | 23.50 | 24.06 | 21.44 | 20.02 | 33.67 | 24.33 | 5.62 | 23 |
| 5 | 120.00 | 29.54 | 26.82 | 38.33 | 33.66 | 30.04 | 21.44 | 32.13 | 38.11 | 31.26 | 5.66 | 18 |
| 6 | 144.00 | 29.54 | 32.95 | 42.31 | 33.66 | 32.58 | 34.95 | 32.13 | 40.73 | 34.86 | 4.41 | 13 |
| 7 | 168.00 | 37.33 | 35.74 | 46.15 | 37.83 | 35.24 | 34.95 | 39.21 | 42.53 | 38.62 | 3.92 | 10 |
| 8 | 192.00 | 37.33 | 38.12 | 50.16 | 37.83 | 35.24 | 42.36 | 39.21 | 46.78 | 40.88 | 5.17 | 13 |
| 9 | 216.00 | 38.43 | 40.65 | 52.52 | 41.88 | 39.09 | 42.36 | 44.88 | 47.60 | 43.43 | 4.74 | 11 |
| 10 | 240.00 | 40.55 | 40.97 | 53.88 | 41.88 | 40.04 | 42.36 | 44.88 | 49.11 | 44.21 | 4.90 | 11 |
| 11 | 264.00 | 40.55 | 42.16 | 56.19 | 44.05 | 41.53 | 42.36 | 47.81 | 51.46 | 45.76 | 5.58 | 12 |
| 12 | 288.00 | 43.16 | 45.59 | 57.02 | 44.05 | 43.34 | 46.17 | 47.81 | 51.70 | 47.36 | 4.81 | 10 |
| 13 | 312.00 | 43.16 | 45.85 | 58.37 | 44.65 | 43.60 | 46.17 | 49.96 | 53.34 | 48.14 | 5.37 | 11 |
| 14 | 336.00 | 44.52 | 46.96 | 58.62 | 44.65 | 45.13 | 47.75 | 49.96 | 54.31 | 48.99 | 5.09 | 10 |
| 15 | 360.00 | 46.60 | 47.74 | 59.19 | 44.65 | 45.47 | 47.75 | 50.79 | 54.76 | 49.62 | 5.03 | 10 |
| 16 | 384.00 | 48.10 | 48.28 | 59.83 | 45.48 | 46.43 | 47.75 | 50.79 | 55.20 | 50.23 | 4.91 | 10 |
| 17 | 408.00 | 49.60 | 48.83 | 60.27 | 45.48 | 46.79 | 49.42 | 51.79 | 55.60 | 50.97 | 4.86 | 10 |
| 18 | 432.00 | 49.60 | 49.07 | 60.38 | 45.89 | 47.53 | 49.42 | 51.79 | 55.93 | 51.20 | 4.76 | 9 |
| 19 | 456.00 | 50.94 | 49.54 | 60.68 | 45.89 | 47.53 | 50.45 | 52.32 | 56.14 | 51.69 | 4.76 | 9 |
| 20 | 480.00 | 51.52 | 49.81 | 60.90 | 46.07 | 48.35 | 50.45 | 52.32 | 56.50 | 51.99 | 4.71 | 9 |
| 21 | 504.00 | 51.52 | 50.21 | 61.01 | 46.07 | 48.80 | 50.89 | 52.62 | 56.69 | 52.23 | 4.68 | 9 |
| 24 | 528-576 | 52.49 | 50.91 | 61.34 | 46.17 | 49.60 | 51.46 | 52.95 | 57.04 | 52.75 | 4.64 | 9 |

TABLE 17-continued

Individual Feces Cumulative Excretion of $^{14}C$ Total Radioactivity Following Administration of a Single 175 mg Oral Administration of $[^{14}C]$-XL184 (100 µCi) to Healthy Male Subjects

| Time Post-dose (Day) | Time Interval (hrs) | Subject 1444-1010 | 1444-1023 | 1444-1040 | 1444-1042 | 1444-1051 | 1444-1052 | 1444-1057 | 1444-1058 | Summary Statistics Mean | SD | CV % |
|---|---|---|---|---|---|---|---|---|---|---|---|---|
| 27 | 600-648 | 52.58 | 51.55 | 61.60 | 46.35 | 49.90 | 51.79 | 53.09 | 57.29 | 53.02 | 4.63 | 9 |
| 30 | 672-720 | 53.58 | 51.77 | 61.75 | 46.44 | 50.45 | 52.07 | 53.29 | 57.46 | 53.35 | 4.60 | 9 |
| 33 | 744-792 | 54.17 | 52.00 | 61.82 | 46.48 | 50.76 | 52.56 | 53.41 | 57.56 | 53.60 | 4.57 | 9 |
| 36 | 816-864 | 54.27 | 52.19 | 61.89 | 46.48 | 50.95 | 52.56 | 53.45 | 57.67 | 53.68 | 4.57 | 9 |
| 39 | 888-936 | 54.27 | 52.30 | 61.89 | 46.54 | 51.11 | 52.71 | 53.45 | 57.67 | 53.74 | 4.54 | 8 |
| 42 | 960-1008 | 54.27 | 52.41 | 61.89 | 46.54 | 51.22 | 52.81 | 53.45 | 57.67 | 53.78 | 4.52 | 8 |
| 45 | 1032-1080 | 54.27 | 52.41 | 61.89 | 46.54 | 51.22 | 52.89 | 53.45 | 57.67 | 53.79 | 4.52 | 8 |
| 48 | 1104-1152 | 54.27 | 52.41 | 61.89 | 46.54 | 51.22 | 52.89 | 53.45 | 57.67 | 53.79 | 4.52 | 8 |

TABLE 18

Individual and Mean (±SD) Total Cumulative Recoveries of XL184 Following Administration of a Single 175 mg Oral Administration of XL184 (L-Malate Salt) Containing [$^{14}C$]-XL184 (100 µCi) to Healthy Male Subjects

| Subject | % Dose Administered Urine | Feces | Total |
|---|---|---|---|
| 1444-1010 | 25.56 | 54.27 | 79.83 |
| 1444-1023 | 30.97 | 52.41 | 83.38 |
| 1444-1040 | 19.78 | 61.89 | 81.67 |
| 1444-1042 | 34.88 | 46.54 | 81.42 |
| 1444-1051 | 26.92 | 51.22 | 78.14 |
| 1444-1052 | 29.03 | 52.89 | 81.92 |
| 1444-1057 | 28.07 | 53.45 | 81.52 |
| 1444-1058 | 23.14 | 57.67 | 80.81 |
| N | 8 | 8 | 8 |
| Mean | 27.29 | 53.79 | 81.09 |
| SD | 4.65 | 4.52 | 1.56 |
| SE | 1.65 | 1.60 | 0.55 |
| Min | 19.78 | 46.54 | 78.14 |
| Median | 27.50 | 53.17 | 81.47 |
| Max | 34.88 | 61.89 | 83.38 |
| CV % | 17 | 8 | 2 |
| Geometric Mean | 26.94 | 53.63 | 81.07 |

TABLE 19

Individual and Mean Plasma $^{14}C$ Total Radioactivity (ngEq/mL) Following a Single 175 mg Oral Administration of XL184 (L-Malate Salt) Containing [$^{14}C$]-XL184 (100 µCi) to Healthy Male Subjects

| Subject | 0.00 | 0.50 | 1.00 | 2.00 | 3.00 | 4.00 | 5.00 | 8.00 | 14.00 | 24.00 |
|---|---|---|---|---|---|---|---|---|---|---|
| 1444-1010 | 0.00 | 575.58 | 1170.98 | 1151.99 | 957.10 | 1166.03 | 828.28 | 562.37 | 625.13 | 1156.95 |
| 1444-1023 | 0.00 | 637.52 | 1307.24 | 1619.39 | 1679.68 | 1583.06 | 1398.91 | 1100.79 | 1072.71 | 1415.42 |
| 1444-1040 | 0.00 | 552.46 | 1494.70 | 2134.69 | 2072.76 | 2093.40 | 1824.19 | 1334.49 | 1493.87 | 1889.43 |
| 1444-1042 | 0.00 | 145.34 | 1165.20 | 2318.85 | 2358.48 | 2384.91 | 1938.98 | 1178.42 | 1366.70 | 2109.92 |
| 1444-1051 | 0.00 | 733.31 | 1703.63 | 1744.92 | 1535.99 | 1426.16 | 1209.80 | 926.55 | 949.67 | 1166.03 |
| 1444-1052 | 0.00 | 477.31 | 1296.51 | 2113.22 | 2389.04 | 1850.62 | 1538.47 | 1157.77 | 1204.02 | 1458.36 |
| 1444-1057 | 0.00 | 1003.35 | 2068.63 | 2189.20 | 1814.28 | 1859.70 | 1397.25 | 1177.59 | 1267.60 | 1455.06 |
| 1444-1058 | 0.00 | 677.98 | 1797.77 | 2277.56 | 1733.35 | 1788.68 | 1136.30 | 1383.22 | 1077.67 | 1461.67 |
| N | 8 | 8 | 8 | 8 | 8 | 8 | 8 | 8 | 8 | 8 |
| Mean | 0.00 | 600.36 | 1500.58 | 1943.73 | 1817.59 | 1769.07 | 1409.02 | 1102.65 | 1132.17 | 1514.11 |
| SD | 0.00 | 242.77 | 327.85 | 405.18 | 467.53 | 380.89 | 362.84 | 259.06 | 268.92 | 330.29 |
| SEM | 0.00 | 85.83 | 115.91 | 143.25 | 165.30 | 134.67 | 128.28 | 91.59 | 95.08 | 116.78 |
| Min | 0.00 | 145.34 | 1165.20 | 1151.99 | 957.10 | 1166.03 | 828.28 | 562.37 | 625.13 | 1156.95 |
| Median | 0.00 | 606.55 | 1400.97 | 2123.96 | 1773.82 | 1819.65 | 1398.08 | 1167.68 | 1140.85 | 1456.71 |
| Max | 0.00 | 1003.35 | 2068.63 | 2318.85 | 2389.04 | 2384.91 | 1938.98 | 1383.22 | 1493.87 | 2109.92 |
| % CV | NA | 40 | 22 | 21 | 26 | 22 | 26 | 23 | 24 | 22 |
| GM | NA | 537.97 | 1470.80 | 1899.92 | 1756.69 | 1731.81 | 1365.83 | 1068.66 | 1099.67 | 1484.70 |

GM: Geometric Mean;

NA: not applicable;

ngEq, an equivalent amount of XL184 freebase required to produce a measured or calculated amount of total radioactivity;

TABLE 19A

Individual and Mean Plasma $^{14}$C Total Radioactivity (ngEq/mL) Following a Single 175 mg Oral Administration of XL184 (L-Malate Salt) Containing [$^{14}$C]-XL184 (100 μCi) to Healthy Male Subjects

| Subject | Time (hours) | | | | | | | | | |
|---|---|---|---|---|---|---|---|---|---|---|
| | 48.00 | 72.00 | 120.00 | 144.00 | 168.00 | 240.00 | 336.00 | 408.00 | 504.00 | 648.00 |
| 1444-1010 | 663.12 | 694.50 | 539.25 | 470.71 | 454.19 | 305.55 | 245.26 | 206.45 | 156.90 | 99.10 |
| 1444-1023 | 1130.52 | 861.31 | 610.27 | 561.54 | 516.95 | 317.93 | 202.32 | 165.16 | 125.52 | 94.14 |
| 1444-1040 | 1401.38 | 919.12 | 572.28 | 540.07 | 478.14 | 223.79 | 132.95 | 0.00 | 0.00 | 0.00 |
| 1444-1042 | 1689.59 | 1305.59 | 665.59 | 580.54 | 528.51 | 351.79 | 205.62 | 177.55 | 144.52 | 111.48 |
| 1444-1051 | 1131.35 | 913.33 | 618.52 | 537.60 | 535.94 | 371.61 | 248.57 | 206.45 | 146.99 | 130.48 |
| 1444-1052 | 1080.15 | 861.31 | 606.96 | 579.71 | 494.65 | 402.16 | 307.20 | 227.92 | 184.15 | 151.95 |
| 1444-1057 | 986.01 | 858.83 | 580.54 | 518.60 | 443.45 | 289.86 | 200.67 | 144.52 | 114.79 | 91.66 |
| 1444-1058 | 1392.30 | 1414.60 | 888.56 | 796.90 | 644.12 | 430.24 | 317.11 | 237.83 | 199.84 | 149.47 |
| N | 8 | 8 | 8 | 8 | 8 | 8 | 8 | 8 | 8 | 8 |
| Mean | 1184.30 | 978.57 | 635.25 | 573.21 | 511.99 | 336.62 | 232.46 | 170.74 | 134.09 | 103.54 |
| SD | 310.11 | 247.09 | 108.87 | 97.19 | 63.04 | 66.27 | 60.61 | 75.82 | 61.00 | 48.12 |
| SEM | 109.64 | 87.36 | 38.49 | 34.36 | 22.29 | 23.43 | 21.43 | 26.81 | 21.57 | 17.01 |
| Min | 663.12 | 694.50 | 539.25 | 470.71 | 443.45 | 223.79 | 132.95 | 0.00 | 0.00 | 0.00 |
| Median | 1130.94 | 887.32 | 608.62 | 550.81 | 505.80 | 334.86 | 225.44 | 192.00 | 145.76 | 105.29 |
| Max | 1689.59 | 1414.60 | 888.56 | 796.90 | 644.12 | 430.24 | 317.11 | 237.83 | 199.84 | 151.95 |
| % CV | 26 | 25 | 17 | 17 | 12 | 20 | 26 | 44 | 45 | 46 |
| GM | 1146.14 | 953.99 | 628.27 | 566.94 | 508.82 | 330.55 | 225.10 | NA | NA | NA |

GM: Geometric Mean;
NA: not applicable;
ngEq, an equivalent amount of XL184 freebase required to produce a measured or calculated amount of total radioactivity.

TABLE 20

Individual and Mean Whole Blood 14C Total Radioactivity (ngEq/mL) Following a Single 175 mg Oral Administration of XL184 (L-Malate Salt) Containing [14C]-XL184 (100 μCi) to Healthy Male Subjects

| Subject | Time (hours) | | | | | | | |
|---|---|---|---|---|---|---|---|---|
| | 0.00 | 1.00 | 2.00 | 4.00 | 8.00 | 14.00 | 24.00 | 72.00 |
| 1444-1010 | 0.00 | 717.47 | 763.98 | 742.45 | 395.34 | 432.38 | 701.11 | 452.19 |
| 1444-1023 | 0.00 | 839.78 | 998.26 | 928.49 | 647.70 | 695.94 | 764.84 | 503.00 |
| 1444-1040 | 0.00 | 916.43 | 1309.19 | 1303.16 | 873.37 | 908.68 | 986.20 | 540.04 |
| 1444-1042 | 0.00 | 776.04 | 1536.58 | 1458.20 | 813.08 | 941.41 | 1196.36 | 845.81 |
| 1444-1051 | 0.00 | 952.61 | 1077.50 | 879.40 | 620.14 | 624.45 | 692.49 | 562.44 |
| 1444-1052 | 0.00 | 817.38 | 1260.96 | 1162.77 | 799.30 | 744.17 | 883.70 | 510.76 |
| 1444-1057 | 0.00 | 1137.79 | 1222.20 | 1056.83 | 708.86 | 769.15 | 786.38 | 450.46 |
| 1444-1058 | 0.00 | 1136.07 | 1389.29 | 1048.21 | 821.69 | 720.05 | 854.42 | 764.84 |
| N | 8 | 8 | 8 | 8 | 8 | 8 | 8 | 8 |
| Mean | 0.00 | 911.70 | 1194.75 | 1072.44 | 709.94 | 729.53 | 858.19 | 578.69 |
| SD | 0.00 | 157.37 | 242.26 | 232.35 | 155.26 | 160.06 | 167.93 | 146.65 |
| SEM | 0.00 | 55.64 | 85.65 | 82.15 | 54.89 | 56.59 | 59.37 | 51.85 |
| Min | 0.00 | 717.47 | 763.98 | 742.45 | 395.34 | 432.38 | 692.49 | 450.46 |
| Median | 0.00 | 878.11 | 1241.58 | 1052.52 | 754.08 | 732.11 | 820.40 | 525.40 |
| Max | 0.00 | 1137.79 | 1536.58 | 1458.20 | 873.37 | 941.41 | 1196.36 | 845.81 |
| % CV | NA | 17 | 20 | 22 | 22 | 22 | 20 | 25 |
| GM | NA | 900.21 | 1171.16 | 1050.57 | 691.86 | 712.27 | 845.09 | 564.30 |

GM: Geometric Mean;
NA: not applicable;
ngEq, an equivalent amount of XL184 freebase required to produce a measured or calculated amount of total radioactivity

TABLE 21

Individual and Mean Hematocrit Value

| Subject | Hematocrit (%) | | | |
|---|---|---|---|---|
| | Day −1 | Day 2 | Day 4 | Mean |
| 1444-1010 | 40.8 | 41.1 | 39.7 | 40.5 |
| 1444-1023 | 44.6 | 45.7 | 44.2 | 44.8 |
| 1444-1040 | 41.8 | 44.3 | 42.5 | 42.9 |
| 1444-1042 | 41.7 | 42.0 | 44.6 | 42.8 |
| 1444-1051 | 42.6 | 41.9 | 42.2 | 42.2 |
| 1444-1052 | 43.9 | 42.5 | 42.0 | 42.8 |
| 1444-1057 | 48.2 | 46.6 | 46.3 | 47.0 |
| 1444-1058 | 42.6 | 41.9 | 42.2 | 42.2 |
| 1444-1010 | 43.5 | 41.8 | 42.4 | 42.6 |

TABLE 22

Individual and Descriptive Statistics of the Percentage of $^{14}$C Radioactivity Associated with Erythrocytes in Whole Blood (ETR) over Time Following a Single 175 mg Oral Administration of XL184 (L-Malate Salt) Containing [$^{14}$C]-XL184 (100 μCi) to Healthy Male Subjects

| Subject | Time (hours) | | | | | | |
|---|---|---|---|---|---|---|---|
| | 1.00 | 2.00 | 4.00 | 8.00 | 14.00 | 24.00 | 72.00 |
| 1444-1010 | 2.89 | 10.3 | 6.55 | 15.4 | 14.0 | 1.81 | 8.62 |
| 1444-1023 | 14.1 | 10.5 | 5.88 | 6.19 | 14.9 | −2.15 | 5.48 |
| 1444-1040 | 6.87 | 6.90 | 8.27 | 12.8 | 6.13 | −9.40 | 2.82 |
| 1444-1042 | 14.1 | 13.7 | 6.45 | 17.1 | 17.0 | −0.88 | 11.7 |
| 1444-1051 | −3.37 | 6.40 | 6.26 | 13.6 | 12.1 | 2.68 | 6.14 |
| 1444-1052 | 9.27 | 4.14 | 8.96 | 17.2 | 7.45 | 5.60 | 3.54 |
| 1444-1057 | 3.64 | 5.07 | 6.74 | 12.0 | 12.7 | 1.93 | −1.05 |
| 1444-1058 | 9.17 | 5.90 | 2.05 | 3.37 | 14.1 | 1.80 | −6.16 |
| N | 8 | 8 | 8 | 8 | 8 | 8 | 8 |
| Mean | 7.08 | 7.85 | 6.40 | 12.2 | 12.3 | 0.174 | 3.89 |
| SD | 5.93 | 3.27 | 2.05 | 5.00 | 3.71 | 4.51 | 5.58 |
| SEM | 2.10 | 1.16 | 0.725 | 1.77 | 1.31 | 1.59 | 1.97 |
| Min | −3.4 | 4.1 | 2.1 | 3.4 | 6.1 | −9.4 | −6.2 |
| Median | 8.0 | 6.7 | 6.5 | 13 | 13 | 1.8 | 4.5 |
| Max | 14 | 14 | 9.0 | 17 | 17 | 5.6 | 12 |
| % CV | 84 | 42 | 32 | 41 | 30 | 2595 | 143 |
| GM | NA | 7.30 | 5.96 | 10.9 | 11.7 | NA | NA |

ETR = Xe/Xb = 1 − [Cp × (1 − Hct)/Cb], where Cp stands for concentration of radioactivity in plasma, Cb stands for concentration of radioactivity in blood and Hct stands for hemocrit value.
Hematocrit values for Days −1, 2, and 4 were averaged for use in this calculation.
GM: geometric me

TABLE 23

Individual Subject Actual Blood Sampling Times for Plasma for Total Radioactivity and for Pharmacokinetic Analysis of XL184 and Its Metabolites Following a Single 175 mg Oral Administration of XL184 (L-Malate Salt) Containing [$^{14}$C]-XL184 (100 μCi) to Healthy Male Subjects Time (hours)

0-24 hrs

| Subject | 0.00 | 0.50 | 1.00 | 2.00 | 3.00 | 4.00 | 5.00 | 8.00 | 14.00 | 24.00 |
|---|---|---|---|---|---|---|---|---|---|---|
| 1444-1010 | 0.00 | 0.50 | 1.00 | 2.00 | 3.00 | 4.00 | 5.00 | 7.98 | 13.98 | 24.00 |
| 1444-1023 | 0.00 | 0.50 | 1.00 | 1.98 | 3.00 | 4.00 | 5.00 | 7.98 | 13.98 | 24.00 |
| 1444-1040 | 0.00 | 0.50 | 1.00 | 2.00 | 3.00 | 4.00 | 5.00 | 8.00 | 14.00 | 24.03 |
| 1444-1042 | 0.00 | 0.50 | 1.00 | 2.00 | 3.00 | 4.00 | 5.00 | 8.00 | 13.98 | 24.03 |
| 1444-1051 | 0.00 | 0.50 | 1.00 | 2.00 | 3.00 | 4.00 | 5.00 | 8.00 | 13.98 | 24.08 |
| 1444-1052 | 0.00 | 0.50 | 1.00 | 1.98 | 3.00 | 4.00 | 5.00 | 8.00 | 14.00 | 24.10 |
| 1444-1057 | 0.00 | 0.50 | 1.00 | 2.00 | 3.00 | 4.00 | 5.00 | 8.00 | 14.00 | 24.08 |
| 1444-1058 | 0.00 | 0.50 | 1.00 | 2.00 | 3.00 | 4.00 | 5.00 | 8.00 | 14.00 | 23.68 |

48-648 hrs

| Subject | 48.00 | 72.00 | 120.00 | 144.00 | 168.00 | 240.00 | 336.00 | 408.00 | 504.00 | 648.00 |
|---|---|---|---|---|---|---|---|---|---|---|
| 1444-1010 | 48.03 | 72.00 | 120.00 | 144.00 | 168.00 | 240.00 | 336.00 | 407.98 | 504.00 | 648.00 |
| 1444-1023 | 48.00 | 72.00 | 120.00 | 144.00 | 168.00 | 239.98 | 336.00 | 407.98 | 504.00 | 648.00 |
| 1444-1040 | 48.00 | 72.00 | 120.00 | 143.98 | 168.00 | 240.00 | 336.00 | 408.00 | 503.98 | 648.00 |
| 1444-1042 | 48.00 | 71.97 | 120.00 | 143.98 | 168.00 | 240.00 | 336.00 | 407.98 | 503.98 | 648.00 |
| 1444-1051 | 48.00 | 71.98 | 120.00 | 144.00 | 167.98 | 240.00 | 336.00 | 407.98 | 503.98 | 647.98 |
| 1444-1052 | 48.00 | 71.98 | 120.00 | 143.98 | 168.00 | 240.00 | 335.87 | 407.98 | 503.98 | 648.00 |
| 1444-1057 | 48.00 | 71.98 | 120.00 | 144.00 | 168.00 | 240.00 | 335.95 | 407.98 | 503.98 | 647.98 |
| 1444-1058 | 48.00 | 72.00 | 119.98 | 143.98 | 168.00 | 240.00 | 336.00 | 407.98 | 503.98 | 648.00 |

TABLE 24

Individual Subject Actual Blood Sampling Times for Whole Blood Analysis of Total Radioactivity Following a Single 175 mg Oral Administration of XL184 (L-Malate Salt) Containing [$^{14}$C]-XL184 (100 µCi) to Healthy Male Subjects

| Subject | Time (hours) | | | | | | | |
|---|---|---|---|---|---|---|---|---|
| | 0.00 | 1.00 | 2.00 | 4.00 | 8.00 | 14.00 | 24.00 | 72.00 |
| 1444-1010 | 0.00 | 1.00 | 2.00 | 4.00 | 7.98 | 13.98 | 24.00 | 72.00 |
| 1444-1023 | 0.00 | 1.00 | 1.98 | 4.00 | 7.98 | 13.98 | 24.00 | 72.00 |
| 1444-1040 | 0.00 | 1.00 | 2.00 | 4.00 | 8.00 | 14.00 | 24.03 | 72.00 |
| 1444-1042 | 0.00 | 1.00 | 2.00 | 4.00 | 8.00 | 13.98 | 24.03 | 71.97 |
| 1444-1051 | 0.00 | 1.00 | 2.00 | 4.00 | 8.00 | 13.98 | 24.08 | 71.98 |
| 1444-1052 | 0.00 | 1.00 | 1.98 | 4.00 | 8.00 | 14.00 | 24.10 | 71.98 |
| 1444-1057 | 0.00 | 1.00 | 2.00 | 4.00 | 8.00 | 14.00 | 24.08 | 71.98 |
| 1444-1058 | 0.00 | 1.00 | 2.00 | 4.00 | 8.00 | 14.00 | 23.68 | 72.00 |

TABLE 25

Individual Subject Actual Blood Sampling Times for Plasma for Possible Metabolic Profiling Following a Single 175 mg Oral Administration of XL184 (L-Malate Salt) Containing [$^{14}$C]-XL184 (100 µCi) to Healthy Male Subjects

| Subject | Time (hours) | | | | | | | | | | | | | | |
|---|---|---|---|---|---|---|---|---|---|---|---|---|---|---|---|
| | 0.00 | 0.50 | 1.00 | 2.00 | 3.00 | 4.00 | 5.00 | 8.00 | 14.00 | 24.00 | 72.00 | 168.00 | 336.00 | 504.00 | 648.00 |
| 1444-1010 | 0.00 | 0.50 | 1.00 | 2.00 | 3.00 | 4.00 | 5.00 | 7.98 | 13.98 | 24.00 | 72.00 | 168.00 | 336.00 | 504.00 | 648.00 |
| 1444-1023 | 0.00 | 0.50 | 1.00 | 1.98 | 3.00 | 4.00 | 5.00 | 7.98 | 13.98 | 24.00 | 72.00 | 168.00 | 336.00 | 504.00 | 648.00 |
| 1444-1040 | 0.00 | 0.50 | 1.00 | 2.00 | 3.00 | 4.00 | 5.00 | 8.00 | 14.00 | 24.03 | 72.00 | 168.00 | 336.00 | 503.98 | 648.00 |
| 1444-1042 | 0.00 | 0.50 | 1.00 | 2.00 | 3.00 | 4.00 | 5.00 | 8.00 | 13.98 | 24.03 | 71.97 | 168.00 | 336.00 | 503.98 | 648.00 |
| 1444-1051 | 0.00 | 0.50 | 1.00 | 2.00 | 3.00 | 4.00 | 5.00 | 8.00 | 13.98 | 24.08 | 71.98 | 167.98 | 336.00 | 503.98 | 647.98 |
| 1444-1052 | 0.00 | 0.50 | 1.00 | 1.98 | 3.00 | 4.00 | 5.00 | 8.00 | 14.00 | 24.10 | 71.98 | 168.00 | 335.87 | 503.98 | 648.00 |
| 1444-1057 | 0.00 | 0.50 | 1.00 | 2.00 | 3.00 | 4.00 | 5.00 | 8.00 | 14.00 | 24.08 | 71.98 | 168.00 | 335.95 | 503.98 | 647.98 |
| 1444-1058 | 0.00 | 0.50 | 1.00 | 2.00 | 3.00 | 4.00 | 5.00 | 8.00 | 14.00 | 23.68 | 72.00 | 168.00 | 336.00 | 503.98 | 648.00 |

TABLE 26

Individual and Descriptive Statistics of Plasma Pharmacokinetic Parameters of Total Radioactivity Following a Single 175 mg Oral Administration of XL184 (L-Malate Salt) Containing [$^{14}$C]-XL184 (100 µCi) to Healthy Male Subjects

| Subject_ID | $C_{max}$ (ngEq/mL) | $t_{max}$ (h) | $AUC_{0-t}$ (h·ngEq/mL) | $AUC_{0-24}$ (h·ngEq/mL) | $AUC_{0-72}$ (h·ngEq/mL) | $AUC_{0-inf}$ (h·ngEq/mL) | $k_{el}$ (1/h) | $t_{1/2}$ (h) |
|---|---|---|---|---|---|---|---|---|
| 1444-1010 | 1170 | 1.00 | 216000 | 19400 | 57600 | 249000 | 0.00307 | 226 |
| 1444-1023 | 1680 | 3.00 | 244000 | 29600 | 84000 | 283000 | 0.00246 | 282 |
| 1444-1040 | 2130 | 2.00 | 210000 | 38700 | 106000 | 228000 | 0.00741 | 93.5 |
| 1444-1042 | 2380 | 4.00 | 302000 | 38700 | 120000 | 359000 | 0.00197 | 352 |
| 1444-1051 | 1740 | 2.00 | 258000 | 26400 | 78500 | 299000 | 0.00317 | 218 |
| 1444-1052 | 2390 | 3.00 | 278000 | 32800 | 86500 | 333000 | 0.00278 | 250 |
| 1444-1057 | 2190 | 2.00 | 234000 | 33400 | 84900 | 283000 | 0.00187 | 371 |
| 1444-1058 | 2280 | 2.00 | 333000 | 32000 | 99900 | 410000 | 0.00194 | 357 |
| N | 8 | 8 | 8 | 8 | 8 | 8 | 8 | 8 |
| Mean | 2000 | 2.38 | 259000 | 31400 | 89700 | 306000 | 0.00308 | 269 |
| SD | 429 | 0.92 | 42700 | 6380 | 19000 | 59500 | 0.00182 | 93.2 |
| SEM | 152 | 0.32 | 15100 | 2260 | 6720 | 21000 | 0.000644 | 33.0 |
| Min | 1170 | 1.00 | 210000 | 19400 | 57600 | 228000 | 0.00187 | 93.5 |
| Median | 2160 | 2.00 | 251000 | 32400 | 85700 | 291000 | 0.00262 | 266 |
| Max | 2390 | 4.00 | 333000 | 38700 | 120000 | 410000 | 0.00741 | 371 |
| % CV | 21 | 39 | 16 | 20 | 21 | 19 | 59 | 35 |
| GM | 1950 | 2.21 | 256000 | 30700 | 87900 | 301000 | 0.00278 | 250 |

GM: Geometric Mean;

$C_{max}$, maximum observed concentration;

$T_{max}$, time of the maximum concentration;

$AUC_{0-t}$, area under the concentration-time curve from time zero to the time of the last measurable concentration;

$AUC_{0-24}$, area under the concentration-time curve from time zero to 24 hours post XL184 dose;

$AUC_{0-72}$, area under the concentration-time curve from time zero to 72 hours post XL184 dose;

$AUC_{0-inf}$, area under the concentration-time curve from time zero to infinity;

$k_{el}$, apparent terminal elimination rate constant;

$t_{1/2}$, apparent terminal elimination half-life;

CL/F, apparent total body clearance;

V/F, apparent total volume of distribution;

ngEq, an equivalent amount of XL184 freebase required to produce a measured or calculated amount of total radioactivity.

TABLE 27

Individual and Descriptive Statistics of Whole Blood Pharmacokinetic Parameters of Total Radioactivity following a Single 175 mg Oral Administration of XL184 (L-Malate Salt) Containing [$^{14}$C]-XL184 (100 μCi) to Healthy Male Subjects

| Subject | $C_{max}$ (ngEq/mL) | $t_{max}$ (h) | $AUC_{0-t}$ (h · ngEq/mL) | $AUC_{0-24}$ (h · ngEq/mL) | $AUC_{0-72}$ (h · ngEq/mL) | Ratio[a] (%) | Ratio[b] (%) | Ratio[c] (%) | Ratio[d] (%) |
|---|---|---|---|---|---|---|---|---|---|
| 1444-1010 | 764 | 2.00 | 40700 | 13000 | 40700 | 153 | 531 | 149 | 142 |
| 1444-1023 | 998 | 1.98 | 48200 | 17800 | 48200 | 168 | 506 | 166 | 174 |
| 1444-1040 | 1310 | 2.00 | 60000 | 23400 | 60000 | 163 | 350 | 165 | 177 |
| 1444-1042 | 1540 | 2.00 | 74000 | 25000 | 74000 | 155 | 408 | 155 | 162 |
| 1444-1051 | 1080 | 2.00 | 46900 | 16800 | 46900 | 161 | 550 | 157 | 167 |
| 1444-1052 | 1260 | 1.98 | 54000 | 20600 | 54000 | 190 | 515 | 159 | 160 |
| 1444-1057 | 1220 | 2.00 | 49500 | 19800 | 49500 | 180 | 473 | 169 | 172 |
| 1444-1058 | 1390 | 2.00 | 59400 | 20500 | 59400 | 164 | 561 | 156 | 168 |
| N | 8 | 8 | 8 | 8 | 8 | 8 | 8 | 8 | 8 |
| Mean | 1200 | 2.00 | 54100 | 19600 | 54100 | 167 | 487 | 160 | 165 |
| SD | 243 | 0.01 | 10300 | 3780 | 10300 | 12.4 | 73.3 | 6.65 | 11.1 |
| SEM | 85.9 | 0.00 | 3650 | 1340 | 3660 | 4.39 | 25.9 | 2.35 | 3.92 |
| Min | 764 | 1.98 | 40700 | 13000 | 40700 | 153 | 350 | 149 | 142 |
| Median | 1240 | 2.00 | 51800 | 20100 | 51800 | 163 | 511 | 158 | 168 |
| Max | 1540 | 2.00 | 74000 | 25000 | 74000 | 190 | 561 | 169 | 177 |
| % CV | 20 | 0 | 19 | 19 | 19 | 7 | 15 | 4 | 7 |
| GM | 1170 | 1.99 | 53300 | 19300 | 53300 | 166 | 481 | 159 | 165 |

GM: Geometric Mean;

$AUC_{0-inf}$, kel and t½ were not reportable since the value of $AUC_{0-t}/AUC_{0-inf}$ for each subject was < 0.80;

[a], [b], [c] and [d] % ratio of plasma to whole blood for $C_{max}$, $AUC_{0-t}$, $AUC_{0-24}$ and $AUC_{0-72}$, respectively.

$C_{max}$, maximum observed concentration;

$T_{max}$, time of the maximum concentration;

$AUC_{0-t}$, area under the concentration-time curve from time zero to the time of the last measurable concentration;

$AUC_{0-24}$, area under the concentration-time curve from time zero to 24 hours post XL184 dose;

$AUC_{0-72}$, area under the concentration-time curve from time zero to 72 hours post XL184 dose;

$AUC_{0-inf}$, area under the concentration-time curve from time zero to infinity;

kel, apparent terminal elimination rate constant;

t½, apparent terminal elimination half-life;

CL/F, apparent total body clearance;

V/F, apparent total volume of distribution;

ngEq, an equivalent amount of XL184 freebase required to produce a measured or calculated amount of total radioactivity.

TABLE 28

Individual and Mean Plasma Concentrations (ng/mL) of XL184 by LC/MS/MS Method Following a Single 175 mg Oral Administration of XL184 (L-Malate Salt) Containing [$^{14}$C]-XL184 (100 μCi) to Healthy Male Subjects 0-24 hrs

| | Time (hours) | | | | | | | | | |
|---|---|---|---|---|---|---|---|---|---|---|
| Subject | 0.00 | 0.50 | 1.00 | 2.00 | 3.00 | 4.00 | 5.00 | 8.00 | 14.00 | 24.00 |
| 1444-1010 | 0.000 | 377.055 | 777.766 | 703.373 | 459.276 | 682.206 | 409.319 | 266.879 | 335.869 | 681.961 |
| 1444-1023 | 0.000 | 410.653 | 988.621 | 1026.742 | 1024.476 | 902.898 | 697.894 | 386.419 | 417.208 | 434.009 |
| 1444-1040 | 0.000 | 328.704 | 998.065 | 1441.786 | 1095.197 | 1063.173 | 970.873 | 687.933 | 487.884 | 860.448 |
| 1444-1042 | 0.000 | 59.305 | 914.945 | 1482.359 | 1310.794 | 1158.537 | 978.352 | 504.541 | 600.449 | 788.240 |
| 1444-1051 | 0.000 | 509.883 | 1240.897 | 953.447 | 793.118 | 732.686 | 547.741 | 382.217 | 366.964 | 435.770 |
| 1444-1052 | 0.000 | 350.200 | 841.426 | 1093.027 | 1319.899 | 1019.020 | 729.002 | 529.976 | 486.724 | 504.273 |
| 1444-1057 | 0.000 | 760.436 | 1403.846 | 1237.637 | 902.344 | 1025.043 | 700.088 | 531.908 | 523.762 | 547.776 |
| 1444-1058 | 0.000 | 488.450 | 1344.723 | 1241.830 | 889.579 | 844.899 | 513.445 | 700.302 | 397.419 | 534.139 |
| N | 8 | 8 | 8 | 8 | 8 | 8 | 8 | 8 | 8 | 8 |
| Mean | 0.000 | 410.586 | 1063.786 | 1147.525 | 974.335 | 928.558 | 693.339 | 498.772 | 452.035 | 598.327 |
| SD | 0.000 | 197.553 | 235.829 | 258.626 | 282.901 | 166.997 | 204.878 | 150.468 | 88.307 | 160.675 |
| SEM | 0.000 | 69.846 | 83.378 | 91.438 | 100.021 | 59.042 | 72.435 | 53.198 | 31.221 | 56.807 |
| Min | 0.000 | 59.305 | 777.766 | 703.373 | 459.276 | 682.206 | 409.319 | 266.879 | 335.869 | 434.009 |
| Median | 0.000 | 393.854 | 993.343 | 1165.332 | 963.410 | 960.959 | 698.991 | 517.259 | 451.966 | 540.958 |
| Max | 0.000 | 760.436 | 1403.846 | 1482.359 | 1319.899 | 1158.537 | 978.352 | 700.302 | 600.449 | 860.448 |
| % CV | NA | 48 | 22 | 23 | 29 | 18 | 30 | 30 | 20 | 27 |
| GM | NA | 344.890 | 1041.459 | 1119.787 | 931.654 | 914.828 | 666.511 | 477.461 | 444.581 | 580.567 |

NA: Not Applicable;

GM: Geometric Mean

TABLE 28A

Individual and Mean Plasma Concentrations (ng/mL) of XL184 by LC/MS/MS Method Following a Single 175 mg Oral Administration of XL184 (L-Malate Salt) Containing [$^{14}$C]-XL184 (100 µCi) to Healthy Male Subjects
48-648 hrs

| | Time (hours) | | | | | | | | | |
|---|---|---|---|---|---|---|---|---|---|---|
| Subject | 48.00 | 72.00 | 120.00 | 144.00 | 168.00 | 240.00 | 336.00 | 408.00 | 504.00 | 648.00 |
| 1444-1010 | 283.853 | 254.530 | 156.488 | 122.688 | 163.095 | 90.153 | 65.102 | 43.328 | 27.834 | 10.464 |
| 1444-1023 | 333.638 | 255.041 | 147.087 | 145.915 | 135.606 | 49.766 | 35.903 | 21.636 | 13.009 | 6.311 |
| 1444-1040 | 489.217 | 246.732 | 179.421 | 172.821 | 134.168 | 55.790 | 24.788 | 10.908 | 5.771 | 2.424 |
| 1444-1042 | 614.498 | 411.177 | 148.076 | 107.202 | 75.695 | 39.898 | 10.711 | 4.879 | 1.968 | 0.000 |
| 1444-1051 | 424.868 | 305.315 | 154.063 | 125.163 | 121.433 | 71.462 | 39.049 | 25.305 | 14.396 | 8.189 |
| 1444-1052 | 352.213 | 255.189 | 118.584 | 114.427 | 97.118 | 65.257 | 38.068 | 17.412 | 11.462 | 3.790 |
| 1444-1057 | 307.958 | 244.280 | 113.195 | 116.918 | 92.425 | 44.384 | 19.250 | 10.002 | 3.954 | 2.050 |
| 1444-1058 | 516.059 | 418.464 | 184.363 | 162.622 | 115.395 | 61.247 | 24.467 | 10.756 | 6.704 | 2.270 |
| N | 8 | 8 | 8 | 8 | 8 | 8 | 8 | 8 | 8 | 8 |
| Mean | 415.288 | 298.841 | 150.160 | 133.470 | 116.867 | 59.745 | 32.167 | 18.028 | 10.637 | 4.437 |
| SD | 116.396 | 74.114 | 25.238 | 24.098 | 28.013 | 16.211 | 16.569 | 12.232 | 8.239 | 3.555 |
| SEM | 41.152 | 26.203 | 8.923 | 8.520 | 9.904 | 5.732 | 5.858 | 4.325 | 2.913 | 1.257 |
| Min | 283.853 | 244.280 | 113.195 | 107.202 | 75.695 | 39.898 | 10.711 | 4.879 | 1.968 | 0.000 |
| Median | 388.541 | 255.115 | 151.070 | 123.926 | 118.414 | 58.519 | 30.346 | 14.160 | 9.083 | 3.107 |
| Max | 614.498 | 418.464 | 184.363 | 172.821 | 163.095 | 90.153 | 65.102 | 43.328 | 27.834 | 10.464 |
| % CV | 28 | 25 | 17 | 18 | 24 | 27 | 52 | 68 | 77 | 80 |
| GM | 401.634 | 291.722 | 148.236 | 131.665 | 113.863 | 57.917 | 28.494 | 14.850 | 8.070 | NA |

NA: Not Applicable;
GM: Geometric Mean

TABLE 29

Individual and Mean Plasma Concentrations (ng/mL) of XL184 Half-Dimer by LC/MS/MS Method Following a Single 175 mg Oral Administration of XL184 (L-Malate Salt) Containing [$^{14}$C]-XL184 (100 µCi) to Healthy Male Subjects
0-24 hrs

| | Time (hours) | | | | | | | | | |
|---|---|---|---|---|---|---|---|---|---|---|
| Subject | 0.00 | 0.50 | 1.00 | 2.00 | 3.00 | 4.00 | 5.00 | 8.00 | 14.00 | 24.00 |
| 1444-1010 | 0.000 | 4.846 | 13.450 | 23.314 | 24.221 | 27.171 | 24.260 | 22.875 | 31.511 | 35.627 |
| 1444-1023 | 0.000 | 4.593 | 17.564 | 31.523 | 33.843 | 34.651 | 35.617 | 38.445 | 37.909 | 37.924 |
| 1444-1040 | 0.000 | 4.531 | 14.478 | 27.120 | 29.439 | 32.345 | 32.584 | 28.090 | 34.054 | 35.050 |
| 1444-1042 | 0.000 | 0.000 | 17.132 | 43.143 | 52.416 | 54.336 | 76.749 | 63.237 | 68.777 | 75.680 |
| 1444-1051 | 0.000 | 4.356 | 17.489 | 28.961 | 31.495 | 36.085 | 36.373 | 38.175 | 40.841 | 35.055 |
| 1444-1052 | 0.000 | 4.261 | 21.194 | 35.430 | 44.061 | 49.890 | 55.705 | 63.530 | 65.263 | 67.985 |
| 1444-1057 | 0.000 | 8.367 | 24.937 | 37.927 | 38.602 | 51.831 | 50.493 | 57.434 | 69.700 | 69.776 |
| 1444-1058 | 0.000 | 6.794 | 23.881 | 35.764 | 38.359 | 42.571 | 43.260 | 58.592 | 47.769 | 56.247 |
| N | 8 | 8 | 8 | 8 | 8 | 8 | 8 | 8 | 8 | 8 |
| Mean | 0.000 | 4.719 | 18.766 | 32.898 | 36.555 | 41.110 | 44.380 | 46.297 | 49.478 | 51.668 |
| SD | 0.000 | 2.399 | 4.184 | 6.409 | 8.873 | 10.051 | 16.473 | 16.331 | 16.047 | 17.688 |
| SEM | 0.000 | 0.848 | 1.479 | 2.266 | 3.137 | 3.554 | 5.824 | 5.774 | 5.674 | 6.254 |
| Min | 0.000 | 0.000 | 13.450 | 23.314 | 24.221 | 27.171 | 24.260 | 22.875 | 31.511 | 35.050 |
| Median | 0.000 | 4.562 | 17.527 | 33.477 | 36.101 | 39.328 | 39.817 | 47.940 | 44.305 | 47.086 |
| Max | 0.000 | 8.367 | 24.937 | 43.143 | 52.416 | 54.336 | 76.749 | 63.530 | 69.700 | 75.680 |
| % CV | NA | 51 | 22 | 19 | 24 | 24 | 37 | 35 | 32 | 34 |
| GM | NA | NA | 18.364 | 32.341 | 35.633 | 40.015 | 41.935 | 43.470 | 47.247 | 49.053 |

NA: Not Applicable;
GM: Geometric Mean

TABLE 29A

Individual and Mean Plasma Concentrations (ng/mL) of XL184 Half-Dimer by LC/MS/MS Method Following a Single 175 mg Oral Administration of XL184 (L-Malate Salt) Containing [$^{14}$C]-XL184 (100 µCi) to Healthy Male Subjects
48-648 hrs

| | Time (hours) | | | | | | | | | |
|---|---|---|---|---|---|---|---|---|---|---|
| Subject | 48.00 | 72.00 | 120.00 | 144.00 | 168.00 | 240.00 | 336.00 | 408.00 | 504.00 | 648.00 |
| 1444-1010 | 30.648 | 24.554 | 18.190 | 14.057 | 11.729 | 7.495 | 5.228 | 2.998 | 2.084 | 0.000 |
| 1444-1023 | 36.546 | 24.587 | 16.438 | 15.153 | 12.065 | 5.903 | 2.034 | 1.806 | 1.083 | 0.000 |
| 1444-1040 | 26.242 | 19.464 | 11.095 | 9.729 | 8.353 | 2.927 | 1.209 | 0.000 | 0.000 | 0.000 |

TABLE 29A-continued

Individual and Mean Plasma Concentrations (ng/mL) of XL184 Half-Dimer by LC/MS/MS Method Following a Single 175 mg Oral Administration of XL184 (L-Malate Salt) Containing [$^{14}$C]-XL184 (100 μCi) to Healthy Male Subjects
48-648 hrs

| Subject | Time (hours) | | | | | | | | | |
|---|---|---|---|---|---|---|---|---|---|---|
| | 48.00 | 72.00 | 120.00 | 144.00 | 168.00 | 240.00 | 336.00 | 408.00 | 504.00 | 648.00 |
| 1444-1042 | 56.997 | 42.700 | 17.753 | 13.747 | 9.922 | 4.398 | 1.547 | 0.000 | 0.000 | 0.000 |
| 1444-1051 | 33.055 | 23.197 | 13.375 | 11.927 | 12.076 | 7.066 | 3.887 | 2.509 | 1.813 | 0.000 |
| 1444-1052 | 56.829 | 46.257 | 21.732 | 19.455 | 16.224 | 8.332 | 5.513 | 2.769 | 1.445 | 0.000 |
| 1444-1057 | 53.673 | 44.053 | 23.839 | 20.401 | 17.365 | 7.257 | 3.352 | 2.045 | 0.000 | 0.000 |
| 1444-1058 | 48.913 | 35.430 | 25.809 | 23.143 | 16.260 | 8.677 | 3.578 | 1.740 | 0.000 | 0.000 |
| N | 8 | 8 | 8 | 8 | 8 | 8 | 8 | 8 | 8 | 8 |
| Mean | 42.863 | 32.530 | 18.529 | 15.952 | 12.999 | 6.507 | 3.294 | 1.733 | 0.803 | 0.000 |
| SD | 12.592 | 10.807 | 5.048 | 4.595 | 3.262 | 1.983 | 1.607 | 1.158 | 0.905 | 0.000 |
| SEM | 4.452 | 3.821 | 1.785 | 1.625 | 1.153 | 0.701 | 0.568 | 0.409 | 0.320 | 0.000 |
| Min | 26.242 | 19.464 | 11.095 | 9.729 | 8.353 | 2.927 | 1.209 | 0.000 | 0.000 | 0.000 |
| Median | 42.730 | 30.009 | 17.972 | 14.605 | 12.071 | 7.162 | 3.465 | 1.926 | 0.542 | 0.000 |
| Max | 56.997 | 46.257 | 25.809 | 23.143 | 17.365 | 8.677 | 5.513 | 2.998 | 2.084 | 0.000 |
| % CV | 29 | 33 | 27 | 29 | 25 | 30 | 49 | 67 | 113 | NA |
| GM | 41.175 | 30.943 | 17.899 | 15.374 | 12.633 | 6.174 | 2.908 | NA | NA | NA |

NA: Not Applicable;
GM: Geometric Mean

TABLE 30

Individual and Mean Plasma Concentrations (ng/mL) of XL184-N-Oxide by LC/MS/MS Method Following a Single 175 mg Oral Administration of XL184 (L-Malate Salt) Containing [$^{14}$C]-XL184 (100 μCi) to Healthy Male Subjects
0-24 hrs

| Subject | Time (hours) | | | | | | | | | |
|---|---|---|---|---|---|---|---|---|---|---|
| | 0.00 | 0.50 | 1.00 | 2.00 | 3.00 | 4.00 | 5.00 | 8.00 | 14.00 | 24.00 |
| 1444-1010 | 0.000 | 11.529 | 42.306 | 49.777 | 46.221 | 57.466 | 38.445 | 33.122 | 25.454 | 64.769 |
| 1444-1023 | 0.000 | 15.944 | 47.387 | 65.128 | 82.005 | 78.375 | 78.220 | 67.430 | 63.633 | 101.490 |
| 1444-1040 | 0.000 | 17.041 | 82.525 | 149.634 | 167.092 | 150.220 | 135.223 | 125.712 | 140.835 | 178.702 |
| 1444-1042 | 0.000 | 1.789 | 40.311 | 104.019 | 108.484 | 115.106 | 103.517 | 66.642 | 73.090 | 129.577 |
| 1444-1051 | 0.000 | 13.441 | 67.257 | 94.858 | 92.250 | 91.248 | 79.258 | 68.805 | 66.930 | 84.372 |
| 1444-1052 | 0.000 | 14.585 | 67.753 | 103.201 | 134.615 | 124.375 | 89.247 | 85.963 | 71.593 | 84.326 |
| 1444-1057 | 0.000 | 27.247 | 92.619 | 113.541 | 90.538 | 111.017 | 86.573 | 79.003 | 80.870 | 93.700 |
| 1444-1058 | 0.000 | 20.854 | 97.364 | 128.577 | 118.153 | 125.842 | 88.903 | 115.660 | 68.937 | 113.468 |
| N | 8 | 8 | 8 | 8 | 8 | 8 | 8 | 8 | 8 | 8 |
| Mean | 0.000 | 15.304 | 67.190 | 101.092 | 104.920 | 106.706 | 87.423 | 80.292 | 73.918 | 106.301 |
| SD | 0.000 | 7.346 | 22.445 | 32.172 | 36.397 | 29.586 | 26.993 | 29.414 | 31.759 | 35.266 |
| SEM | 0.000 | 2.597 | 7.935 | 11.375 | 12.868 | 10.460 | 9.543 | 10.400 | 11.229 | 12.468 |
| Min | 0.000 | 1.789 | 40.311 | 49.777 | 46.221 | 57.466 | 38.445 | 33.122 | 25.454 | 64.769 |
| Median | 0.000 | 15.265 | 67.505 | 103.610 | 100.367 | 113.062 | 87.738 | 73.904 | 70.265 | 97.595 |
| Max | 0.000 | 27.247 | 97.364 | 149.634 | 167.092 | 150.220 | 135.223 | 125.712 | 140.835 | 178.702 |
| % CV | NA | 48 | 33 | 32 | 35 | 28 | 31 | 37 | 43 | 33 |
| GM | NA | 12.572 | 63.787 | 95.996 | 98.865 | 102.671 | 83.180 | 75.094 | 67.779 | 101.778 |

NA: Not Applicable;
GM: Geometric Mean

TABLE 30A

Individual and Mean Plasma Concentrations (ng/mL) of XL184-N-Oxide by LC/MS/MS Method Following a Single 175 mg Oral Administration of XL184 (L-Malate Salt) Containing [$^{14}$C]-XL184 (100 μCi) to Healthy Male Subjects
48-648 hrs

| Subject | Time (hours) | | | | | | | | | |
|---|---|---|---|---|---|---|---|---|---|---|
| | 48.00 | 72.00 | 120.00 | 144.00 | 168.00 | 240.00 | 336.00 | 408.00 | 504.00 | 648.00 |
| 1444-1010 | 29.036 | 28.612 | 21.842 | 13.355 | 13.351 | 7.415 | 4.583 | 3.326 | 1.817 | 1.062 |
| 1444-1023 | 64.132 | 40.828 | 19.980 | 19.507 | 14.871 | 5.771 | 2.530 | 1.964 | 0.000 | 0.000 |
| 1444-1040 | 116.958 | 82.612 | 51.850 | 35.583 | 26.090 | 10.327 | 4.459 | 1.674 | 1.094 | 0.000 |
| 1444-1042 | 90.059 | 63.663 | 20.037 | 13.485 | 10.109 | 4.830 | 1.199 | 0.000 | 0.000 | 0.000 |
| 1444-1051 | 69.537 | 47.911 | 25.291 | 19.696 | 18.011 | 9.570 | 5.079 | 3.200 | 2.005 | 0.000 |
| 1444-1052 | 50.889 | 33.767 | 16.002 | 11.804 | 9.229 | 6.267 | 2.973 | 1.678 | 1.052 | 0.000 |

TABLE 30A-continued

Individual and Mean Plasma Concentrations (ng/mL) of XL184-N-Oxide by LC/MS/MS Method Following a Single 175 mg Oral Administration of XL184 (L-Malate Salt) Containing [$^{14}$C]-XL184 (100 µCi) to Healthy Male Subjects 48-648 hrs

| Subject | Time (hours) | | | | | | | | | |
|---|---|---|---|---|---|---|---|---|---|---|
| | 48.00 | 72.00 | 120.00 | 144.00 | 168.00 | 240.00 | 336.00 | 408.00 | 504.00 | 648.00 |
| 1444-1057 | 49.764 | 40.895 | 21.335 | 17.057 | 14.433 | 5.546 | 2.390 | 1.382 | 0.000 | 0.000 |
| 1444-1058 | 89.002 | 76.099 | 31.817 | 30.113 | 19.166 | 9.684 | 4.176 | 1.946 | 1.237 | 0.000 |
| N | 8 | 8 | 8 | 8 | 8 | 8 | 8 | 8 | 8 | 8 |
| Mean | 69.922 | 51.798 | 26.019 | 20.075 | 15.658 | 7.426 | 3.424 | 1.896 | 0.901 | 0.133 |
| SD | 27.918 | 19.992 | 11.423 | 8.517 | 5.428 | 2.154 | 1.349 | 1.049 | 0.816 | 0.375 |
| SEM | 9.870 | 7.068 | 4.039 | 3.011 | 1.919 | 0.761 | 0.477 | 0.371 | 0.289 | 0.133 |
| Min | 29.036 | 28.612 | 16.002 | 11.804 | 9.229 | 4.830 | 1.199 | 0.000 | 0.000 | 0.000 |
| Median | 66.835 | 44.403 | 21.589 | 18.282 | 14.652 | 6.841 | 3.575 | 1.812 | 1.073 | 0.000 |
| Max | 116.958 | 82.612 | 51.850 | 35.583 | 26.090 | 10.327 | 5.079 | 3.326 | 2.005 | 1.062 |
| % CV | 40 | 39 | 44 | 42 | 35 | 29 | 39 | 55 | 91 | 283 |
| GM | 64.709 | 48.563 | 24.374 | 18.696 | 14.883 | 7.156 | 3.136 | NA | NA | NA |

NA: Not Applicable;
GM: Geometric Mean

TABLE 31

Individual and Mean Plasma Concentrations (ng/mL) of XL184-Sulfate by LC/MS/MS Method Following a Single 175 mg Oral Administration of XL184 (L-Malate Salt) Containing [$^{14}$C]-XL184 (100 µCi) to Healthy Male Subjects 0-24 hrs

| Subject | Time (hours) | | | | | | | | | |
|---|---|---|---|---|---|---|---|---|---|---|
| | 0.00 | 0.50 | 1.00 | 2.00 | 3.00 | 4.00 | 5.00 | 8.00 | 14.00 | 24.00 |
| 1444-1010 | 0.000 | 26.136 | 53.208 | 75.013 | 69.493 | 92.232 | 65.650 | 37.746 | 34.395 | 112.189 |
| 1444-1023 | 0.000 | 39.062 | 88.742 | 138.826 | 158.824 | 179.491 | 172.724 | 130.798 | 131.091 | 233.292 |
| 1444-1040 | 0.000 | 45.896 | 145.829 | 249.626 | 310.748 | 267.057 | 283.604 | 197.270 | 268.052 | 306.497 |
| 1444-1042 | 0.000 | 6.360 | 78.291 | 157.511 | 203.331 | 205.443 | 243.196 | 98.885 | 127.544 | 287.276 |
| 1444-1051 | 0.000 | 29.730 | 96.816 | 126.368 | 141.682 | 148.181 | 125.679 | 108.976 | 133.704 | 174.720 |
| 1444-1052 | 0.000 | 32.267 | 120.212 | 157.200 | 194.021 | 215.476 | 174.760 | 143.215 | 153.538 | 205.532 |
| 1444-1057 | 0.000 | 59.658 | 156.410 | 180.378 | 187.282 | 226.697 | 174.947 | 159.230 | 198.553 | 262.691 |
| 1444-1058 | 0.000 | 43.796 | 143.662 | 181.953 | 231.546 | 216.139 | 162.694 | 204.329 | 153.379 | 289.913 |
| N | 8 | 8 | 8 | 8 | 8 | 8 | 8 | 8 | 8 | 8 |
| Mean | 0.000 | 35.363 | 110.396 | 158.359 | 187.116 | 193.840 | 175.407 | 135.056 | 150.032 | 234.014 |
| SD | 0.000 | 15.828 | 36.898 | 50.320 | 69.969 | 53.659 | 66.538 | 54.506 | 66.343 | 66.769 |
| SEM | 0.000 | 5.596 | 13.045 | 17.791 | 24.738 | 18.971 | 23.525 | 19.271 | 23.456 | 23.606 |
| Min | 0.000 | 6.360 | 53.208 | 75.013 | 69.493 | 92.232 | 65.650 | 37.746 | 34.395 | 112.189 |
| Median | 0.000 | 35.665 | 108.514 | 157.356 | 190.652 | 210.460 | 173.742 | 137.007 | 143.542 | 247.992 |
| Max | 0.000 | 59.658 | 156.410 | 249.626 | 310.748 | 267.057 | 283.604 | 204.329 | 268.052 | 306.497 |
| % CV | NA | 45 | 33 | 32 | 37 | 28 | 38 | 40 | 44 | 29 |
| GM | NA | 30.490 | 104.387 | 150.767 | 173.768 | 185.812 | 162.613 | 121.946 | 132.738 | 223.841 |

NA: Not Applicable;
GM: Geometric Mean

TABLE 31A

Individual and Mean Plasma Concentrations (ng/mL) of XL184-Sulfate by LC/MS/MS Method Following a Single 175 mg Oral Administration of XL184 (L-Malate Salt) Containing [$^{14}$C]-XL184 (100 µCi) to Healthy Male Subjects 48-648 hrs

| Subject | Time (hrs) | | | | | | | | | |
|---|---|---|---|---|---|---|---|---|---|---|
| | 48.00 | 72.00 | 120.00 | 144.00 | 168.00 | 240.00 | 336.00 | 408.00 | 504.00 | 648.00 |
| 1444-1010 | 45.563 | 50.547 | 46.211 | 27.744 | 23.691 | 11.649 | 8.367 | 5.228 | 0.000 | 0.000 |
| 1444-1023 | 146.630 | 132.711 | 90.680 | 85.890 | 73.594 | 26.053 | 9.824 | 5.311 | 0.000 | 0.000 |
| 1444-1040 | 230.932 | 198.580 | 156.507 | 125.712 | 112.019 | 47.012 | 18.863 | 9.010 | 4.723 | 0.000 |
| 1444-1042 | 220.082 | 185.825 | 81.561 | 61.841 | 46.492 | 21.297 | 5.717 | 0.000 | 0.000 | 0.000 |
| 1444-1051 | 176.870 | 152.441 | 95.518 | 73.454 | 73.048 | 36.170 | 20.502 | 13.626 | 7.874 | 4.167 |
| 1444-1052 | 130.352 | 106.815 | 47.419 | 37.916 | 27.883 | 16.190 | 10.596 | 4.971 | 0.000 | 0.000 |
| 1444-1057 | 147.459 | 151.276 | 89.982 | 80.113 | 61.829 | 30.106 | 11.580 | 6.347 | 0.000 | 0.000 |
| 1444-1058 | 258.933 | 211.280 | 149.901 | 151.619 | 97.444 | 49.589 | 22.349 | 8.128 | 4.996 | 0.000 |
| N | 8 | 8 | 8 | 8 | 8 | 8 | 8 | 8 | 8 | 8 |

TABLE 31A-continued

Individual and Mean Plasma Concentrations (ng/mL) of XL184-Sulfate by LC/MS/MS Method Following a Single 175 mg Oral Administration of XL184 (L-Malate Salt) Containing [$^{14}$C]-XL184 (100 µCi) to Healthy Male Subjects 48-648 hrs

| Subject | Time (hrs) | | | | | | | | | |
|---|---|---|---|---|---|---|---|---|---|---|
| | 48.00 | 72.00 | 120.00 | 144.00 | 168.00 | 240.00 | 336.00 | 408.00 | 504.00 | 648.00 |
| Mean | 169.603 | 148.684 | 94.722 | 80.536 | 64.500 | 29.758 | 13.475 | 6.578 | 2.199 | 0.521 |
| SD | 67.915 | 52.708 | 40.823 | 41.620 | 31.252 | 13.782 | 6.195 | 3.916 | 3.175 | 1.473 |
| SEM | 24.011 | 18.635 | 14.433 | 14.715 | 11.049 | 4.873 | 2.190 | 1.384 | 1.123 | 0.521 |
| Min | 45.563 | 50.547 | 46.211 | 27.744 | 23.691 | 11.649 | 5.717 | 0.000 | 0.000 | 0.000 |
| Median | 162.165 | 151.859 | 90.331 | 76.784 | 67.439 | 28.080 | 11.088 | 5.829 | 0.000 | 0.000 |
| Max | 258.933 | 211.280 | 156.507 | 151.619 | 112.019 | 49.589 | 22.349 | 13.626 | 7.874 | 4.167 |
| % CV | 40 | 35 | 43 | 52 | 48 | 46 | 46 | 60 | 144 | 283 |
| GM | 152.912 | 137.642 | 86.953 | 70.735 | 57.000 | 26.794 | 12.223 | NA | NA | NA |

NA: Not Applicable;
GM: Geometric Mean

TABLE 32

Individual and Mean Plasma Concentrations (ng/mL) of 6-Demethyl Half-Dimer Sulfate by LC/MS/MS Method Following a Single 175 mg Oral Administration of XL184 (L-Malate Salt) Containing [$^{14}$C]-XL184 (100 µCi) to Healthy Male Subjects 0-24 hrs

| Subject | Time (hours) | | | | | | | | | |
|---|---|---|---|---|---|---|---|---|---|---|
| | 0.00 | 0.50 | 1.00 | 2.00 | 3.00 | 4.00 | 5.00 | 8.00 | 14.00 | 24.00 |
| 1444-1010 | 0.000 | 0.000 | 0.000 | 0.000 | 3.386 | 5.641 | 8.608 | 15.507 | 34.150 | 51.405 |
| 1444-1023 | 0.000 | 0.000 | 0.000 | 2.592 | 6.599 | 11.121 | 15.479 | 32.187 | 47.455 | 99.900 |
| 1444-1040 | 0.000 | 0.000 | 0.000 | 0.000 | 2.692 | 3.416 | 6.003 | 10.485 | 18.220 | 27.408 |
| 1444-1042 | 0.000 | 0.000 | 0.000 | 2.376 | 6.406 | 11.906 | 19.210 | 40.794 | 76.906 | 141.432 |
| 1444-1051 | 0.000 | 0.000 | 0.000 | 2.132 | 5.610 | 8.166 | 12.887 | 24.346 | 50.905 | 71.492 |
| 1444-1052 | 0.000 | 0.000 | 0.000 | 0.000 | 3.763 | 6.466 | 10.265 | 23.612 | 54.607 | 79.917 |
| 1444-1057 | 0.000 | 0.000 | 0.000 | 0.000 | 3.139 | 5.576 | 8.199 | 17.826 | 44.580 | 71.085 |
| 1444-1058 | 0.000 | 0.000 | 0.000 | 2.672 | 6.542 | 10.442 | 16.258 | 31.365 | 69.308 | 107.045 |
| N | 8 | 8 | 8 | 8 | 8 | 8 | 8 | 8 | 8 | 8 |
| Mean | 0.000 | 0.000 | 0.000 | 1.222 | 4.767 | 7.842 | 12.114 | 24.515 | 49.516 | 81.211 |
| SD | 0.000 | 0.000 | 0.000 | 1.315 | 1.681 | 3.061 | 4.595 | 9.960 | 18.570 | 35.102 |
| SEM | 0.000 | 0.000 | 0.000 | 0.465 | 0.594 | 1.082 | 1.625 | 3.521 | 6.566 | 12.410 |
| Min | 0.000 | 0.000 | 0.000 | 0.000 | 2.692 | 3.416 | 6.003 | 10.485 | 18.220 | 27.408 |
| Median | 0.000 | 0.000 | 0.000 | 1.066 | 4.687 | 7.316 | 11.576 | 23.979 | 49.180 | 75.705 |
| Max | 0.000 | 0.000 | 0.000 | 2.672 | 6.599 | 11.906 | 19.210 | 40.794 | 76.906 | 141.432 |
| % CV | NA | NA | NA | 108 | 35 | 39 | 38 | 41 | 38 | 43 |
| GM | NA | NA | NA | NA | 4.496 | 7.275 | 11.327 | 22.623 | 45.842 | 73.647 |

NA: Not Applicable;
GM: Geometric Mean

TABLE 32A

Individual and Mean Plasma Concentrations (ng/mL) of 6-Demethyl Half-Dimer Sulfate by LC/MS/MS Method Following a Single 175 mg Oral Administration of XL184 (L-Malate Salt) Containing [$^{14}$C]-XL184 (100 µCi) to Healthy Male Subjects 48-648 hrs

| Subject | Time (hrs) | | | | | | | | | |
|---|---|---|---|---|---|---|---|---|---|---|
| | 48.00 | 72.00 | 120.00 | 144.00 | 168.00 | 240.00 | 336.00 | 408.00 | 504.00 | 648.00 |
| 1444-1010 | 84.732 | 122.418 | 164.550 | 168.502 | 174.221 | 159.028 | 158.082 | 144.822 | 127.233 | 97.753 |
| 1444-1023 | 141.710 | 176.888 | 212.151 | 207.554 | 215.785 | 198.217 | 177.675 | 135.964 | 125.529 | 108.334 |
| 1444-1040 | 49.742 | 59.747 | 72.988 | 67.894 | 85.113 | 66.807 | 59.122 | 46.038 | 39.328 | 29.436 |
| 1444-1042 | 223.640 | 323.165 | 247.344 | 250.230 | 267.533 | 212.848 | 186.228 | 150.688 | 141.540 | 107.324 |
| 1444-1051 | 146.757 | 146.869 | 154.952 | 157.981 | 173.296 | 176.893 | 133.908 | 136.789 | 121.149 | 105.230 |
| 1444-1052 | 149.399 | 208.455 | 242.883 | 243.269 | 274.906 | 245.792 | 222.108 | 179.242 | 162.042 | 157.284 |
| 1444-1057 | 117.309 | 162.565 | 179.245 | 188.012 | 215.041 | 170.955 | 150.313 | 120.915 | 121.615 | 104.173 |
| 1444-1058 | 218.918 | 271.897 | 311.399 | 288.310 | 371.830 | 297.836 | 225.057 | 208.293 | 202.228 | 143.171 |
| N | 8 | 8 | 8 | 8 | 8 | 8 | 8 | 8 | 8 | 8 |
| Mean | 141.526 | 184.001 | 198.189 | 196.469 | 222.216 | 191.047 | 164.062 | 140.344 | 130.083 | 106.588 |
| SD | 59.831 | 83.504 | 72.171 | 68.143 | 85.190 | 67.604 | 53.336 | 47.147 | 45.942 | 37.702 |
| SEM | 21.153 | 29.523 | 25.516 | 24.092 | 30.119 | 23.902 | 18.857 | 16.669 | 16.243 | 13.330 |

TABLE 32A-continued

Individual and Mean Plasma Concentrations (ng/mL) of 6-Demethyl Half-Dimer Sulfate by LC/MS/MS Method Following a Single 175 mg Oral Administration of XL184 (L-Malate Salt) Containing [$^{14}$C]-XL184 (100 μCi) to Healthy Male Subjects 48-648 hrs

| | Time (hrs) | | | | | | | | | |
|---|---|---|---|---|---|---|---|---|---|---|
| Subject | 48.00 | 72.00 | 120.00 | 144.00 | 168.00 | 240.00 | 336.00 | 408.00 | 504.00 | 648.00 |
| Min | 49.742 | 59.747 | 72.988 | 67.894 | 85.113 | 66.807 | 59.122 | 46.038 | 39.328 | 29.436 |
| Median | 144.234 | 169.727 | 195.698 | 197.783 | 215.413 | 187.555 | 167.879 | 140.806 | 126.381 | 106.277 |
| Max | 223.640 | 323.165 | 311.399 | 288.310 | 371.830 | 297.836 | 225.057 | 208.293 | 202.228 | 157.284 |
| % CV | 42 | 45 | 36 | 35 | 38 | 35 | 33 | 34 | 35 | 35 |
| GM | 128.687 | 165.608 | 184.175 | 182.634 | 206.142 | 177.656 | 153.681 | 130.546 | 119.974 | 97.637 |

NA: Not Applicable;
GM: Geometric Mean

TABLE 33

Individual and Descriptive Statistics of XL184 Plasma Pharmacokinetic Parameters by LC/MS/MS Method Following a Single 175 mg Oral Administration of XL184 (L-Malate Salt) Containing [$^{14}$C]-XL184 (100 μCi) to Healthy Male Subjects

| Subject | $C_{max}$ (ng/mL) | $t_{max}$ (h) | $AUC_{0-24}$ (h · ng/mL) | $AUC_{0-72}$ (h · ng/mL) | $AUC_{0-t}$ (h · ng/mL) | $AUC_{0-inf}$ (h · ng/mL) | $k_{el}$ (1/h) | $t_{1/2}$ (h) | Ratio[a] (%) |
|---|---|---|---|---|---|---|---|---|---|
| 1444-1010 | 778 | 1.00 | 10700 | 28800 | 72100 | 73900 | 0.0058 | 119 | 39.5 |
| 1444-1023 | 1030 | 1.98 | 12500 | 28800 | 61300 | 62500 | 0.00512 | 135 | 30.2 |
| 1444-1040 | 1440 | 2.00 | 17800 | 42800 | 74300 | 74700 | 0.00625 | 111 | 43.3 |
| 1444-1042 | 1480 | 2.00 | 17600 | 46800 | 72900 | 73100 | 0.0101 | 69.0 | 30.7 |
| 1444-1051 | 1240 | 1.00 | 11600 | 30700 | 66100 | 67500 | 0.00575 | 121 | 33.0 |
| 1444-1052 | 1320 | 3.00 | 14500 | 32100 | 61700 | 62200 | 0.00675 | 103 | 27.6 |
| 1444-1057 | 1400 | 1.00 | 15300 | 32200 | 56200 | 56400 | 0.00862 | 80.4 | 29.2 |
| 1444-1058 | 1340 | 1.00 | 14300 | 38100 | 73300 | 73500 | 0.00856 | 81.0 | 25.6 |
| N | 8 | 8 | 8 | 8 | 8 | 8 | 8 | 8 | 8 |
| Mean | 1250 | 1.62 | 14300 | 35000 | 67200 | 68000 | 0.00712 | 102 | 32.4 |
| SD | 238 | 0.74 | 2600 | 6770 | 6880 | 6910 | 0.00176 | 23.3 | 6.07 |
| SEM | 84.1 | 0.26 | 919 | 2390 | 2430 | 2440 | 0.000623 | 8.25 | 2.15 |
| Min | 778 | 1.00 | 10700 | 28800 | 56200 | 56400 | 0.00512 | 69.0 | 25.6 |
| Median | 1330 | 1.49 | 14400 | 32100 | 69100 | 70300 | 0.0065 | 107 | 30.4 |
| Max | 1480 | 3.00 | 17800 | 46800 | 74300 | 74700 | 0.0101 | 135 | 43.3 |
| % CV | 19 | 46 | 18 | 19 | 10 | 10 | 25 | 23 | 19 |
| GM | 1230 | 1.49 | 14100 | 34500 | 66900 | 67700 | 0.00694 | 100 | 31.9 |

GM: Geometric Mean;
[a] ratio of $AUC_{0-t}$ (each analyte)/$AUC_{0-t}$ (parent + 4 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life;
CL/F, apparent total body clearance;
V/F, apparent total volume of distribution.

TABLE 33A

Individual and Descriptive Statistics of XL184-Half-Dimer Plasma Pharmacokinetic Parameters by LC/MS/MS Method Following a Single 175 mg Oral Administration of XL184 (L-Malate Salt) Containing [$^{14}$C]-XL184 (100 μCi) to Healthy Male Subjects

| Subject | $C_{max}$ (ng/mL) | $t_{max}$ (h) | $AUC_{0-24}$ (h · ng/mL) | $AUC_{0-72}$ (h · ng/mL) | $AUC_{0-t}$ (h · ng/mL) | Ratio[a] (%) | Ratio[b] (%) | $AUC_{0-inf}$ (h · ng/mL) | $k_{el}$ (1/h) | $t_{1/2}$ (h) |
|---|---|---|---|---|---|---|---|---|---|---|
| 1444-1010 | 35.6 | 24.00 | 669 | 2130 | 5690 | 7.89 | 3.11 | 6080 | 0.00531 | 131 |
| 1444-1023 | 38.4 | 7.98 | 853 | 2480 | 5470 | 8.92 | 2.69 | 5610 | 0.00786 | 88.2 |
| 1444-1040 | 35.1 | 24.03 | 741 | 2030 | 3830 | 5.15 | 2.23 | 3940 | 0.0108 | 64.2 |
| 1444-1042 | 76.7 | 5.00 | 1530 | 4320 | 7230 | 9.92 | 3.05 | 7370 | 0.0111 | 62.7 |
| 1444-1051 | 40.8 | 13.98 | 859 | 2350 | 5470 | 8.28 | 2.73 | 5800 | 0.00557 | 124 |
| 1444-1052 | 68.0 | 24.10 | 1410 | 4140 | 8740 | 14.2 | 3.90 | 8950 | 0.00708 | 97.9 |
| 1444-1057 | 69.8 | 24.08 | 1420 | 4070 | 8270 | 14.7 | 4.30 | 8550 | 0.00757 | 91.6 |
| 1444-1058 | 58.6 | 8.00 | 1150 | 3430 | 7630 | 10.4 | 2.66 | 7820 | 0.0093 | 74.5 |

TABLE 33A-continued

Individual and Descriptive Statistics of XL184-Half-Dimer Plasma Pharmacokinetic Parameters by LC/MS/MS Method Following a Single 175 mg Oral Administration of XL184 (L-Malate Salt) Containing [$^{14}$C]-XL184 (100 µCi) to Healthy Male Subjects

| Subject | $C_{max}$ (ng/mL) | $t_{max}$ (h) | $AUC_{0-24}$ (h · ng/mL) | $AUC_{0-72}$ (h · ng/mL) | $AUC_{0-t}$ (h · ng/mL) | Ratio$^a$ (%) | Ratio$^b$ (%) | $AUC_{0-inf}$ (h · ng/mL) | $k_{el}$ (1/h) | $t_{1/2}$ (h) |
|---|---|---|---|---|---|---|---|---|---|---|
| N | 8 | 8 | 8 | 8 | 8 | 8 | 8 | 8 | 8 | 8 |
| Mean | 52.9 | 16.40 | 1080 | 3120 | 6540 | 9.93 | 3.09 | 6770 | 0.00807 | 91.8 |
| SD | 17.3 | 8.55 | 341 | 976 | 1680 | 3.20 | 0.689 | 1700 | 0.00218 | 25.4 |
| SEM | 6.10 | 3.02 | 120 | 345 | 595 | 1.13 | 0.244 | 600 | 0.000771 | 9.00 |
| Min | 35.1 | 5.00 | 669 | 2030 | 3830 | 5.15 | 2.23 | 3940 | 0.00531 | 62.7 |
| Median | 49.7 | 18.99 | 1010 | 2950 | 6460 | 9.42 | 2.89 | 6730 | 0.00772 | 89.9 |
| Max | 76.7 | 24.10 | 1530 | 4320 | 8740 | 14.7 | 4.30 | 8950 | 0.0111 | 131 |
| % CV | 33 | 52 | 32 | 31 | 26 | 32 | 22 | 25 | 27 | 28 |
| GM | 50.4 | 14.02 | 1030 | 2980 | 6340 | 9.47 | 3.02 | 6560 | 0.00781 | 88.8 |

GM: Geometric Mean;
$^a$ratio of $AUC_{0-t}$ (metabolite)/$AUC_{0-t}$ (parent);
$^b$ratio of $AUC_{0-t}$ (each analyte)/$AUC_{0-t}$ (parent + 4 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life;
CL/F, apparent total body clearance;
V/F, apparent total volume of distribution.

TABLE 34

Individual and Descriptive Statistics of XL184-N-Oxide Plasma Pharmacokinetic Parameters by LC/MS/MS Method Following a Single 175 mg Oral Administration of XL184 (L-Malate Salt) Containing [$^{14}$C]-XL184 (100 µCi) to Healthy Male Subjects

| Subject | $C_{max}$ (ng/mL) | $t_{max}$ (h) | $AUC_{0-24}$ (h · ng/mL) | $AUC_{0-72}$ (h · ng/mL) | $AUC_{0-t}$ (h · ng/mL) | Ratio$^a$ (%) | Ratio$^b$ (%) | $AUC_{0-inf}$ (h · ng/mL) | $k_{el}$ (1/h) | $t_{1/2}$ (h) |
|---|---|---|---|---|---|---|---|---|---|---|
| 1444-1010 | 64.8 | 24.00 | 945 | 2760 | 6780 | 9.40 | 3.71 | 7000 | 0.00486 | 143 |
| 1444-1023 | 101 | 24.00 | 1750 | 4990 | 8640 | 14.1 | 4.25 | 8850 | 0.00928 | 74.7 |
| 1444-1040 | 179 | 24.03 | 3390 | 9340 | 16700 | 22.5 | 9.74 | 16800 | 0.0109 | 63.5 |
| 1444-1042 | 130 | 24.03 | 2100 | 6580 | 10100 | 13.9 | 4.26 | 10200 | 0.0126 | 54.8 |
| 1444-1051 | 94.9 | 2.00 | 1760 | 5020 | 10000 | 15.1 | 4.99 | 10300 | 0.00596 | 116 |
| 1444-1052 | 135 | 3.00 | 1980 | 4620 | 7700 | 12.5 | 3.44 | 7850 | 0.00684 | 101 |
| 1444-1057 | 114 | 2.00 | 2040 | 4850 | 8420 | 15.0 | 4.37 | 8590 | 0.0083 | 83.5 |
| 1444-1058 | 129 | 2.00 | 2280 | 6690 | 12700 | 17.3 | 4.44 | 12800 | 0.00895 | 77.4 |
| N | 8 | 8 | 8 | 8 | 8 | 8 | 8 | 8 | 8 | 8 |
| Mean | 118 | 13.13 | 2030 | 5610 | 10100 | 15.0 | 4.90 | 10300 | 0.00846 | 89.2 |
| SD | 33.7 | 11.64 | 682 | 1940 | 3210 | 3.80 | 2.01 | 3170 | 0.00256 | 29.2 |
| SEM | 11.9 | 4.11 | 241 | 686 | 1130 | 1.34 | 0.711 | 1120 | 0.000905 | 10.3 |
| Min | 64.8 | 2.00 | 945 | 2760 | 6780 | 9.40 | 3.44 | 7000 | 0.00486 | 54.8 |
| Median | 122 | 13.50 | 2010 | 5010 | 9320 | 14.5 | 4.31 | 9530 | 0.00863 | 80.5 |
| Max | 179 | 24.03 | 3390 | 9340 | 16700 | 22.5 | 9.74 | 16800 | 0.0126 | 143 |
| % CV | 28 | 89 | 34 | 35 | 32 | 25 | 41 | 31 | 30 | 33 |
| GM | 114 | 7.29 | 1930 | 5320 | 9750 | 14.6 | 4.65 | 9930 | 0.00811 | 85.3 |

GM: Geometric Mean;
$^a$ratio of $AUC_{0-t}$ (metabolite)/$AUC_{0-t}$ (parent);
$^b$ratio of $AUC_{0-t}$ (each analyte)/$AUC_{0-t}$ (parent + 4 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life;
CL/F, apparent total body clearance;
V/F, apparent total volume of distribution.

TABLE 35

Individual and Descriptive Statistics of XL184-Sulfate Plasma Pharmacokinetic Parameters by LC/MS/MS Method following a Single 175 mg Oral Administration of XL184 (L-Malate Salt) Containing [$^{14}$C]-XL184 (100 μCi) to Healthy Male Subjects

| Subject | $C_{max}$ (ng/mL) | $t_{max}$ (h) | $AUC_{0-24}$ (h·ng/mL) | $AUC_{0-72}$ (h·ng/mL) | $AUC_{0-t}$ (h·ng/mL) | Ratio[a] (%) | Ratio[b] (%) | $AUC_{0-inf}$ (h·ng/mL) | $k_{el}$ (1/h) | $t_{1/2}$ (h) |
|---|---|---|---|---|---|---|---|---|---|---|
| 1444-1010 | 112 | 24.00 | 1430 | 4470 | 11000 | 15.3 | 6.02 | 11900 | 0.00619 | 112 |
| 1444-1023 | 233 | 24.00 | 3710 | 11600 | 26900 | 43.9 | 13.2 | 27400 | 0.0095 | 72.9 |
| 1444-1040 | 311 | 3.00 | 6090 | 17700 | 43000 | 57.9 | 25.1 | 43500 | 0.00948 | 73.1 |
| 1444-1042 | 287 | 24.03 | 4020 | 15000 | 28100 | 38.5 | 11.8 | 28600 | 0.0122 | 56.8 |
| 1444-1051 | 177 | 48.00 | 3190 | 11400 | 30900 | 46.7 | 15.4 | 31700 | 0.00532 | 130 |
| 1444-1052 | 215 | 4.00 | 3920 | 10800 | 19700 | 31.9 | 8.80 | 20400 | 0.00734 | 94.4 |
| 1444-1057 | 263 | 24.08 | 4710 | 13200 | 28700 | 51.1 | 14.9 | 29400 | 0.00953 | 72.8 |
| 1444-1058 | 290 | 23.68 | 4700 | 16900 | 42700 | 58.3 | 14.9 | 43200 | 0.00913 | 75.9 |
| N | 8 | 8 | 8 | 8 | 8 | 8 | 8 | 8 | 8 | 8 |
| Mean | 236 | 21.85 | 3970 | 12600 | 28900 | 42.9 | 13.8 | 29500 | 0.00859 | 86.0 |
| SD | 66.7 | 14.04 | 1350 | 4180 | 10700 | 14.4 | 5.63 | 10600 | 0.00220 | 24.3 |
| SEM | 23.6 | 4.96 | 477 | 1480 | 3790 | 5.08 | 1.99 | 3750 | 0.000777 | 8.61 |
| Min | 112 | 3.00 | 1430 | 4470 | 11000 | 15.3 | 6.02 | 11900 | 0.00532 | 56.8 |
| Median | 248 | 24.00 | 3970 | 12400 | 28400 | 45.3 | 14.1 | 29000 | 0.00931 | 74.5 |
| Max | 311 | 48.00 | 6090 | 17700 | 43000 | 58.3 | 25.1 | 43500 | 0.0122 | 130 |
| % CV | 28 | 64 | 34 | 33 | 37 | 33 | 41 | 36 | 26 | 28 |
| GM | 226 | 16.11 | 3710 | 11800 | 26800 | 40.1 | 12.8 | 27600 | 0.00833 | 83.2 |

GM: Geometric Mean;
[a] ratio of $AUC_{0-t}$ (metabolite)/$AUC_{0-t}$ (parent);
[b] ratio of $AUC_{0-t}$ (each analyte)/$AUC_{0-t}$ (parent + 4 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life;
CL/F, apparent total body clearance;
V/F, apparent total volume of distribution.

TABLE 36

Individual and Descriptive Statistics of 6-Demethyl Half-Dimer Sulfate Plasma Pharmacokinetic Parameters by LC/MS/MS Method following a Single 175 mg Oral Administration of XL184 (L-Malate Salt) Containing [$^{14}$C]-XL184 (100 μCi) to Healthy Male Subjects

| Subject | $C_{max}$ (ng/mL) | $t_{max}$ (h) | $AUC_{0-24}$ (h·ng/mL) | $AUC_{0-72}$ (h·ng/mL) | $AUC_{0-t}$ (h·ng/mL) | Ratio[a] (%) | Ratio[b] (%) | $AUC_{0-inf}$ (h·ng/mL) | $k_{el}$ (1/h) | $t_{1/2}$ (h) |
|---|---|---|---|---|---|---|---|---|---|---|
| 1444-1010 | 174 | 168.00 | 627 | 4750 | 87100 | 121 | 47.7 | NR | NR | NR |
| 1444-1023 | 216 | 168.00 | 1080 | 7800 | 101000 | 165 | 49.7 | NR | NR | NR |
| 1444-1040 | 85.1 | 168.00 | 348 | 2590 | 33600 | 45.2 | 19.6 | NR | NR | NR |
| 1444-1042 | 323 | 71.97 | 1570 | 12500 | 119000 | 163 | 50.1 | NR | NR | NR |
| 1444-1051 | 177 | 240.00 | 916 | 7060 | 88000 | 133 | 43.9 | NR | NR | NR |
| 1444-1052 | 275 | 168.00 | 972 | 8020 | 126000 | 204 | 56.3 | NR | NR | NR |
| 1444-1057 | 215 | 168.00 | 816 | 6430 | 90900 | 162 | 47.2 | NR | NR | NR |
| 1444-1058 | 372 | 168.00 | 1290 | 11100 | 150000 | 205 | 52.4 | NR | NR | NR |
| N | 8 | 8 | 8 | 8 | 8 | 8 | 8 | NA | NA | NA |
| Mean | 230 | 165.00 | 951 | 7530 | 99500 | 150 | 45.9 | NA | NA | NA |
| SD | 91.2 | 45.25 | 377 | 3200 | 34500 | 51.5 | 11.2 | NA | NA | NA |
| SEM | 32.2 | 16.00 | 133 | 1130 | 12200 | 18.2 | 3.97 | NA | NA | NA |
| Min | 85.1 | 71.97 | 348 | 2590 | 33600 | 45.2 | 19.6 | NA | NA | NA |
| Median | 216 | 168.00 | 944 | 7430 | 96000 | 162 | 48.7 | NA | NA | NA |
| Max | 372 | 240.00 | 1570 | 12500 | 150000 | 205 | 56.3 | NA | NA | NA |

TABLE 36-continued

Individual and Descriptive Statistics of 6-Demethyl Half-Dimer Sulfate Plasma Pharmacokinetic Parameters by LC/MS/MS Method following a Single 175 mg Oral Administration of XL184 (L-Malate Salt) Containing [$^{14}$C]-XL184 (100 µCi) to Healthy Male Subjects

| Subject | $C_{max}$ (ng/mL) | $t_{max}$ (h) | $AUC_{0-24}$ (h · ng/mL) | $AUC_{0-72}$ (h · ng/mL) | $AUC_{0-t}$ (h · ng/mL) | Ratio$^a$ (%) | Ratio$^b$ (%) | $AUC_{0-inf}$ (h · ng/mL) | $k_{el}$ (1/h) | $t_{1/2}$ (h) |
|---|---|---|---|---|---|---|---|---|---|---|
| % CV | 40 | 27 | 40 | 42 | 35 | 34 | 24 | NA | NA | NA |
| GM | 212 | 158.00 | 875 | 6850 | 92400 | 138 | 44.1 | NA | NA | NA |

GM: Geometric Mean;
$^a$ratio of $AUC_{0-t}$ (metabolite)/$AUC_{0-t}$ (parent);
$^b$ratio of $AUC_{0-t}$ (each analyte)/$AUC_{0-t}$ (parent + 4 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life;
CL/F, apparent total body clearance;
V/F, apparent total volume of distribution;
NA: Not applicable;
NR: Not reportable.

TABLE 37

Individual and Mean Plasma Concentrations (ngEq/mL) of XL184 using a Radio-Quantitative Method following a Single 175 mg Oral Administration of [$^{14}$C]-XL184 (100 µCi) to Healthy Male Subjects

| Subject | Time (hours) | | | | | | | | | | | |
|---|---|---|---|---|---|---|---|---|---|---|---|---|
| | 0.00 | 0.50 | 1.00 | 2.00 | 3.00 | 4.00 | 5.00 | 8.00 | 14.00 | 24.00 | 72.00 | 168.00 | 336.00 |
| 1444-1023 | 0.0 | 325.6 | 706.6 | 894.9 | 752.7 | 675.6 | 511.9 | 349.8 | 251.3 | 254.6 | 101.4 | 51.2 | 10.3 |
| 1444-1040 | 0.0 | 282.6 | 820.7 | 1132.9 | 876.2 | 912.1 | 806.5 | 501.4 | 486.3 | 573.4 | 227.6 | 54.2 | 12.3 |
| 1444-1042 | 0.0 | 145.3 | 674.9 | 1277.2 | 1177.6 | 1493.7 | 556.5 | 480.1 | 525.6 | 630.4 | 303.7 | 30.3 | 0.0 |
| 1444-1051 | 0.0 | 366.7 | 817.9 | 661.5 | 557.9 | 435.3 | 391.9 | 268.4 | 239.9 | 259.6 | 144.4 | 46.0 | 33.3 |
| 1444-1052 | 0.0 | 150.9 | 439.0 | 880.8 | 1056.2 | 755.1 | 457.2 | 301.1 | 233.3 | 306.3 | 0.0 | 23.9 | 24.1 |
| 1444-1057 | 0.0 | 429.4 | 1077.5 | 1026.3 | 686.3 | 733.3 | 416.1 | 338.6 | 297.9 | 277.5 | 178.8 | 53.6 | 18.3 |
| N | 6 | 6 | 6 | 6 | 6 | 6 | 6 | 6 | 6 | 6 | 6 | 6 | 6 |
| Mean | 0.0 | 283.4 | 756.1 | 978.9 | 851.2 | 834.2 | 523.4 | 373.2 | 339.1 | 383.6 | 159.3 | 43.2 | 16.4 |
| SD | 0.0 | 115.5 | 210.2 | 215.6 | 233.3 | 358.3 | 151.4 | 95.7 | 131.8 | 171.0 | 104.7 | 13.0 | 11.6 |
| SEM | 0.0 | 47.1 | 85.8 | 88.0 | 95.2 | 146.3 | 61.8 | 39.1 | 53.8 | 69.8 | 42.8 | 5.3 | 4.7 |
| Min | 0.0 | 145.3 | 439.0 | 661.5 | 557.9 | 435.3 | 391.9 | 268.4 | 233.3 | 254.6 | 0.0 | 23.9 | 0.0 |
| Median | 0.0 | 304.1 | 762.3 | 960.6 | 814.5 | 744.2 | 484.6 | 344.2 | 274.6 | 291.9 | 161.6 | 48.6 | 15.3 |
| Max | 0.0 | 429.4 | 1077.5 | 1277.2 | 1177.6 | 1493.7 | 806.5 | 501.4 | 525.6 | 630.4 | 303.7 | 54.2 | 33.3 |
| % CV | NA | 41 | 28 | 22 | 27 | 43 | 29 | 26 | 39 | 45 | 66 | 30 | 71 |
| GM | NA | 261.2 | 730.1 | 958.3 | 824.5 | 778.1 | 507.7 | 363.4 | 319.9 | 355.9 | NA | 41.3 | NA |

NA: Not Applicable;
ND: No Data;
GM: Geometric Mean

TABLE 38

Individual and Mean Plasma Concentrations (ngEq/mL) of XL184-Half-Dimer** using a Radio-Quantitative Method following a Single 175 mg Oral Administration of [$^{14}$C]-XL184 (100 µCi) to Healthy Male Subjects

| Subject | Time (hours) | | | | | | | | | | | | |
|---|---|---|---|---|---|---|---|---|---|---|---|---|---|
| | 0 | 0.5 | 1 | 2 | 3 | 4 | 5 | 8 | 14 | 24 | 72 | 168 | 336 |
| 1444-1023 | 0.0 | 139.5 | 166.1 | 173.5 | 97.2 | 162.4 | 111.4 | 129.1 | 109.6 | 89.2 | 58.2 | 0.0 | 0.0 |
| 1444-1040 | 0.0 | 81.0 | 85.9 | 77.2 | 76.6 | 67.1 | 66.7 | 52.1 | 60.2 | 75.2 | 0.0 | 0.0 | 0.0 |
| 1444-1042 | 0.0 | 0.0 | 65.7 | 136.3 | 164.3 | 134.3 | 210.1 | 198.0 | 216.3 | 295.1 | 130.0 | 0.0 | 0.0 |
| 1444-1051 | 0.0 | 132.3 | 213.3 | 198.6 | 186.7 | 138.3 | 158.0 | 98.8 | 154.6 | 124.1 | 69.5 | 31.7 | 0.0 |
| 1444-1052 | 0.0 | 140.9 | 236.4 | 234.6 | 203.0 | 222.9 | 192.0 | 190.2 | 254.7 | 171.2 | 0.0 | 47.7 | 10.7 |
| 1444-1057 | 0.0 | 204.9 | 235.7 | 160.3 | 166.6 | 183.3 | 137.7 | 137.8 | 172.0 | 175.6 | 78.7 | 12.7 | 0.0 |
| N | 6 | 6 | 6 | 6 | 6 | 6 | 6 | 6 | 6 | 6 | 6 | 6 | 6 |
| Mean | 0.0 | 116.4 | 167.2 | 163.4 | 149.1 | 151.4 | 146.0 | 134.3 | 161.2 | 155.1 | 56.1 | 15.4 | 1.8 |

TABLE 38-continued

Individual and Mean Plasma Concentrations (ngEq/mL) of XL184-Half-Dimer**
using a Radio-Quantitative Method following a Single 175 mg Oral Administration of
[$^{14}$C]-XL184 (100 µCi) to Healthy Male Subjects

| Subject | Time (hours) | | | | | | | | | | | | |
|---|---|---|---|---|---|---|---|---|---|---|---|---|---|
| | 0 | 0.5 | 1 | 2 | 3 | 4 | 5 | 8 | 14 | 24 | 72 | 168 | 336 |
| SD | 0.0 | 69.3 | 75.5 | 54.0 | 50.6 | 52.6 | 52.8 | 55.2 | 70.4 | 80.0 | 49.9 | 20.1 | 4.4 |
| SEM | 0.0 | 28.3 | 30.8 | 22.0 | 20.7 | 21.5 | 21.5 | 22.5 | 28.8 | 32.6 | 20.4 | 8.2 | 1.8 |
| Min | 0.0 | 0.0 | 65.7 | 77.2 | 76.6 | 67.1 | 66.7 | 52.1 | 60.2 | 75.2 | 0.0 | 0.0 | 0.0 |
| Median | 0.0 | 135.9 | 189.7 | 166.9 | 165.5 | 150.4 | 147.9 | 133.5 | 163.3 | 147.7 | 63.9 | 6.4 | 0.0 |
| Max | 0.0 | 204.9 | 236.4 | 234.6 | 203.0 | 222.9 | 210.1 | 198.0 | 254.7 | 295.1 | 130.0 | 47.7 | 10.7 |
| % CV | NA | 60 | 45 | 33 | 34 | 35 | 36 | 41 | 44 | 52 | 89 | 131 | 245 |
| GM | NA | NA | 149.4 | 154.6 | 140.6 | 142.2 | 136.7 | 122.9 | 146.0 | 139.5 | NA | NA | NA |

**Co-eluted with Demethyl XL184 glucuronide B;
NA: Not Applicable;
GM: Geometric Mean

TABLE 39

Individual and Mean Plasma Concentrations (ngEq/mL) of XL184-N-Oxide
using a Radio-Quantitative Method following a Single 175 mg Oral Administration
of [$^{14}$C]-XL184 (100 µCi) to Healthy Male Subjects

| Subject | Time (hours) | | | | | | | | | | | | |
|---|---|---|---|---|---|---|---|---|---|---|---|---|---|
| | 0 | 0.5 | 1 | 2 | 3 | 4 | 5 | 8 | 14 | 24 | 72 | 168 | 336 |
| 1444-1023 | 0.0 | 0.0 | 175.4 | 224.8 | 189.5 | 232.5 | 183.2 | 144.4 | 143.6 | 140.5 | 73.8 | 0.0 | 8.9 |
| 1444-1040 | 0.0 | 66.3 | 217.5 | 321.2 | 304.2 | 327.1 | 293.7 | 268.4 | 319.9 | 309.6 | 103.3 | 38.1 | 10.7 |
| 1444-1042 | 0.0 | 0.0 | 131.0 | 331.2 | 344.9 | 161.7 | 284.1 | 110.9 | 69.4 | 111.0 | 100.1 | 0.0 | 0.0 |
| 1444-1051 | 0.0 | 0.0 | 200.6 | 221.9 | 181.3 | 153.4 | 137.5 | 135.2 | 129.0 | 208.3 | 85.1 | 0.0 | 0.0 |
| 1444-1052 | 0.0 | 0.0 | 132.1 | 195.6 | 325.7 | 235.5 | 235.9 | 133.9 | 104.0 | 160.6 | 0.0 | 0.0 | 0.0 |
| 1444-1057 | 0.0 | 87.9 | 215.0 | 340.5 | 252.8 | 237.0 | 216.4 | 167.0 | 178.6 | 229.0 | 60.4 | 34.2 | 0.0 |
| N | 6 | 6 | 6 | 6 | 6 | 6 | 6 | 6 | 6 | 6 | 6 | 6 | 6 |
| Mean | 0.0 | 25.7 | 178.6 | 272.5 | 266.4 | 224.5 | 225.1 | 160.0 | 157.4 | 193.2 | 70.5 | 12.1 | 3.3 |
| SD | 0.0 | 40.4 | 39.4 | 65.1 | 69.9 | 63.0 | 59.7 | 56.1 | 87.7 | 71.6 | 38.1 | 18.7 | 5.1 |
| SEM | 0.0 | 16.5 | 16.1 | 26.6 | 28.5 | 25.7 | 24.4 | 22.9 | 35.8 | 29.2 | 15.5 | 7.6 | 2.1 |
| Min | 0.0 | 0.0 | 131.0 | 195.6 | 181.3 | 153.4 | 137.5 | 110.9 | 69.4 | 111.0 | 0.0 | 0.0 | 0.0 |
| Median | 0.0 | 0.0 | 188.0 | 273.0 | 278.5 | 234.0 | 226.2 | 139.8 | 136.3 | 184.5 | 79.5 | 0.0 | 0.0 |
| Max | 0.0 | 87.9 | 217.5 | 340.5 | 344.9 | 327.1 | 293.7 | 268.4 | 319.9 | 309.6 | 103.3 | 38.1 | 10.7 |
| % CV | NA | 157 | 22 | 24 | 26 | 28 | 27 | 35 | 56 | 37 | 54 | 155 | 156 |
| GM | NA | NA | 174.7 | 265.9 | 258.3 | 217.3 | 218.0 | 153.3 | 140.3 | 182.5 | NA | NA | NA |

NA: Not Applicable;
ND: No Data;
GM: Geometric Mean

TABLE 40

Individual and Mean Plasma Concentrations (ngEq/mL) of XL184-Sulfate***
using a Radio-Quantitative Method following a Single 175 mg Oral Administration of
[$^{14}$C]-XL184 (100 µCi) to Healthy Male Subjects

| Subject | Time (hours) | | | | | | | | | | | | |
|---|---|---|---|---|---|---|---|---|---|---|---|---|---|
| | 0 | 0.5 | 1 | 2 | 3 | 4 | 5 | 8 | 14 | 24 | 72 | 168 | 336 |
| 1444-1023 | 0.0 | 167.5 | 270.2 | 350.0 | 568.8 | 575.3 | 543.8 | 405.8 | 422.7 | 381.1 | 280.7 | 115.5 | 41.6 |
| 1444-1040 | 0.0 | 126.4 | 426.4 | 559.5 | 789.6 | 740.4 | 776.3 | 606.7 | 571.2 | 866.9 | 488.1 | 252.7 | 41.0 |
| 1444-1042 | 0.0 | 0.0 | 247.5 | 504.7 | 589.0 | 452.6 | 718.1 | 207.2 | 264.6 | 630.8 | 418.0 | 101.1 | 15.6 |
| 1444-1051 | 0.0 | 94.8 | 269.3 | 458.4 | 459.9 | 502.0 | 389.9 | 316.1 | 470.7 | 515.7 | 312.6 | 122.3 | 75.3 |
| 1444-1052 | 0.0 | 132.6 | 362.7 | 541.6 | 459.9 | 535.8 | 532.0 | 402.3 | 366.7 | 501.3 | 248.3 | 0.0 | 18.5 |
| 1444-1057 | 0.0 | 282.5 | 460.4 | 600.8 | 588.5 | 673.9 | 496.0 | 435.0 | 545.0 | 529.2 | 311.0 | 192.8 | 19.4 |
| N | 6 | 6 | 6 | 6 | 6 | 6 | 6 | 6 | 6 | 6 | 6 | 6 | 6 |
| Mean | 0.0 | 134.0 | 339.4 | 502.5 | 576.0 | 580.0 | 576.0 | 395.5 | 440.2 | 570.8 | 343.1 | 130.7 | 35.2 |
| SD | 0.0 | 92.4 | 90.4 | 89.0 | 120.8 | 108.5 | 144.4 | 132.7 | 114.6 | 165.4 | 91.1 | 86.0 | 22.8 |
| SEM | 0.0 | 37.7 | 36.9 | 36.4 | 49.3 | 44.3 | 59.0 | 54.2 | 46.8 | 67.5 | 37.2 | 35.1 | 9.3 |
| Min | 0.0 | 0.0 | 247.5 | 350.0 | 459.9 | 452.6 | 389.9 | 207.2 | 264.6 | 381.1 | 248.3 | 0.0 | 15.6 |
| Median | 0.0 | 129.5 | 316.5 | 523.2 | 578.7 | 555.6 | 537.9 | 404.1 | 446.7 | 522.5 | 311.8 | 118.9 | 30.2 |
| Max | 0.0 | 282.5 | 460.4 | 600.8 | 789.6 | 740.4 | 776.3 | 606.7 | 571.2 | 866.9 | 488.1 | 252.7 | 75.3 |

TABLE 40-continued

Individual and Mean Plasma Concentrations(ngEq/mL) of XL184-Sulfate***
using a Radio-Quantitative Method following a Single 175 mg Oral Administration of
[$^{14}$C]-XL184 (100 µCi) to Healthy Male Subjects

| Subject | Time (hours) | | | | | | | | | | | | |
|---|---|---|---|---|---|---|---|---|---|---|---|---|---|
| | 0 | 0.5 | 1 | 2 | 3 | 4 | 5 | 8 | 14 | 24 | 72 | 168 | 336 |
| % CV | NA | 69 | 27 | 18 | 21 | 19 | 25 | 34 | 26 | 29 | 27 | 66 | 65 |
| GM | NA | NA | 329.6 | 495.2 | 566.1 | 571.8 | 561.0 | 375.9 | 426.4 | 552.7 | 333.8 | NA | 29.9 |

***Co-eluted with Half-dimer methyl ester;
NA: Not Applicable;
ND: No Data;
GM: Geometric Mean

TABLE 41

Individual and Mean Plasma Concentrations (ngEq/mL) of Demethyl Half-Dimer Sulfate
using a Radio-Quantitative Method following a Single 175 mg Oral Administration
of [$^{14}$C]-XL184 (100 µCi) to Healthy Male Subjects

| Subject | Time (hours) | | | | | | | | | | | | |
|---|---|---|---|---|---|---|---|---|---|---|---|---|---|
| | 0 | 0.5 | 1 | 2 | 3 | 4 | 5 | 8 | 14 | 24 | 72 | 168 | 336 |
| 1444-1023 | 0.0 | 0.0 | 0.0 | 0.0 | 0.0 | 0.0 | 110.2 | 105.9 | 182.6 | 417.5 | 360.9 | 313.3 | 129.8 |
| 1444-1040 | 0.0 | 0.0 | 0.0 | 0.0 | 0.0 | 0.0 | 0.0 | 0.0 | 60.1 | 87.4 | 172.2 | 165.5 | 71.8 |
| 1444-1042 | 0.0 | 0.0 | 0.0 | 0.0 | 0.0 | 0.0 | 0.0 | 0.0 | 127.1 | 315.2 | 373.2 | 391.1 | 175.0 |
| 1444-1052 | 0.0 | 0.0 | 0.0 | 0.0 | 0.0 | 0.0 | 0.0 | 0.0 | 155.6 | 216.2 | 532.7 | 389.9 | 240.7 |
| N | 4 | 4 | 4 | 4 | 4 | 4 | 4 | 4 | 4 | 4 | 4 | 4 | 4 |
| Mean | 0.0 | 0.0 | 0.0 | 0.0 | 0.0 | 0.0 | 27.6 | 26.5 | 131.4 | 259.1 | 359.8 | 315.0 | 154.3 |
| SD | 0.0 | 0.0 | 0.0 | 0.0 | 0.0 | 0.0 | 55.1 | 53.0 | 52.6 | 140.9 | 147.5 | 106.1 | 71.4 |
| SEM | 0.0 | 0.0 | 0.0 | 0.0 | 0.0 | 0.0 | 27.6 | 26.5 | 26.3 | 70.5 | 73.8 | 53.0 | 35.7 |
| Min | 0.0 | 0.0 | 0.0 | 0.0 | 0.0 | 0.0 | 0.0 | 0.0 | 60.1 | 87.4 | 172.2 | 165.5 | 71.8 |
| Median | 0.0 | 0.0 | 0.0 | 0.0 | 0.0 | 0.0 | 0.0 | 0.0 | 141.4 | 265.7 | 367.1 | 351.6 | 152.4 |
| Max | 0.0 | 0.0 | 0.0 | 0.0 | 0.0 | 0.0 | 110.2 | 105.9 | 182.6 | 417.5 | 532.7 | 391.1 | 240.7 |
| % CV | NA | NA | NA | NA | NA | NA | 200 | 200 | 40 | 54 | 41 | 34 | 46 |
| GM | NA | NA | NA | NA | NA | NA | NA | NA | 121.4 | 223.3 | 333.4 | 298.2 | 140.8 |

GM: Geometric Mean; NA: Not Applicable
Subjects whose PK profile did not contain more than five consecutive data points with a quantifiable concentration value.

| Subject | Time (hours) | | | | | | | | | | | | |
|---|---|---|---|---|---|---|---|---|---|---|---|---|---|
| | 0 | 0.5 | 1 | 2 | 3 | 4 | 5 | 8 | 14 | 24 | 72 | 168 | 336 |
| 1444-1051 | 0.0 | 0.0 | 0.0 | 0.0 | 0.0 | 0.0 | 0.0 | 0.0 | 0.0 | 113.1 | 262.0 | 299.5 | 143.8 |
| 1444-1057 | 0.0 | 0.0 | 0.0 | 0.0 | 0.0 | 0.0 | 0.0 | 0.0 | 0.0 | 142.9 | 249.6 | 149.3 | 157.1 |

TABLE 42

Individual and Mean Plasma Concentrations (ngEq/mL) of P5 using a Radio-Quantitative
Method following a Single 175 mg Oral Administration of [$^{14}$C]-XL184 (100 µCi) to Healthy Male Subjects

| Subject | Time (hours) | | | | | | | | | | | | |
|---|---|---|---|---|---|---|---|---|---|---|---|---|---|
| | 0 | 0.5 | 1 | 2 | 3 | 4 | 5 | 8 | 14 | 24 | 72 | 168 | 336 |
| 1444-1042 | 0.0 | 0.0 | 75.0 | 129.9 | 150.2 | 189.8 | 246.6 | 173.8 | 151.8 | 147.1 | 0.0 | 0.0 | 7.6 |
| 1444-1051 | 0.0 | 69.2 | 126.6 | 144.7 | 114.6 | 116.8 | 106.6 | 102.2 | 0.0 | 0.0 | 61.8 | 31.8 | 0.0 |
| 1444-1052 | 0.0 | 42.1 | 76.1 | 189.6 | 151.9 | 144.0 | 83.4 | 83.0 | 84.9 | 137.1 | 89.9 | 0.0 | 0.0 |
| N | 3 | 3 | 3 | 3 | 3 | 3 | 3 | 3 | 3 | 3 | 3 | 3 | 3 |
| Mean | 0.0 | 37.1 | 92.6 | 154.7 | 138.9 | 150.2 | 145.5 | 119.7 | 78.9 | 94.7 | 50.6 | 10.6 | 2.5 |
| SD | 0.0 | 34.9 | 29.5 | 31.1 | 21.1 | 36.9 | 88.3 | 47.9 | 76.1 | 82.2 | 46.0 | 18.4 | 4.4 |
| SEM | 0.0 | 20.1 | 17.0 | 17.9 | 12.2 | 21.3 | 51.0 | 27.6 | 43.9 | 47.5 | 26.6 | 10.6 | 2.5 |
| Min | 0.0 | 0.0 | 75.0 | 129.9 | 114.6 | 116.8 | 83.4 | 83.0 | 0.0 | 0.0 | 0.0 | 0.0 | 0.0 |

TABLE 42-continued

Individual and Mean Plasma Concentrations (ngEq/mL) of P5 using a Radio-Quantitative
Method following a Single 175 mg Oral Administration of [$^{14}$C]-XL184 (100 µCi) to Healthy Male Subjects

| Median | 0.0 | 42.1 | 76.1 | 144.7 | 150.2 | 144.0 | 106.6 | 102.2 | 84.9 | 137.1 | 61.8 | 0.0 | 0.0 |
|---|---|---|---|---|---|---|---|---|---|---|---|---|---|
| Max | 0.0 | 69.2 | 126.6 | 189.6 | 151.9 | 189.8 | 246.6 | 173.8 | 151.8 | 147.1 | 89.9 | 31.8 | 7.6 |
| % CV | NA | 94 | 32 | 20 | 15 | 25 | 61 | 40 | 96 | 87 | 91 | 173 | 173 |
| GM | NA | NA | 89.7 | 152.7 | 137.8 | 147.2 | 129.9 | 113.8 | NA | NA | NA | NA | NA |

GM: Geometric Mean; NA: Not Applicable
Subjects whose PK profile did not contain more than five consecutive data points with a quantifiable concentration value.

| | Time (hours) | | | | | | | | | | | | |
|---|---|---|---|---|---|---|---|---|---|---|---|---|---|
| Subject | 0 | 0.5 | 1 | 2 | 3 | 4 | 5 | 8 | 14 | 24 | 72 | 168 | 336 |
| 1444-1023 | 0.0 | 0.0 | 0.0 | 0.0 | 146.8 | 0.0 | 0.0 | 0.0 | 0.0 | 112.5 | 0.0 | 37.7 | 11.4 |
| 1444-1040 | 0.0 | 0.0 | 0.0 | 126.4 | 145.3 | 160.8 | 0.0 | 0.0 | 81.0 | 103.9 | 0.0 | 0.0 | 0.0 |
| 1444-1057 | 0.0 | 0.0 | 0.0 | 123.7 | 184.7 | 0.0 | 131.9 | 86.6 | 128.2 | 98.7 | 0.0 | 21.5 | 0.0 |

TABLE 43

Individual and Mean Plasma Concentrations (ngEq/mL) of P7 using a Radio-Quantitative
Method following a Single 175 mg Oral Administration of [$^{14}$C]-XL184 (100 µCi)
to Healthy Male Subjects

| | Time (hours) | | | | | | | | | | | | |
|---|---|---|---|---|---|---|---|---|---|---|---|---|---|
| Subject | 0 | 0.5 | 1 | 2 | 3 | 4 | 5 | 8 | 14 | 24 | 72 | 168 | 336 |
| 1444-1051 | 0.0 | 55.4 | 76.8 | 95.3 | 72.7 | 85.0 | 57.1 | 38.4 | 0.0 | 0.0 | 0.0 | 0.0 | 0.0 |
| N | 1 | 1 | 1 | 1 | 1 | 1 | 1 | 1 | 1 | 1 | 1 | 1 | 1 |
| Mean | 0.0 | 55.4 | 76.8 | 95.3 | 72.7 | 85.0 | 57.1 | 38.4 | 0.0 | 0.0 | 0.0 | 0.0 | 0.0 |
| SD | NA | NA | NA | NA | NA | NA | NA | NA | NA | NA | NA | NA | NA |
| SEM | NA | NA | NA | NA | NA | NA | NA | NA | NA | NA | NA | NA | NA |
| Min | 0.0 | 55.4 | 76.8 | 95.3 | 72.7 | 85.0 | 57.1 | 38.4 | 0.0 | 0.0 | 0.0 | 0.0 | 0.0 |
| Median | 0.0 | 55.4 | 76.8 | 95.3 | 72.7 | 85.0 | 57.1 | 38.4 | 0.0 | 0.0 | 0.0 | 0.0 | 0.0 |
| Max | 0.0 | 55.4 | 76.8 | 95.3 | 72.7 | 85.0 | 57.1 | 38.4 | 0.0 | 0.0 | 0.0 | 0.0 | 0.0 |
| % CV | NA | NA | NA | NA | NA | NA | NA | NA | NA | NA | NA | NA | NA |
| GM | NA | 55.4 | 76.8 | 95.3 | 72.7 | 85.0 | 57.1 | 38.4 | NA | NA | NA | NA | NA |

GM: Geometric Mean; NA: Not Applicable
Subjects whose PK profile did not contain more than five consecutive data points with a quantifiable concentration value.

| | Time (hours) | | | | | | | | | | | | |
|---|---|---|---|---|---|---|---|---|---|---|---|---|---|
| Subject | 0 | 0.5 | 1 | 2 | 3 | 4 | 5 | 8 | 14 | 24 | 72 | 168 | 336 |
| 1444-1023 | 0.0 | 0.0 | 0.0 | 0.0 | 0.0 | 0.0 | 0.0 | 0.0 | 0.0 | 0.0 | 0.0 | 0.0 | 0.0 |
| 1444-1040 | 0.0 | 0.0 | 0.0 | 0.0 | 0.0 | 0.0 | 0.0 | 0.0 | 0.0 | 0.0 | 0.0 | 0.0 | 0.0 |
| 1444-1042 | 0.0 | 0.0 | 0.0 | 0.0 | 0.0 | 0.0 | 0.0 | 0.0 | 0.0 | 0.0 | 0.0 | 0.0 | 0.0 |
| 1444-1052 | 0.0 | 0.0 | 0.0 | 110.5 | 156.0 | 0.0 | 87.1 | 0.0 | 0.0 | 0.0 | 0.0 | 0.0 | 0.0 |
| 1444-1057 | 0.0 | 0.0 | 106.9 | 0.0 | 0.0 | 106.2 | 54.2 | 56.4 | 0.0 | 0.0 | 0.0 | 0.0 | 0.0 |

TABLE 44

Individual Plasma Concentrations (ngEq/mL) of P2 using a Radio-quantitative Method
following a Single 175 mg Oral Administration of [$^{14}$C]-XL184 (100 µCi) to Healthy Male Subjects
Subjects whose PK profile did not contain more than five consecutive data points with a quantifiable concentration value.

| | Time (hours) | | | | | | | | | | | | |
|---|---|---|---|---|---|---|---|---|---|---|---|---|---|
| Subject | 0 | 0.5 | 1 | 2 | 3 | 4 | 5 | 8 | 14 | 24 | 72 | 168 | 336 |
| 1444-1023 | 0.0 | 0.0 | 0.0 | 0.0 | 0.0 | 0.0 | 0.0 | 0.0 | 0.0 | 41.5 | 0.0 | 0.0 | 0.0 |
| 1444-1040 | 0.0 | 0.0 | 0.0 | 0.0 | 0.0 | 0.0 | 0.0 | 0.0 | 0.0 | 0.0 | 0.0 | 0.0 | 0.0 |
| 1444-1042 | 0.0 | 0.0 | 0.0 | 0.0 | 0.0 | 0.0 | 0.0 | 0.0 | 0.0 | 0.0 | 0.0 | 0.0 | 0.0 |

TABLE 44-continued

Individual Plasma Concentrations (ngEq/mL) of P2 using a Radio-quantitative Method
following a Single 175 mg Oral Administration of [$^{14}$C]-XL184 (100 µCi) to Healthy Male Subjects
Subjects whose PK profile did not contain more than five consecutive data points with a quantifiable concentration value.

| Subject | Time (hours) | | | | | | | | | | | | |
|---|---|---|---|---|---|---|---|---|---|---|---|---|---|
| | 0 | 0.5 | 1 | 2 | 3 | 4 | 5 | 8 | 14 | 24 | 72 | 168 | 336 |
| 1444-1051 | 0.0 | 0.0 | 0.0 | 0.0 | 0.0 | 49.5 | 0.0 | 0.0 | 0.0 | 0.0 | 0.0 | 0.0 | 0.0 |
| 1444-1052 | 0.0 | 0.0 | 58.7 | 0.0 | 74.1 | 0.0 | 0.0 | 72.7 | 0.0 | 0.0 | 0.0 | 0.0 | 0.0 |
| 1444-1057 | 0.0 | 0.0 | 0.0 | 0.0 | 0.0 | 0.0 | 0.0 | 0.0 | 0.0 | 46.3 | 0.0 | 0.0 | 0.0 |

TABLE 45

Individual and Descriptive Statistics of Plasma
Pharmacokinetic Parameters of XL184 using a Radio-quantitative Method following a
Single 175 mg Oral Administration of [$^{14}$C]-XL184 (100 µCi) to Healthy Male Subjects

| Subject | $C_{max}$ (ngEq/mL) | $t_{max}$ (h) | $AUC_{0-t}$ (h · ngEq/mL) | $AUC_{0-24}$ (h · ngEq/mL) | $AUC_{0-72}$ (h · ngEq/mL) | Ratio[b] (%) | $AUC_{0-inf}$ (h · ngEq/mL) | $k_{el}$ (1/h) | $t_{1/2}$ (h) |
|---|---|---|---|---|---|---|---|---|---|
| 1444-1023 | 895 | 1.98 | 29900 | 8890 | 17400 | 15.0 | 31100 | 0.00876 | 79.1 |
| 1444-1040 | 1130 | 2.00 | 52600 | 14300 | 33500 | 22.5 | 53700 | 0.0119 | 58.0 |
| 1444-1042 | 1490 | 4.00 | 53600 | 15200 | 37600 | 20.8 | 55000 | 0.0215 | 32.2 |
| 1444-1051 | 818 | 1.00 | 33200 | 7660 | 17400 | 25.1 | 38000 | 0.00685 | 101 |
| 1444-1052 | 1060 | 3.00 | 21300 | 8770 | 16100 | 10.2 | 24000 | 0.00909 | 76.2 |
| 1444-1057 | 1080 | 1.00 | 37700 | 9600 | 20600 | 26.4 | 39800 | 0.00906 | 76.5 |
| N | 6 | 6 | 6 | 6 | 6 | 6 | 6 | 6 | 6 |
| Mean | 1080 | 2.16 | 38100 | 10700 | 23800 | 20.0 | 40300 | 0.0112 | 70.5 |
| SD | 234 | 1.17 | 12800 | 3170 | 9340 | 6.24 | 12300 | 0.0053 | 23.2 |
| SEM | 95.5 | 0.48 | 5240 | 1300 | 3810 | 2.55 | 5010 | 0.00216 | 9.48 |
| Min | 818 | 1.00 | 21300 | 7660 | 16100 | 10.2 | 24000 | 0.00685 | 32.2 |
| Median | 1070 | 1.99 | 35500 | 9250 | 19000 | 21.7 | 38900 | 0.00908 | 76.4 |
| Max | 1490 | 4.00 | 53600 | 15200 | 37600 | 26.4 | 55000 | 0.0215 | 101 |
| % CV | 22 | 54 | 34 | 30 | 39 | 31 | 30 | 47 | 33 |
| GM | 1060 | 1.90 | 36200 | 10400 | 22400 | 19.0 | 38700 | 0.0104 | 66.6 |

GM: Geometric Mean;
[b]ratio of $AUC_{0-t}$ (each analyte)/$AUC_{0-t}$ (parent + 6 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$ apparent terminal elimination rate constant;
$t_{1/2}$, apparent terminal elimination half-life;
CL/F, apparent total body clearance;
V/F, apparent total volume of distribution.

TABLE 46

Individual and Descriptive Statistics of Plasma
Pharmacokinetic Parameters of XL184-Half-dimer** using a Radio-quantitative
Method following a Single 175 mg Oral Administration of [$^{14}$C]-XL184 (100 µCi) to
Healthy Male Subjects

| Subject | $C_{max}$ (ngEq/mL) | $t_{max}$ (h) | $AUC_{0-t}$ (h · ngEq/mL) | $AUC_{0-24}$ (h · ngEq/mL) | $AUC_{0-72}$ (h · ngEq/mL) | Ratio[a] (%) | Ratio[b] (%) | $AUC_{0-inf}$ (h · ngEq/mL) | $k_{el}$ (1/h) | $t_{1/2}$ (h) |
|---|---|---|---|---|---|---|---|---|---|---|
| 1444-1023 | 174 | 1.98 | 6290 | 2750 | 6290 | 21.0 | 3.15 | NR | NR | NR |
| 1444-1040 | 85.9 | 1.00 | 1550 | 1550 | 3360 | 2.95 | 0.664 | NR | NR | NR |
| 1444-1042 | 295 | 24.03 | 15200 | 5000 | 15200 | 28.4 | 5.91 | NE | NE | NE |
| 1444-1051 | 213 | 1.00 | 12900 | 3370 | 8020 | 38.9 | 9.77 | NR | NR | NR |
| 1444-1052 | 255 | 14.00 | 16400 | 5050 | 9160 | 77.0 | 7.89 | 17600 | 0.00889 | 77.9 |
| 1444-1057 | 236 | 1.00 | 14400 | 3940 | 10000 | 38.2 | 10.1 | 15100 | 0.0184 | 37.8 |
| N | 6 | 6 | 6 | 6 | 6 | 6 | 6 | 2 | 2 | 2 |
| Mean | 210 | 7.17 | 11100 | 3610 | 8680 | 34.4 | 6.25 | 16400 | 0.0136 | 57.9 |
| SD | 73.0 | 9.72 | 5890 | 1350 | 3980 | 24.7 | 3.76 | 1770 | 0.00672 | 28.4 |
| SEM | 29.8 | 3.97 | 2400 | 552 | 1620 | 10.1 | 1.54 | 1250 | 0.00476 | 20.1 |
| Min | 85.9 | 1.00 | 1550 | 1550 | 3360 | 2.95 | 0.664 | 15100 | 0.00889 | 37.8 |
| Median | 225 | 1.49 | 13700 | 3650 | 8590 | 33.3 | 6.90 | 16400 | 0.0136 | 57.9 |

TABLE 46-continued

Individual and Descriptive Statistics of Plasma
Pharmacokinetic Parameters of XL184-Half-dimer** using a Radio-quantitative
Method following a Single 175 mg Oral Administration of [$^{14}$C]-XL184 (100 µCi) to
Healthy Male Subjects

| Subject | $C_{max}$ (ngEq/mL) | $t_{max}$ (h) | $AUC_{0-t}$ (h · ngEq/mL) | $AUC_{0-24}$ (h · ngEq/mL) | $AUC_{0-72}$ (h · ngEq/mL) | Ratio$^a$ (%) | Ratio$^b$ (%) | $AUC_{0-inf}$ (h · ngEq/mL) | $k_{el}$ (1/h) | $t_{1/2}$ (h) |
|---|---|---|---|---|---|---|---|---|---|---|
| Max | 295 | 24.03 | 16400 | 5050 | 15200 | 77.0 | 10.1 | 17600 | 0.0184 | 77.9 |
| % CV | 35 | 136 | 53 | 37 | 46 | 72 | 60 | 11 | 49 | 49 |
| GM | 196 | 2.96 | 8760 | 3360 | 7870 | 24.2 | 4.61 | 16300 | 0.0128 | 54.3 |

**Co-eluted with Demethyl XL184 glucuronide B;
GM: Geometric Mean;
$^a$ratio of $AUC_{0-t}$ (metabolite)/$AUC_{0-t}$ (parent);
$^b$ratio of $AUC_{0-t}$ (each analyte)/$AUC_{0-t}$ (parent + 6 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life;
CL/F, apparent total body clearance;
V/F, apparent total volume of distribution;
NE: Not Estimable;
NR: Not reportable since $AUC_{0-t}$/$AUC_{0-inf}$ ratio < 0.80

TABLE 47

Individual and Descriptive Statistics of Plasma
Pharmacokinetic Parameters of XL184-N-oxide using a Radio-quantitative Method
following a Single 175 mg Oral Administration of [$^{14}$C]-XL184 (100 µCi) to Healthy
Male Subjects

| Subject | $C_{max}$ (ngEq/mL) | $t_{max}$ (h) | $AUC_{0-t}$ (h · ngEq/mL) | $AUC_{0-24}$ (h · ngEq/mL) | $AUC_{0-72}$ (h · ngEq/mL) | Ratio$^a$ (%) | Ratio$^b$ (%) | $AUC_{0-inf}$ (h · ngEq/mL) | $k_{el}$ (1/h) | $t_{1/2}$ (h) |
|---|---|---|---|---|---|---|---|---|---|---|
| 1444-1023 | 233 | 4.00 | 13100 | 3650 | 8790 | 43.8 | 6.55 | 14100 | 0.0086 | 80.6 |
| 1444-1040 | 327 | 4.00 | 27900 | 7050 | 17000 | 53.0 | 12.0 | 29100 | 0.00847 | 81.8 |
| 1444-1042 | 345 | 3.00 | 8180 | 3110 | 8180 | 15.3 | 3.18 | NR | NR | NR |
| 1444-1051 | 222 | 2.00 | 10700 | 3660 | 10700 | 32.2 | 8.10 | NR | NR | NR |
| 1444-1052 | 326 | 3.00 | 3580 | 3560 | 7430 | 16.8 | 1.72 | NR | NR | NR |
| 1444-1057 | 341 | 2.00 | 16300 | 4790 | 11700 | 43.2 | 11.4 | 19100 | 0.0122 | 56.9 |
| N | 6 | 6 | 6 | 6 | 6 | 6 | 6 | 3 | 3 | 3 |
| Mean | 299 | 3.00 | 13300 | 4300 | 10600 | 34.1 | 7.16 | 20800 | 0.00976 | 73.1 |
| SD | 56.0 | 0.89 | 8360 | 1460 | 3490 | 15.4 | 4.20 | 7640 | 0.00212 | 14.0 |
| SEM | 22.9 | 0.37 | 3410 | 594 | 1430 | 6.30 | 1.71 | 4410 | 0.00122 | 8.11 |
| Min | 222 | 2.00 | 3580 | 3110 | 7430 | 15.3 | 1.72 | 14100 | 0.00847 | 56.9 |
| Median | 327 | 3.00 | 11900 | 3650 | 9750 | 37.7 | 7.33 | 19100 | 0.0086 | 80.6 |
| Max | 345 | 4.00 | 27900 | 7050 | 17000 | 53.0 | 12.0 | 29100 | 0.0122 | 81.8 |
| % CV | 19 | 30 | 63 | 34 | 33 | 45 | 59 | 37 | 22 | 19 |
| GM | 294 | 2.88 | 11100 | 4140 | 10200 | 30.7 | 5.84 | 19900 | 0.00961 | 72.1 |

GM: Geometric Mean;
$^a$ratio of $AUC_{0-t}$ (metabolite)/$AUC_{0-t}$ (parent);
$^b$ratio of $AUC_{0-t}$ (each analyte)/$AUC_{0-t}$ (parent + 6 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life;
CL/F, apparent total body clearance;
V/F, apparent total volume of distribution;
NR: Not reportable since $AUC_{0-t}$/$AUC_{0-inf}$ ratio < 0.80

TABLE 48

Individual and Descriptive Statistics of Plasma Pharmacokinetic Parameters of XL184-Sulfate*** using a Radio-quantitative Method following a Single 175 mg Oral Administration of [$^{14}$C]-XL184 (100 μCi) to Healthy Male Subjects

| Subject | $C_{max}$ (ngEq/mL) | $t_{max}$ (h) | $AUC_{0-t}$ (h·ngEq/mL) | $AUC_{0-24}$ (h·ngEq/mL) | $AUC_{0-72}$ (h·ngEq/mL) | Ratio$^a$ (%) | Ratio$^b$ (%) | $AUC_{0-inf}$ (h·ngEq/mL) | $k_{el}$ (1/h) | $t_{1/2}$ (h) |
|---|---|---|---|---|---|---|---|---|---|---|
| 1444-1023 | 575 | 4.00 | 58100 | 9980 | 25900 | 194 | 29.1 | 63800 | 0.00722 | 96.0 |
| 1444-1040 | 867 | 24.03 | 108000 | 15700 | 48200 | 205 | 46.3 | 113000 | 0.00958 | 72.3 |
| 1444-1042 | 718 | 5.00 | 69300 | 9370 | 34500 | 129 | 26.9 | 70500 | 0.0121 | 57.2 |
| 1444-1051 | 516 | 24.08 | 67600 | 10200 | 30100 | 204 | 51.2 | 80000 | 0.00606 | 114 |
| 1444-1052 | 542 | 1.98 | 41700 | 10200 | 28200 | 196 | 20.1 | 43400 | 0.0103 | 67.1 |
| 1444-1057 | 674 | 4.00 | 74500 | 12300 | 32500 | 198 | 52.1 | 76400 | 0.0101 | 68.4 |
| N | 6 | 6 | 6 | 6 | 6 | 6 | 6 | 6 | 6 | 6 |
| Mean | 649 | 10.52 | 69900 | 11300 | 33200 | 188 | 37.6 | 74500 | 0.00923 | 79.2 |
| SD | 132 | 10.53 | 22000 | 2360 | 7940 | 29.1 | 13.9 | 22900 | 0.00221 | 21.4 |
| SEM | 54.0 | 4.30 | 8970 | 964 | 3240 | 11.9 | 5.67 | 9330 | 0.000901 | 8.73 |
| Min | 516 | 1.98 | 41700 | 9370 | 25900 | 129 | 20.1 | 43400 | 0.00606 | 57.2 |
| Median | 625 | 4.50 | 68500 | 10200 | 31300 | 197 | 37.7 | 73500 | 0.00984 | 70.4 |
| Max | 867 | 24.08 | 108000 | 15700 | 48200 | 205 | 52.1 | 113000 | 0.0121 | 114 |
| % CV | 20 | 100 | 31 | 21 | 24 | 15 | 37 | 31 | 24 | 27 |
| GM | 638 | 6.71 | 67100 | 11100 | 32500 | 185 | 35.3 | 71600 | 0.00899 | 77.0 |

***Co-eluted with Half-dimer methyl ester;

GM: Geometric Mean;

$^a$ratio of $AUC_{0-t}$ (metabolite)/$AUC_{0-t}$ (parent);

$^b$ratio of $AUC_{0-t}$ (each analyte)/$AUC_{0-t}$ (parent + 6 measured metabolites);

$C_{max}$, maximum observed concentration;

$T_{max}$, time of the maximum concentration;

$AUC_{0-t}$, area under the concentration-time curve from time zero to the time of the last measurable concentration;

$AUC_{0-24}$, area under the concentration-time curve from time zero to 24 hours post XL184 dose;

$AUC_{0-72}$, area under the concentration-time curve from time zero to 72 hours post XL184 dose;

$AUC_{0-inf}$, area under the concentration-time curve from time zero to infinity;

$k_{el}$, apparent terminal elimination rate constant;

$t_{1/2}$, apparent terminal elimination half-life;

CL/F, apparent total body clearance;

V/F, apparent total volume of distribution;

TABLE 49

Individual and Descriptive Statistics of Plasma Pharmacokinetic Parameters of Demethyl Half-dimer Sulfate using a Radio-quantitative Method following a Single 175 mg Oral Administration of [$^{14}$C]-XL184 (100 μCi) to Healthy Male Subjects

| Subject | $C_{max}$ (ngEq/mL) | $t_{max}$ (h) | $AUC_{0-t}$ (h·ngEq/mL) | $AUC_{0-24}$ (h·ngEq/mL) | $AUC_{0-72}$ (h·ngEq/mL) | Ratio$^a$ (%) | Ratio$^b$ (%) | $AUC_{0-inf}$ (h·ngEq/mL) | $k_{el}$ (1/h) | $t_{1/2}$ (h) |
|---|---|---|---|---|---|---|---|---|---|---|
| 1444-1023 | 418 | 24.00 | 92500 | 4250 | 22900 | 309 | 46.3 | NR | NR | NR |
| 1444-1040 | 172 | 72.00 | 43300 | 917 | 7150 | 82.3 | 18.6 | NR | NR | NR |
| 1444-1042 | 391 | 168.00 | 103000 | 2590 | 19100 | 192 | 40.0 | NE | NE | NE |
| 1444-1052 | 533 | 71.98 | 117000 | 2320 | 20300 | 549 | 56.3 | NR | NR | NR |
| N | 4 | 4 | 4 | 4 | 4 | 4 | 4 | 0 | 0 | 0 |
| Mean | 379 | 84.00 | 89000 | 2520 | 17400 | 283 | 40.3 | NA | NA | NA |
| SD | 151 | 60.40 | 32000 | 1370 | 7000 | 200 | 15.9 | NA | NA | NA |
| SEM | 75.4 | 30.20 | 16000 | 683 | 3500 | 100 | 7.97 | NA | NA | NA |
| Min | 172 | 24.00 | 43300 | 917 | 7150 | 82.3 | 18.6 | NA | NA | NA |
| Median | 405 | 71.99 | 97800 | 2460 | 19700 | 251 | 43.2 | NA | NA | NA |
| Max | 533 | 168.00 | 117000 | 4250 | 22900 | 549 | 56.3 | NA | NA | NA |

TABLE 49-continued

Individual and Descriptive Statistics of Plasma Pharmacokinetic Parameters of Demethyl Half-dimer Sulfate using a Radio-quantitative Method following a Single 175 mg Oral Administration of [$^{14}$C]-XL184 (100 µCi) to Healthy Male Subjects

| Subject | $C_{max}$ (ngEq/mL) | $t_{max}$ (h) | $AUC_{0-t}$ (h·ngEq/mL) | $AUC_{0-24}$ (h·ngEq/mL) | $AUC_{0-72}$ (h·ngEq/mL) | Ratio$^a$ (%) | Ratio$^b$ (%) | $AUC_{0-inf}$ (h·ngEq/mL) | $k_{el}$ (1/h) | $t_{1/2}$ (h) |
|---|---|---|---|---|---|---|---|---|---|---|
| % CV | 40 | 72 | 36 | 54 | 40 | 71 | 40 | NA | NA | NA |
| GM | 350 | 67.61 | 83400 | 2200 | 15900 | 228 | 37.3 | NA | NA | NA |

GM: Geometric Mean;
NR: Not reportable since $AUC_{0-t}/AUC_{0-inf}$ ratio < 0.80;
NE: Not Estimable;
NA: Not Applicable;
$^a$ratio of $AUC_{0-t}$ (metabolite)/$AUC_{0-t}$ (parent);
$^b$ratio of $AUC_{0-t}$ (each analyte)/$AUC_{0-t}$ (parent + 6 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life;
CL/F, apparent total body clearance;
V/F, apparent total volume of distribution

TABLE 50

Individual and Descriptive Statistics of Plasma Pharmacokinetic Parameters of P5 using a Radio-quantitative Method following a Single 175 mg Oral Administration of [$^{14}$C]-XL184 (100 µCi) to Healthy Male Subjects

| Subject | $C_{max}$ (ngEq/mL) | $t_{max}$ (h) | $AUC_{0-t}$ (h·ngEq/mL) | $AUC_{0-24}$ (h·ngEq/mL) | $AUC_{0-72}$ (h·ngEq/mL) | Ratio$^a$ (%) | Ratio$^b$ (%) | $AUC_{0-inf}$ (h·ngEq/mL) | $k_{el}$ (1/h) | $t_{1/2}$ (h) |
|---|---|---|---|---|---|---|---|---|---|---|
| 1444-1042 | 247 | 5.00 | 7920 | 3750 | 7280 | 14.8 | 3.08 | 8720 | 0.00945 | 73.4 |
| 1444-1051 | 145 | 2.00 | 7150 | 1180 | 2660 | 21.5 | 5.41 | NR | NR | NR |
| 1444-1052 | 190 | 1.98 | 7910 | 2470 | 7920 | 37.1 | 3.80 | NR | NR | NR |
| N | 3 | 3 | 3 | 3 | 3 | 3 | 3 | 1 | 1 | 1 |
| Mean | 194 | 2.99 | 7660 | 2470 | 5950 | 24.5 | 4.10 | 8720 | 0.00945 | 73.4 |
| SD | 51.1 | 1.74 | 442 | 1290 | 2870 | 11.4 | 1.19 | NA | NA | NA |
| SEM | 29.5 | 1.00 | 255 | 743 | 1660 | 6.61 | 0.689 | NA | NA | NA |
| Min | 145 | 1.98 | 7150 | 1180 | 2660 | 14.8 | 3.08 | 8720 | 0.00945 | 73.4 |
| Median | 190 | 2.00 | 7910 | 2470 | 7280 | 21.5 | 3.80 | 8720 | 0.00945 | 73.4 |
| Max | 247 | 5.00 | 7920 | 3750 | 7920 | 37.1 | 5.41 | 8720 | 0.00945 | 73.4 |
| % CV | 26 | 58 | 6 | 52 | 48 | 47 | 29 | NA | NA | NA |
| GM | 189 | 2.71 | 7650 | 2220 | 5350 | 22.8 | 3.99 | 8720 | 0.00945 | 73.4 |

GM: Geometric Mean;
NR: Not reportable since $AUC_{0-t}/AUC_{0-inf}$ ratio < 0.80;
NA: Not Applicable;
$^a$ratio of $AUC_{0-t}$ (metabolite)/$AUC_{0-t}$ (parent);
$^b$ratio of $AUC_{0-t}$ (each analyte)/$AUC_{0-t}$ (parent + 6 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{max}$, apparent terminal elimination half-life;
CL/F, apparent total body clearance;
V/F, apparent total volume of distribution

TABLE 51

Individual and Descriptive Statistics of Plasma Pharmacokinetic Parameters of P7 using a Radio-quantitative Method following a Single 175 mg Oral Administration of [$^{14}$C]-XL184 (100 μCi) to Healthy Male Subjects

| Subject | $C_{max}$ (ngEq/mL) | $t_{max}$ (h) | $AUC_{0-t}$ (h · ngEq/mL) | $AUC_{0-24}$ (h · ngEq/mL) | $AUC_{0-72}$ (h · ngEq/mL) | Ratio$^a$ (%) | Ratio$^b$ (%) | $AUC_{0-inf}$ (h · ngEq/mL) | $k_{el}$ (1/h) | $t_{1/2}$ (h) |
|---|---|---|---|---|---|---|---|---|---|---|
| 1444-1051 | 95.3 | 2.00 | 510 | 625 | 625 | 1.54 | 0.386 | NR | NR | NR |
| N | 1 | 1 | 1 | 1 | 1 | 1 | 1 | 0 | 0 | 0 |
| Mean | 95.3 | 2.00 | 510 | 625 | 625 | 1.54 | 0.386 | NA | NA | NA |
| SD | NA | NA | NA | NA | NA | NA | NA | NA | NA | NA |
| SEM | NA | NA | NA | NA | NA | NA | NA | NA | NA | NA |
| Min | 95.3 | 2.00 | 510 | 625 | 625 | 1.54 | 0.386 | NA | NA | NA |
| Median | 95.3 | 2.00 | 510 | 625 | 625 | 1.54 | 0.386 | NA | NA | NA |
| Max | 95.3 | 2.00 | 510 | 625 | 625 | 1.54 | 0.386 | NA | NA | NA |
| % CV | NA | NA | NA | NA | NA | NA | NA | NA | NA | NA |
| GM | 95.3 | 2.00 | 510 | 625 | 625 | 1.54 | 0.386 | NA | NA | NA |

GM: Geometric Mean;
NR: Not reportable since $AUC_{0-t}/AUC_{0-inf}$ ratio < 0.80;
NA: Not Applicable;
$^a$ratio of $AUC_{0-t}$ (metabolite)/$AUC_{0-t}$ (parent);
$^b$ratio of $AUC_{0-t}$ (each analyte)/$AUC_{0-t}$ (parent + 6 measured metabolites);
$C_{max}$, maximum observed concentration;
$T_{max}$, time of the maximum concentration;
$AUC_{0-t}$, area under the concentration-time curve from time zero to the time of the last measurable concentration;
$AUC_{0-24}$, area under the concentration-time curve from time zero to 24 hours post XL184 dose;
$AUC_{0-72}$, area under the concentration-time curve from time zero to 72 hours post XL184 dose;
$AUC_{0-inf}$, area under the concentration-time curve from time zero to infinity;
$k_{el}$, apparent terminal elimination rate constant;
$t_{1/2}$, apparent terminal elimination half-life;
CL/F, apparent total body clearance;
V/F, apparent total volume of distribution Procedure for Preparation of Vehicle for [$^{14}$C]-XL184 for Oral Solution: PEG-400/TPGS/Ethanol 85/10/5 w/w/w Example for 600 g—Scale amounts proportionally for other volumes desired.
1. Heat about 600 g of PEG 400 in an oven set at 50° C.
2. Heat about 100 g of TPGS in an oven set at 50° C. Heat till TPGS has completely liquefied.
3. Weigh a 1000 mL glass bottle with cap and record the weight.
4. Tare the balance.
5. Weigh 510 g of warm PEG 400 from step 1 into the glass bottle from step 4.
6. Tare the balance.
7. Weigh 60 g of TPGS from step 2 into the bottle from step 6.
8. Mix the contents of the bottle from step 7 by swirling gently.
9. Place the bottle from step 8 in an oven set at 50° C. for about 30 minutes, swirl the contents intermittently to ensure that the solution is homogenous.
10. Remove the bottle from step 9 from the oven and allow it to cool to RT.
11. Place the bottle on the balance and tare the balance.
12. Weigh 30 g of ethanol into the bottle from step 11, seal the bottle with the cap, and mix the contents gently till the solution is homogenous.
13. Label the bottle as follows:
 "Vehicle for [$^{14}$C(U)]XL184 for Oral Solution"
 "Store tightly capped at 25° C. to 37° C."
 Preparation date and time
 Use date and time (use within 24 hours of preparation).
Note: The vehicle must be stored between 25° C. and 37° C. The vehicle, when exposed to temperatures below 25° C. for extended duration (4-6 hours), might become cloudy due to precipitation of TPGS. If this happens then the vehicle may be heated to 37° C. to dissolve any precipitate. Handling to the vehicle at ambient temperature during preparation of the formulation is permissible.

Procedure for Preparation of Oral Solution of [$^{14}$C]-XL184

175 mg/subject (salt basis); 100 μCi/subject; concentration of drug in vehicle is about 8 mg/mL (salt basis)
1. Prepare 500 g of vehicle according to instructions; include cinnamon flavoring (0.1% v/v).
2. Dispense about 263 mL of vehicle into tared dose prep container (suggest 500 mL quantity).
3. Add 2100 mg of unlabeled XL184.
4. Add approx. 10 mg of labeled XL184.
5. Dissolve drug in vehicle, according to instructions.
6. Weigh total amount.
7. Withdraw two or three aliquots of about 1 g each and determine radioactivity per unit weight, by LSC and drug potency.
8. Dispense about 22 mL aliquots for each subject and obtain accurate weight for each aliquot.
9. Administer each aliquot to subject.

Dose dispensed to each subject will be accurately determined by multiplying weight of each aliquot in Step 8 with activity determined in Step 7.

REFERENCES

Kurzrock R, Sherman S I, Ball D W, Forastiere A A, Cohen R B, Mehra R, Pfister D G, Cohen E E, Janisch L, Nauling F, Hong D S, Ng C S, Ye L, Gagel R F, Frye J, Müller T, Ratain M J, Salgia R. Activity of XL184 (Cabozantinib), an oral tyrosine kinase inhibitor, in patients with medullary thyroid cancer. J Clin Oncol. 2011; 29(19):2660-6.

Yakes F M, Chen J, Tan J, Yamaguchi K, Shi Y, Yu P, et al. Cabozantinib (XL184), a novel MET and VEGFR2 inhibitor, simultaneously suppresses metastasis, angiogenesis, and tumor growth. Mol Cancer Ther. 2011; 10(12): 2298-308.

The foregoing disclosure has been described in some detail by way of illustration and example for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:

1. A liquid pharmaceutical composition for oral administration comprising Cabozantinib (S)-malate and a pharmaceutically acceptable carrier, wherein the carrier comprises from 50% to 95% polyethyleneglycols (w/w), from 1% to 30% d-α-tocopheryl polyethylene glycol succinate (TPGS, w/w), and from 0.5% to 20% ethanol (w/w), wherein the liquid formulation when administered to a plurality of patients as a single dose provides an interpatient or intrapatient exposure variability of less than 30%, wherein exposure is represented by a pharmacokinetic parameter selected from the group consisting of area under the plasma concentration-time curve ($AUC_{0-t}$), maximum observed concentration ($C_{max}$), time of maximum concentration ($t_{max}$), apparent terminal elimination rate constant ($k_{el}$), and apparent terminal elimination half-life calculated as $\ln(2)/k_{el}(t_{1/2})$.

2. The liquid pharmaceutical composition of claim 1, wherein the amount of Cabozantinib (S)-malate present in the liquid formulation, ranges from 1 mg to 200 mg.

3. The liquid pharmaceutical composition of claim 1, wherein the amount of Cabozantinib (S)-malate present in the liquid formulation, ranges from 10 mg to 100 mg.

4. The liquid pharmaceutical composition of claim 1, wherein the carrier comprises from 80% to 90% polyethyleneglycols (w/w), from 5% to 15% TPGS (w/w), and from 1% to 10% ethanol (w/w).

5. The liquid pharmaceutical composition of claim 4, including a flavoring agent.

6. A liquid pharmaceutical composition, comprising Cabozantinib (S)-malate and a pharmaceutically acceptable carrier, wherein the carrier comprises ethanol, d-α-tocopheryl polyethylene glycol succinate (TPGS), polyethyleneglycol, and flavorings; and wherein the liquid formulation when administered to a plurality of patients as a single dose provides an interpatient or intrapatient exposure variability of less than 30%, wherein exposure is represented by a pharmacokinetic parameter selected from the group consisting of area under the plasma concentration-time curve ($AUC_{0-t}$), maximum observed concentration ($C_{max}$), time of maximum concentration ($t_{max}$), apparent terminal elimination rate constant ($k_{el}$), and apparent terminal elimination half-life calculated as $\ln(2)/k_{el}(t_{1/2})$;

and wherein the liquid pharmaceutical composition is as provided in one of the following tables:

| Ingredient | Theoretical Quantity (mg/unit dose) | | |
|---|---|---|---|
| | 20-mg Dose | 40-mg Dose | 60-mg Dose |
| Cabozantinib (S)-malate | 25.34 | 50.68 | 76.02 |
| Polyethylene glycol 400 (PEG 400) | 2,934.88 | 5,869.77 | 8,804.65 |
| d-α-tocopheryl polyethylene glycol succinate (TPGS) | 345.28 | 690.56 | 1,035.84 |
| Ethanol | 172.64 | 345.28 | 517.92 |
| Flavorings | 3.45 | 6.91 | 10.36 |
| Total | 3,481.60 | 6,963.19 | 10,444.79 |

| Ingredient | (% w/w) |
|---|---|
| Cabozantinib (S)-malate | 0.73 |
| Polyethylene glycol 400 (PEG 400) | 84.30 |
| d-α-tocopheryl polyethylene glycol succinate (TPGS) | 9.92 |
| Ethanol | 4.96 |
| Flavorings | 0.10 |
| Total | 100 |

| Ingredient | Theoretical Quantity (mg/unit dose) |
|---|---|
| Cabozantinib (S)-malate | 175.00 |
| Polyethylene glycol 400 (PEG 400) | 20,268.53 |
| d-α-tocopheryl polyethylene glycol succinate (TPGS) | 2,384.53 |
| Ethanol | 1,192.27 |
| Flavorings | 23.85 |
| Total | 24,044.18 |

| Ingredient | Function | % w/w |
|---|---|---|
| Cabozantinib (S)-malate | Active Ingredient | 0.73 |
| Polyethylene glycol 400 (PEG 400) | Solubility Enhancer | 84.30 |
| d-α-tocopheryl polyethylene glycol succinate (TPGS) | Solubility Enchancer and Stabilizer | 9.92 |
| Ethanol | Solvent | 4.96 |
| Flavoring | Taste masking agent | 0.10 |
| Total | | 100. |

7. The liquid pharmaceutical composition of claim 6, wherein the liquid formulation when administered to a plurality of patients as a single dose provides an interpatient or intrapatient exposure variability of less than 10%.

8. A method of treating locally advanced or metastatic urothelial carcinoma or renal cell carcinoma, comprising administering a patient in need of such treatment, a liquid pharmaceutical composition comprising Cabozantinib (S)-malate and a pharmaceutically acceptable carrier;

wherein the pharmaceutically acceptable carrier comprises from 50% to 95% polyethyleneglycols (w/w), from 1% to 30% d-α-tocopheryl polyethylene glycol succinate (TPGS, w/w), and from 0.5% to 20% ethanol (w/w); and wherein the liquid formulation when administered to a plurality of patients as a single dose provides an interpatient or intrapatient exposure variability of less than 30%, wherein exposure is represented by a pharmacokinetic parameter selected from the group consisting of area under the plasma concentration-time curve ($AUC_{0-t}$), maximum observed concentration ($C_{max}$), time of maximum concentration ($t_{max}$), apparent terminal elimination rate constant ($k_{el}$), and apparent terminal elimination half-life calculated as $\ln(2)/k_{el}$ ($t_{1/2}$).

9. The method of claim 8, wherein the amount of Cabozantinib (S)-malate present in the liquid formulation, ranges from 1 mg to 200 mg.

10. The method of claim 8, wherein the amount of the Cabozantinib (S)-malate present in the liquid formulation, ranges from 10 mg to 100 mg.

11. The method of claim 8, wherein the carrier comprises from 80% to 90% polyethyleneglycols (w/w), from 5% to 15% TPGS (w/w), and from 1% to 10% ethanol (w/w).

12. The method of claim 8, wherein the carrier further includes flavorings.

13. The method of claim 12, wherein the liquid pharmaceutical composition is as provided in one of the following tables:

| Ingredient | Theoretical Quantity (mg/unit dose) | | |
| --- | --- | --- | --- |
| | 20-mg Dose | 40-mg Dose | 60-mg Dose |
| Cabozantinib (S)-malate | 25.34 | 50.68 | 76.02 |
| Polyethylene glycol 400 (PEG 400) | 2,934.88 | 5,869.77 | 8,804.65 |
| d-α-tocopheryl polyethylene glycol succinate (TPGS) | 345.28 | 690.56 | 1,035.84 |
| Ethanol | 172.64 | 345.28 | 517.92 |
| Flavorings | 3.45 | 6.91 | 10.36 |
| Total | 3,481.60 | 6,963.19 | 10,444.79 |

| Ingredient | (% w/w) |
| --- | --- |
| Cabozantinib (S)-malate | 0.73 |
| Polyethylene glycol 400 (PEG 400) | 84.30 |
| d-α-tocopheryl polyethylene glycol succinate (TPGS) | 9.92 |
| Ethanol | 4.96 |
| Flavorings | 0.10 |
| Total | 100 |

| Ingredient | Theoretical Quantity (mg/unit dose) |
| --- | --- |
| Cabozantinib (S)-malate | 175.00 |
| Polyethylene glycol 400 (PEG 400) | 20,268.53 |
| d-α-tocopheryl polyethylene glycol succinate (TPGS) | 2,384.53 |
| Ethanol | 1,192.27 |
| Flavorings | 23.85 |
| Total | 24,044.18 |

| Ingredient | Function | % w/w |
| --- | --- | --- |
| Cabozantinib (S)-malate | Active Ingredient | 0.73 |
| Polyethylene glycol 400 (PEG 400) | Solubility Enhancer | 84.30 |
| d-α-tocopheryl polyethylene glycol succinate (TPGS) | Solubility Enchancer and Stabilizer | 9.92 |
| Ethanol | Solvent | 4.96 |
| Flavoring | Taste masking agent | 0.10 |
| Total | | 100. |

* * * * *